US008609409B2

(12) United States Patent
Li et al.

(10) Patent No.: US 8,609,409 B2
(45) Date of Patent: Dec. 17, 2013

(54) METHODS AND COMPOSITIONS FOR CELL CULTURE PLATFORM

(75) Inventors: Xiaowei Li, Charleston, SC (US); Ning Zhang, Mount Pleasant, SC (US); Xuejun Wen, Charleston, SC (US)

(73) Assignee: Clemson University, Anderson, SC (US)

( * ) Notice: Subject to any disclaimer, the term of this patent is extended or adjusted under 35 U.S.C. 154(b) by 0 days.

(21) Appl. No.: 13/598,343

(22) Filed: Aug. 29, 2012

(65) Prior Publication Data

US 2013/0288366 A1 Oct. 31, 2013

Related U.S. Application Data

(63) Continuation-in-part of application No. 13/447,041, filed on Apr. 13, 2012, which is a continuation-in-part of application No. 12/794,556, filed on Jun. 4, 2010, now Pat. No. 8,481,067.

(60) Provisional application No. 61/184,163, filed on Jun. 4, 2009.

(51) Int. Cl.
C12N 5/071 (2010.01)
C12N 5/0797 (2010.01)

(52) U.S. Cl.
USPC ............ 435/368; 435/377; 530/326; 977/705

(58) Field of Classification Search
None
See application file for complete search history.

(56) References Cited

U.S. PATENT DOCUMENTS

| | | | |
|---|---|---|---|
| 7,051,654 B2 | 5/2006 | Boland et al. | |
| 7,101,857 B2 | 9/2006 | Sung et al. | |
| 7,282,220 B1 | 10/2007 | Sung et al. | |
| 7,468,192 B2 | 12/2008 | Mizuno et al. | |
| 7,485,617 B1 | 2/2009 | Pohl et al. | |
| 7,786,074 B2 | 8/2010 | Gourdie et al. | |
| 7,828,539 B1 | 11/2010 | Beachley et al. | |
| 7,888,319 B2 | 2/2011 | Gourdie et al. | |
| 7,914,819 B1 | 3/2011 | Wen et al. | |
| 8,124,001 B1 | 2/2012 | Wen et al. | |
| 2003/0175410 A1 | 9/2003 | Campbell et al. | |
| 2003/0198619 A1 | 10/2003 | Dong et al. | |
| 2004/0018295 A1 | 1/2004 | Qiu et al. | |
| 2005/0019404 A1 | 1/2005 | Sung et al. | |
| 2005/0171616 A1 | 8/2005 | Sung et al. | |
| 2006/0149392 A1 | 7/2006 | Hsieh et al. | |
| 2006/0257368 A1 | 11/2006 | Wen | |
| 2007/0077270 A1 | 4/2007 | Wen | |
| 2008/0097606 A1 | 4/2008 | Cragg et al. | |
| 2008/0213238 A1 | 9/2008 | Gandy et al. | |
| 2008/0213334 A1 | 9/2008 | Lockwood et al. | |
| 2010/0015068 A1 | 1/2010 | Karp et al. | |
| 2011/0038921 A1 | 2/2011 | Wen et al. | |
| 2011/0091550 A1 | 4/2011 | Zhang et al. | |

FOREIGN PATENT DOCUMENTS

| | | |
|---|---|---|
| WO | WO 02/102429 A1 | 12/2002 |
| WO | WO 03/040235 A1 | 5/2003 |
| WO | WO 2008/105791 A2 | 9/2008 |
| WO | WO 2010/096795 A1 | 8/2010 |
| WO | WO 2010/120757 A2 | 10/2010 |

OTHER PUBLICATIONS

Agarwal et al. "Stable Nanocolloids of Poorly Soluble Drugs with High Drug Content Prepared Using the Combination of Sonication and Layer-by-Layer Technology" *Journal of Controlled Release* 128:225-260 (2008).

Allen et al. "Clinical relevance of the neurotrophins and their receptors" *Clinical Science* 110:175-191 (2006).

Angele et al. "Characterization of Esterified Hyaluronan-Gelatin Polymer Composites Suitable for Chondrogenic Differentiation of Mesenchymal Stem Cells" *J. Biomed Mater Res* 91A:416-427 (2008).

Awad et al. "Chondrogenic Differentiation of Adipose-Derived Adult Stem Cells in Agarose Alginate and Gelatin Scaffolds" *Biomaterials* 25:3211-3222 (2004).

Barbani et al. "Bioartificial Materials Based on Blends of Collagen and Poly(Acrylic Acid)" *Journal of Applied Polymer Science* 72:971-976 (1999).

Beachley et al. "Effect of Electrospinning Parameters on the Nanofiber Diameter and Length" *Mater Sci Eng C Mater Biol Appl.* 29(3):663-668 (2009).

Beachley et al. "Fabrication of Nanofiber Reinforced Protein Structures for Tissue Engineering" *Mater Sci Eng C Mater Biol Appl.* 29(8):2448-2453 (2009).

Beachley et al. "Polymer Nanofibrous Structures: Fabrication Biofunctionalization and Cell Interactions" *Prog Polym Sci.* 35(7):868-892 (2010).

Beachley et al. "Three Dimensional Aligned Individual Nano-Fibers for Neural Tissue Engineering" *Society for Biomaterials* $33^{rd}$ Annual Meeting Chicago IL (2007) Abstract).

Bellamkonda et al. "Hydrogel-based three-dimensional matrix for neural cells" *Journal of Biomedical Materials Research* 29:663-671 (1995).

Cai et al. "Biodegradable Chitosan Scaffolds Containing Microspheres as Carriers for Controlled Transforming Growth Factor-$\beta_1$ Delivery for Cartilage Tissue Engineering" *Chinese Medical Journal* 120(3):197-203 (2007).

Cai et al. "Injectable glycosaminoglycan hydrogels for controlled release of human basic fibroblast growth factor" *Biomaterials* 26:6054-6067 (2005).

Carmeliet. "Angiogenesis in health and disease" *Nature Medicine* 9(6):653-660 (2003).

(Continued)

*Primary Examiner* — Daniel E Kolker
*Assistant Examiner* — Stacey N MacFarlane
(74) *Attorney, Agent, or Firm* — Myers Bigel Sibley & Sajovec, PA

(57) ABSTRACT

The present invention provides a synthetic cell culture platform, comprising: a two dimensional and/or three dimensional surface comprising peptides conjugated to said surface and methods of using the platform for increasing cell adhesion, stable attachment and/or proliferation of cells grown on the platform and for promoting differentiation of neural stem cells into neurons.

10 Claims, 33 Drawing Sheets

(56) References Cited

OTHER PUBLICATIONS

Cho et al. "Chitosan produces potent neuroprotection and physiological recovery following traumatic spinal cord injury" *The Journal of Experimental Biology* 213:1513-1520 (2010).

Cooke et al. "Effect of rhPDGF-BB Delivery of Mediators of Periodontal Wound Repair" *Tissue Engineering* 12(6):1441-1450 (2006).

Crompton et al. "Polylysine-functionalised thermoresponsive chitosan hydrogel for neural tissue engineering" *Biomaterials* 28:441-449 (2007).

Dash et al. "Kinetic Modeling on Drug Release from Controlled Drug Delivery Systems" *Acta Poloniae Pharmaceutica—Drug Research* 67(3):217-223 (2010).

Decher "Fuzzy Nanoassemblies: Toward Layered Polymeric Multicomposites" *Science* 277:1232-1237 (1997).

Deguchi et al. Implantation of a new porous gelatin-siloxane hybrid into a brain lesion as a potential scaffold for tissue regeneration *Journal of Cerebral Blood Flow & Metabolism* 26:1263-1273 (2006).

Eagle et al. "Axonal Regeneration and Limited Functional Recovery Following Hippocampal Deafferentation" *The Journal of Comparative Neurology* 363:377-388 (1995).

Erggelet et al. Regeneration of Ovine Articular Cartilage Defects by Cell-Free Polymer-Based Implants *Biomaterials* 28:5570-5580 (2007).

Frank et al. "Characterization of DNA Complexes Formed by the Nuclear Receptor Constitutive Androstane Receptor" *The Journal of Biological Chemistry* 278(44):43299-43310 (2003).

Freier et al. "Controlling cell adhesion and degradation of chitosan films by N-acetylation" *Biomaterials* 26:5872-5878 (2005).

Frenkel et al. "Scaffolds for Articular Cartilage Repair" *Annals of Biomedical Engineering* 32(1):26-34 (2004).

Gamez et al. "Photofabricated Gelatin-Based Nerve Conduits: Nerve Tissue Regeneration Potentials" *Cell Transplantation* 13:549-564 (2004).

Gotterbarm et al. "An in vivo Study of a Growth-Factor Enhanced Cell Free Two-Layered Collagen-Tricalcium Phosphate in Deep Osteochondral Defects" *Biomaterials* 27:3387-3395 (2006).

Guo et al. "Novel Gene-Modified-Tissue Engineering of Cartilage Using Stable Transforming Growth Factor-62 1-Transfected Mesenchymal Stem Cells Grown on Chitosan Scaffolds" *Journal of Bioscience and Bioengineering* 103(6):547-556 (2007).

Guo et al. "Porous Chitosan-Gelatin Scaffold Containing Plasmid DNA Encoding Transforming Growth Factor-β1 for Chondrocytes Proliferation" *Biomaterials* 27:1095-1103 (2006).

Gupta et al. "Fast-gelling injectable blend of hyaluronan and methylcellulose for intrathecal localized delivery to the injured spinal cord" *Biomaterials* 27:2370-2379 (2006).

Hannila et al. "The Role of Cyclic AMP Signaling in Promoting Axonal Regeneration After Spinal Cord Injury" *Experimental Neurology* 209:321-332 (2008).

Hattori et al. "Chondrotinase ABC Enhances Axonal Regeneration Across Nerve Gaps" *Journal of Clinical Neuroscience* 15:185-191 (2008).

Horn et al. "Influence of cross-linked hyaluronic acid hydrogels on neurite outgrowth and recovery from spinal cord injury" *J. Neurosurg Spine* 6:133-140 (2007).

Hou et al. "The repair of brain lesion by implantation of hyaluronic acid hydrogels modified with laminin" *Journal of Neuroscience Methods* 148:60-70 (2005).

Huang et al. "In Vitro Characterization of Chitosan-Gelatin Scaffolds for Tissue Engineering" *Biomaterials* 26(36):7616-7627(2005).

Hunziker et al. "Repair of Partial-Thickness Defects in Articular Cartilage: Cell Recruitment from the Synovial Membrane" *The Journal of Bone and Joint Surgery Inc.* 78-A(5):721-733 (1996).

Imitola et al. Directed migration of neural stem cells to sites of CNS injury by the stromal cell-derived factor 1β/CXC chemokine receptor 4 pathway *PNAS* 101(52):18117-18122 (2004).

Inanc et al. "Periodontal Ligament Cellular Structures Engineered with Electrospun Poly(DL-Lactide-co-Glycolide) Nanofibrous Membrane Scaffolds" *Journal of Biomedical Materials Research* 90A:186-195 (2009).

International Preliminary Report on Patentability of International Application No. PCT/US2010/030865 issued Oct. 18, 2011 (9 pages).

International Search Report and Written Opinion of International Application No. PCT/US2010/030865 mailed Dec. 20, 2010 (14 pages).

Jain et al. "In situ gelling hydrogels for conformal repair of spinal cord defects and local delivery of BDNF after spinal cord injury" *Biomaterials* 27:497-504 published online Aug. 15, 2005.

Kim et al. "Porous Chitosan Scaffold Containing Microspheres Loaded with Transforming Growth Factor-Beta1: Implications for Cartilage Tissue Engineering" *Control Release* 91(3):365-374 (2003).

Kim et al. Porous Scaffolds of Gelatin-Hydroxyapatite Nanocomposites Obtained by Biomimetic Approach: Characterization and Antibiotic Drug Release *J. Biomed Mater Res B Appl Biomater* 74(2):686-698 (2005).

Klaver et al. "Bioactive surface for neural electrodes: Decreasing astrocyte proliferation via transforming growth factor-β1" *J Biomed Mater Res 81A*:1011-1016 (2007).

Kuo et al. "Regeneration of Dentin-Pulp Complex with Cementum and Periodontal Ligament Formation Using Dental Bud Cells in Gelatin-Chondroitin-Hyaluronan Tri-Copolymer Scaffold in Swine" *J Biomed Mater Res* 86(A):1062-1068 (2008).

Kuo et al. "Cartilage Tissue Engineering: Its Potential and Uses" *Curr Opin Rheumatol* 18:64-73 (2006).

Kurth et al. "Chondrogenic Potential of Human Synovial Mesenchymal Stem Cells in Alginate" *OsteoArthritis and Cartilage* 15:1178-1189 (2007).

Kwok et al. "The Anti-Inflammatory Natural Product Parthenolide from the Medicinal Herb Feverfew Directly Binds to and Inhibits IκB Kinase" *Chemistry & Biology* 8:759-766 (2001).

Laurent et al. "The structure and function of hyaluronan: An overview" *Immunol Cell Biol* 74(2):A1-7 (1996).

Leach et al. "Development of photocrosslinkable hyaluronic acid-polyethylene glycol-peptide composite hydrogels for soft tissue engineering" *J Biomed Mater Res* vol. 70A:74-82 (2004).

Lee et al. "Effects of the Controlled-Released TGF-beta 1 from Chitosan Microspheres on Chondrocytes Cultured in a Collagen/Chitosan/Glycosaminoglycan Scaffold" *Biomaterials* 25(18):4163-4173 (2004).

Lu et al. "Collagen scaffolds populated with human marrow stromal cells reduce lesion volume and improve functional outcome after traumatic brain injury" *Neurosurgery* 61(3):596-603 (2007).

Luo et al. "Cross-linked hyaluronic acid hydrogel films: new biomaterials for drug delivery" *Journal of Controlled Release* 69:169-184 (2000).

Lutolf et al. "Repair of Bone Defects Using Synthetic Mimetics of Collagenous Extracellular Matrices" *Nature Biotechnology* 21:513-518 (2003).

Lvov et al. "Converting Poorly Soluble Materials into Stable Aqueous Nanocolloids" *Langmuir* 27(3):1212-1217 (2011).

Mao et al. "The properties of chitosan-gelatin membranes and scaffolds modified with hyaluronic acid by different methods" *Biomaterials* 24:1621-1629 (2003).

Martino et al. "Chitosan: A Versatile Biopolymer for Orthopaedic Tissue-Engineering" *Biomaterials* 26:5983-5990 (2005).

Matsuda and Magoshi. "Preparation of Vinylated Polysaccharides and Photofabrication of Tubular Scaffolds as Potential Use in Tissue Engineering" *Biomacromolecules* 3:942-950 (2002).

Murphy et al. "Engagement of CD44 modulates cyclooxygenase induction, VEGF generation and proliferation in human vascular endothelial cells" *The FASEB Journal* 19:446-448 (2005).

Nicholas et al. "Denatured Thiolated Collagen" *Biomaterials* 18:807-813 (1997).

Nisbet et al. "Review Neural Tissue Engineering of the CNS Using Hydrogels" *J Biomed Mater Res Part B: Appl Biomater* 87B: 251-263 (2008).

(56) References Cited

OTHER PUBLICATIONS

Nomura et al. "Extramedullary Chitosan Channels Promote Survival of Transplanted Neural Stem and Progenitor Cells and Create a Tissue Bridge After Complete Spinal Cord Transection" *Tissue Engineering: Part A* 14(5): 649-665 (published online Apr. 17, 2008).
Okuda et al. "Time-Programmed Dual Release Formulation by Multilayered Drug-Loaded Nanofiber Meshes" *Journal of Controlled Release* 143:258-264 (2010).
Page et al. "The Pathogenesis of Human Periodontitis: an Introduction" *Periodontology* 14:9-11 (1997).
Peattie et al. "Stimulation of in vivo angiogenesis by cytokine-loaded hyaluronic acid hydrogel implants" *Biomaterials* 25:2789-2798 (2004).
Peattie et al. "Dual growth factor-induced angiogenesis in vivo using hyaluronan hydrogel implants" *Biomaterials* 27:1868-1875 (2006).
Pike et al. "Heparin-Regulated Release of Growth Factors In Vitro and Angiogenic Response In Vivo to Implanted Hyaluronan Hydrogels Containing VEGF and bFGF" *Biomaterials* 27:5242-5251 (2006).
Plant et al. "Implantation of Collagen IV/poly(2-hydroxyethyl Methacrylate) Hydrogels Containing Schwann Cells into the Lesioned Rat Optic Tract" *Cell Transplant* 4:381-91 (1998).
Ponticiello et al. "Gelatin-Based Resorbable Sponge as a Carrier Matrix for Human Mesenchymal Stem Cells in Cartilage Regeneration Therapy" *J. Biomed Mater Res* 52:246-255 (2000).
Prestwich et al. "Injectable synthetic extracellular matrices for tissue engineering and repair" *Adv Exp Med Biol* 585:125-133 (2007).
Qiu et al. "Chemically Modified Light-Curable Chitosans with Enhanced Potential for Bone Tissue Repair" *J Biomed Mater Res* 89(A):772-779 (2009).
Qiu et al. "Fabrication of Permeable Tubular Constructs From Chemically Modified Chitosan With Enhanced Antithrombogenic Property" *J Biomed Mater Res Part B: Appl Biomater* 90B:668-678 (2009).
Qiu. "Chitosan Derivatives for Tissue Engineering" Clemson University Ph.D. degree thesis Aug. 2008 (11 pages).
Radice et al. "Hyaluronan-based biopolymers as delivery vehicles for bone-marrow-derived mesenchymal progenitors" *J Biomed Mater Res* vol. 50:101-109 (2000).
Reichardt. "Neurotrophin-regulated signalling pathways" *Phil. Trans. R. Soc. B* 361:1545-1564 (2000).
Riley et al. "Stimulation of in vivo angiogenesis using dual growth factor-loaded crosslinked glycosaminoglycan hydrogels" *Biomaterials* 27(35):5935-5943 (2007).
Sanes. "Roles of Extracellular Matrix in Neural Development" *Ann. Rev. Physiol.* 45:581-600 (1983).
Schagemann et al. "Cell-Laden and Cell-Free Biopolymer Hydrogel for the Treatment of Osteochondral Defects in a Sheep Model" *Tissue Engineering* Part A 15(1):75-83 (2009).
Segura et al. "Crosslinked hyaluronic acid hydrogels: a strategy to functionalize and pattern" *Biomaterials* 26:359-371 (2005).
Sharma et al. "A Select Combination of Neurotrophins Enhances Neuroprotection and Functional Recovery following Spinal Cord Injury" *Annals of the New York Academy of Sciences* 112:95-111 (2007).
Shor et al. "Fabrication of Three-Dimensional Polycaprolactone/Hydroxyapatite Tissue Scaffolds and Osteoblast-Scaffold Interactions in vitro" *Biomaterials* 28:5291-5297 (2007).
Shu et al. "Attachment and spreading of fibroblasts on an RGD peptide-modified injectable hyaluronan hydrogel" *J Biomed Mater Res* 68A:365-375 (2004).
Shu et al. "Disulfide Cross-Linked Hyaluronan Hydrogels" *Biomacromolecules* 3:1304-1311 (2002).
Shu et al. "Disulfide-crosslinked hyaluronan-gelatin hydrogel films: a covalent mimic of the extracellular matrix for in vitro cell growth" *Biomaterials* 24:3825-3834 (2003).
Shu et al. "In situ crosslinkable hyaluronan hydrogels for tissue engineering" *Biomaterials* 25:1339-1348 (published online Oct. 14, 2003).

Shu et al. "Synthesis and evaluation of injectable in situ crosslinkable synthetic extracellular matrices for tissue engineering" *J Biomed Mater Res* 79A:902-912 (2006).
Sill et al. "Electrospinning: Applications in Drug Delivery and Tissue Engineering" *Biomaterials* 29:1989-2006 (2008).
Slater et al. "An In Vitro Model of the Glomerular Capillary Wall Using Electrospun Collagen Nanofibres in a Bioartificial Composite Basement Membrane" *PLoS One* 6(6):e20802 (2011).
Solchaga et al. "Hyaluronan-based Polymers in the Treatment of Osteochondral Defects" *Journal of Orthopaedic Research* 18(5):773-780 (2000).
Stabenfeldt et al. "Thermoreversible laminin-functionalized hydrogel for neural tissue engineering" *J Biomed Mater Res* 77A:718-725 (2006).
Stoop "Smart Biomaterials for Tissue Engineering of Cartilage" *Injury Int. J. Care Injured* 39S1:77-87 (2008).
Taba et al. "Current Concepts in Periodontal Bioengineering" *Orthod Craniofacial Res* 8:292-302 (2005).
Tamai et al. "A New Biotechnology for Articular Cartilage Repair: Subchondral Implantation of a Composite of Interconnected Porous Hydroxyapatite Synthetic Polymer (PLA-PEG) and Bone Morphogenetic Protein-2 (rhBMP-2)" *OsteoArthritis and Cartilage* 13:405-417 (2005).
Tate et al. "Biocompatibility of methylcellulose-based constructs designed for intracerebral gelation following experimental traumatic brain injury" *Biomaterials* 22:1113-1123 (2001).
Tian et al. "Hyaluronic Acid-Poly-D-Lysine-Based Three-Dimensional Hydrogel for Traumatic Brain Injury" *Tissue Engineering* 11(3-4):513-528 (2005).
Trochon et al. "Evidence of Involvement of CD44 in Endothelial Cell Proliferation Migration and Angiogenesis" *In Vitro Int. J. Cancer* 66:664-668 (1996).
Wade et al. "Efficacy of hypertonic saline dextran (HSD) in patients with traumatic hypotension: meta-analysis of individual patient data" *Acta Anaesthesiol Scand Suppl* 110:77-79 (1997).
Wei et al. "Nano-Fibrous Scaffold for Controlled Delivery of Recombinant Human PDGF-BB" *J Control Release* 112(1):103-110 (2006).
Wei et al. "Hyaluronic acid hydrogels with IKVAV peptides for tissue repair and axonal regeneration in an injured rat brain" *Biomed. Mater.* 2:S142-S146 (2007).
Wells et al. "Gel Matrix Vehicles for Growth Factor Application in Nerve Gap Injuries Repaired with Tubes: A Comparison of Biomatrix Collagen and Methylcellulose" *Experimental Neurology* 146:395-402 (1997).
Wen "Regeneration of Cartilage In Vivo Without Cell Transplantation: A Bioengineering Strategy" Program for South Carolina Science Technology and Health Conference and 2009 Annual Meeting of the South Carolina Academy of Science Apr. 14-15, 2009.
Wissink et al. "Binding and release of basic fibroblast growth factor from heparinized collagen matrices" *Biomaterials* 22:2291-2299 (2001).
Wissink et al. "Immobilization of heparin to EDC/NHS-crosslinked collagen. Characterization and in vitro evaluation" *Biomaterials* 22:151-163 (2001).
Woerly et al. "Neural Tissue Formation Within Porous Hydrogels Implanted in Brain and Spinal Cord Lesions: Ultrastructural Immunohistochemical and Diffusion Studies" *Tissue Eng* 5(5):467-488 (1999).
Wong et al. "Effect of Naringin on Bone Cells" *Journal of Orthopaedic Research* 24:2045-2050 (2006).
Wood et al. "Controlling Interlayer Diffusion to Achieve Sustained Multiagent Delivery from Layer-by-Layer Thin Films" *PNAS* 103(27):10207-10212 (2006).
Yang et al. "Nanofiber Enabled Layer-by-Layer Approach toward Three-Dimensional Tissue Formation" *Tissue Engineering* 15(4):945-956 (2009).
Zhang et al. "Three-Dimensional Nanohydroxyapatite/Chitosan Scaffolds as Potential Tissue Engineered Periodontal Tissue" *Journal of Biomaterials Applications* 21:333-349 (2007).

(56) References Cited

OTHER PUBLICATIONS

Zhang et al. "Drug-Loaded Degradable Nano-Particles for the Rescue of Tissue Under Hypoxia Condition and Promote Angiogenesis" 229th ACS National Meeting San Diego CA Mar. 13, 2005.

Zhang et al. "Synthesis and characterization of biocompatible degradable light-curable polyurethane-based elastic hydrogels" *J Biomed Mater Res 82A*:637-650 (2007).

Zhang et al. "Fabrication of semipermeable hollow fiber membranes with highly aligned texture for nerve guidance" *J Biomed Mater Res 75A*:941-949 (2005).

Zhang et al. "Tissue-engineering approaches for axonal guidance" *Brain Research Reviews* 49:48-64 (2005)(abstract).

Zhao et al. "Recruitment of Endogenous Stem Cells for Tissue Repair" *Macromol. Biosci.* 8:836-842 (2008).

Zhong et al. "Controlled release of anti-inflammatory agent α-MSH from neural implants" *Journal of Controlled Release* 106:309-318 (2005).

3 mm at low magnification, 300 μm at high magnification 3 mm at low magnification, 300 μm at high magnification

SEQUENCE LISTING

<160> NUMBER OF SEQ ID NOS: 21

<210> SEQ ID NO 1
<211> LENGTH: 12
<212> TYPE: PRT
<213> ORGANISM: Artificial
<220> FEATURE:
<223> OTHER INFORMATION: Laminin-derived short peptide sequence

<400> SEQUENCE: 1

Cys Cys Arg Arg Ile Lys Val Ala Val Trp Leu Cys
1               5                   10

<210> SEQ ID NO 2
<211> LENGTH: 25
<212> TYPE: PRT
<213> ORGANISM: Artificial

```
<220> FEATURE:
<223> OTHER INFORMATION: Laminin-derived peptide sequence

<400> SEQUENCE: 2

Cys Asp Pro Val Cys Cys Gly Thr Ala Arg Pro Gly Tyr Ile Gly Ser
1               5                   10                  15

Arg Gly Thr Ala Arg Cys Cys Ala Cys
            20                  25

<210> SEQ ID NO 3
<211> LENGTH: 13
<212> TYPE: PRT
<213> ORGANISM: Artificial
<220> FEATURE:
<223> OTHER INFORMATION: Laminin-derived peptide sequence

<400> SEQUENCE: 3

Cys Cys Arg Arg Tyr Val Val Leu Pro Arg Trp Leu Cys
1               5                   10

<210> SEQ ID NO 4
<211> LENGTH: 16
<212> TYPE: PRT
<213> ORGANISM: Artificial
<220> FEATURE:
<223> OTHER INFORMATION: Laminin-derived peptide sequence

<400> SEQUENCE: 4

Cys Cys Arg Arg Asn Ile Ala Glu Ile Ile Lys Asp Ile Trp Leu Cys
1               5                   10                  15

<210> SEQ ID NO 5
<211> LENGTH: 12
<212> TYPE: PRT
<213> ORGANISM: Artificial
<220> FEATURE:
<223> OTHER INFORMATION: Laminin-derived peptide sequence

<400> SEQUENCE: 5

Cys Cys Arg Arg Tyr Ile Gly Ser Arg Trp Leu Cys
1               5                   10

<210> SEQ ID NO 6
<211> LENGTH: 25
<212> TYPE: PRT
<213> ORGANISM: Artificial
<220> FEATURE:
<223> OTHER INFORMATION: Laminin-derived peptide sequence

<400> SEQUENCE: 6

Cys Asp Pro Val Cys Cys Gly Thr Ala Arg Pro Gly Tyr Ile Gly Ser
1               5                   10                  15

Arg Gly Thr Ala Arg Cys Cys Ala Cys
            20                  25

<210> SEQ ID NO 7
<211> LENGTH: 29
<212> TYPE: PRT
<213> ORGANISM: Artificial
<220> FEATURE:
<223> OTHER INFORMATION: Laminin-derived peptide sequence

<400> SEQUENCE: 7

Cys Asp Pro Val Cys Cys Gly Thr Ala Arg Pro Gly Asn Ile Ala Glu
1               5                   10                  15

Ile Ile Lys Asp Ile Gly Thr Ala Arg Cys Cys Ala Cys
```

```
            20                  25

<210> SEQ ID NO 8
<211> LENGTH: 26
<212> TYPE: PRT
<213> ORGANISM: Artificial
<220> FEATURE:
<223> OTHER INFORMATION: Laminin-derived peptide sequence

<400> SEQUENCE: 8

Cys Asp Pro Val Cys Cys Gly Thr Ala Arg Pro Gly Tyr Val Val Leu
1               5                   10                  15

Pro Arg Gly Thr Ala Arg Cys Cys Ala Cys
            20                  25

<210> SEQ ID NO 9
<211> LENGTH: 25
<212> TYPE: PRT
<213> ORGANISM: Artificial
<220> FEATURE:
<223> OTHER INFORMATION: Laminin-derived peptide sequence

<400> SEQUENCE: 9

Cys Asp Pro Val Cys Cys Gly Thr Ala Arg Pro Gly Ile Lys Val Ala
1               5                   10                  15

Val Gly Thr Ala Arg Cys Cys Ala Cys
            20                  25

<210> SEQ ID NO 10
<211> LENGTH: 14
<212> TYPE: PRT
<213> ORGANISM: Artificial
<220> FEATURE:
<223> OTHER INFORMATION: Fibronectin-derived peptide sequence

<400> SEQUENCE: 10

Cys Cys Arg Arg Gly Arg Gly Asp Ser Pro Lys Trp Leu Cys
1               5                   10

<210> SEQ ID NO 11
<211> LENGTH: 19
<212> TYPE: PRT
<213> ORGANISM: Artificial
<220> FEATURE:
<223> OTHER INFORMATION: Fibronectin-derived peptide sequence

<400> SEQUENCE: 11

Cys Cys Arg Arg Ala Val Thr Gly Arg Gly Asp Ser Pro Ala Ser Ser
1               5                   10                  15

Trp Leu Cys

<210> SEQ ID NO 12
<211> LENGTH: 32
<212> TYPE: PRT
<213> ORGANISM: Artificial
<220> FEATURE:
<223> OTHER INFORMATION: Fibronectin-derived peptide sequence

<400> SEQUENCE: 12

Cys Asp Pro Val Cys Cys Gly Thr Ala Arg Pro Gly Pro Gln Val Thr
1               5                   10                  15

Arg Gly Asp Val Phe Thr Met Pro Gly Thr Ala Arg Cys Cys Ala Cys
            20                  25                  30

<210> SEQ ID NO 13
```

```
<211> LENGTH: 23
<212> TYPE: PRT
<213> ORGANISM: Artificial
<220> FEATURE:
<223> OTHER INFORMATION: Fibronectin-derived peptide sequence

<400> SEQUENCE: 13

Cys Asp Pro Val Cys Cys Gly Thr Ala Arg Pro Gly Arg Gly Asp Gly
1               5                   10                  15

Thr Ala Arg Cys Cys Ala Cys
            20

<210> SEQ ID NO 14
<211> LENGTH: 19
<212> TYPE: PRT
<213> ORGANISM: Artificial
<220> FEATURE:
<223> OTHER INFORMATION: Vitronectin-derived peptide sequence

<400> SEQUENCE: 14

Cys Cys Arg Arg Pro Gln Val Thr Arg Gly Asp Val Phe Thr Met Pro
1               5                   10                  15

Trp Leu Cys

<210> SEQ ID NO 15
<211> LENGTH: 19
<212> TYPE: PRT
<213> ORGANISM: Artificial
<220> FEATURE:
<223> OTHER INFORMATION: Laminin-derived peptide sequence

<400> SEQUENCE: 15

Cys Ser Arg Ala Arg Lys Gln Ala Ala Ser Ile Lys Val Ala Val Ser
1               5                   10                  15

Ala Asp Arg

<210> SEQ ID NO 16
<211> LENGTH: 5
<212> TYPE: PRT
<213> ORGANISM: Artificial
<220> FEATURE:
<223> OTHER INFORMATION: Laminin-derived peptide sequence

<400> SEQUENCE: 16

Ile Lys Val Ala Val
1               5

<210> SEQ ID NO 17
<211> LENGTH: 5
<212> TYPE: PRT
<213> ORGANISM: Artificial
<220> FEATURE:
<223> OTHER INFORMATION: Laminin-derived peptide sequence

<400> SEQUENCE: 17

Tyr Ile Gly Ser Arg
1               5

<210> SEQ ID NO 18
<211> LENGTH: 7
<212> TYPE: PRT
<213> ORGANISM: Artificial
<220> FEATURE:
<223> OTHER INFORMATION: Laminin-derived peptide sequence
```

```
<400> SEQUENCE: 18

Arg Tyr Val Val Leu Pro Arg
1               5

<210> SEQ ID NO 19
<211> LENGTH: 10
<212> TYPE: PRT
<213> ORGANISM: Artificial
<220> FEATURE:
<223> OTHER INFORMATION: Laminin-derived peptide sequence

<400> SEQUENCE: 19

Arg Asn Ile Ala Glu Ile Ile Lys Asp Ile
1               5                   10

<210> SEQ ID NO 20
<211> LENGTH: 9
<212> TYPE: PRT
<213> ORGANISM: Artificial
<220> FEATURE:
<223> OTHER INFORMATION: Laminin-derived peptide sequence

<400> SEQUENCE: 20

Cys Asp Pro Gly Tyr Ile Gly Ser Arg
1               5

<210> SEQ ID NO 21
<211> LENGTH: 6
<212> TYPE: PRT
<213> ORGANISM: Artificial
<220> FEATURE:
<223> OTHER INFORMATION: Laminin-derived peptide sequence

<400> SEQUENCE: 21

Gly Tyr Ile Gly Ser Arg
1               5
```

METHODS AND COMPOSITIONS FOR CELL CULTURE PLATFORM

STATEMENT OF PRIORITY

The present application is a continuation-in-part application of U.S. application Ser. No. 13/447,041, filed Apr. 13, 2012, which is a continuation-in-part application of U.S. application Ser. No. 12/794,556, filed Jun. 4, 2010 now U.S. Pat. No. 8,481,067, which claims the benefit, under 35 U.S.C. §119(e), of U.S. Provisional Application No. 61/184,163, filed Jun. 4, 2009, the entire contents of each of which are incorporated by reference herein.

STATEMENT OF GOVERNMENT SUPPORT

Aspects of this invention were supported by government funding under Grant Nos. R01 NS050243 and P20RR021949 from the National Institutes of Health, Grant No. CBET0748129 from the National Science Foundation and Grant Nos. SC090380 and PT073600 from the Department of Defense. The U.S. Government has certain rights in this invention.

STATEMENT REGARDING ELECTRONIC FILING OF A SEQUENCE LISTING

A Sequence Listing in ASCII text format, submitted under 37 C.F.R. §1.821, entitled 9662-4IP2_SUBSTITUTE.txt, 6,002 bytes in size, generated on Oct. 30, 2012 and filed via EFS-Web, is provided in lieu of a paper copy. The Sequence Listing is hereby incorporated by reference into the specification for its disclosures.

FIELD OF THE INVENTION

The present invention relates to methods of treating central nervous system lesions, including promoting revascularization and/or reenervation. The present invention also relates to treating spinal cord injury, including reducing inhibition of axonal regeneration and/or decreasing secondary injury at a spinal cord injury site.

BACKGROUND OF THE INVENTION

Brain stroke ranks as the third leading cause of death and disability in most developed countries (Wolfe et al., *J. Neurol. Neurosurg. Psychiatry* 72:211 (2002), and is the second most common cause of death worldwide (Murray et al., *Lancet* 349:1269 (1997)). About ⅙ of all human beings will suffer at least one stroke in their lives (Seshadri et al., *Stroke* 37:345 (2006)). Stroke can be hemorrhagic, ischemic, or embolic in origin. Each year, 500,000 new cases of brain strokes are reported in the US (Higashida et al., *Am. J. Neuroradiol.* 26:2323 (2005)). Depending upon the particular cerebral vessels involved, stroke patients may have a one-year mortality rate ranging from 60% to 8% (Murray et al., *Lancet* 349:1269 (1997); Salgado et al., *Stroke* 27:661 (1996)). Nonetheless, the surviving stroke patients usually remain severely disabled and require constant care for the rest of their lives.

Despite tremendous effort in thrombolysis and neuroprotection, no effective treatment is available for cerebral stroke in clinical settings. This is largely due to the inability of current treatments to repopulate the stroke lesion cavity with functional neurons and glial cells, which dynamically participate in cell-cell signaling and provide sustained trophic support that is critical for decreased neural degeneration and sustained functional recovery. In support of this notion, neural transplantation strategies have been developed to reconstruct the stroke lesion cavity. Despite its efficacy in providing sustained functional recovery in other types of central nervous system (CNS) injuries, neural transplantation for cerebral stroke repair has had limited success, due to poor donor cell survival and functionality at the infarct site (Savitz et al., *NeuroRx* 1:406 (2004)).

An accumulating body of evidence has indicated the predominant role of glial scar tissue in obstructing brain tissue regeneration and structural repair following stroke (Lipton, *Physiol. Rev.* 79:1431 (1999); Gartshore et al., *Exp. Neurol.* 147:353 (1997)). The dense scar tissue outlining a stroke lesion cavity typically consists of endogenous and/or hematogenous inflammatory cells embedded within a dense, remodeling extracellular matrix (Fitch et al., *J. Neurosci.* 19:8182 (1999); Lindsay, Reactive gliosis. In: Fedoroff S, Vernadakis A, editors. *Astrocytes* Orlando: Academic Press; 1986. pp. 231-262; Preston et al., *J. Neurotrauma* 18:83 (2001)). The presence of the scar tissue not only contributes to regenerative failure, but also to the poor survival and functionality of transplanted cells, and poses a diffusive barrier that hinders the effective delivery of nutrients, oxygen, and pharmacological agents into the lesion cavity.

Since any reparative therapy designed to regenerate brain tissue following a stroke will take place in the lesion site, there is a critical need for strategies to overcome the inhibitory scar and promote neuronal regeneration and reconstruction across the lesion cavity. Most importantly, a well-structured vasculature network that completely re-fills the stroke lesion cavity is a prerequisite to support the brain tissue regeneration process.

Spinal cord injury (SCI) continues to affect a significant number of individuals, especially those in the 18-50 age group (National Spinal Cord Injury Statistical Center (NSCISC) "Spinal Cord Injury Facts and Figures at a Glance" Birmingham: University of Alabama (2010). The injury process involves primary and secondary components (Fehlings et al. "Current status of clinical trials for acute spinal cord injury" *Injury* 36 Suppl 2:B113-22 (2005); Hall et al. "Neuroprotection and acute spinal cord injury: a reappraisal" *Neurorx* 1(1):80-100 (2004); Onose et al. "A review of published reports on neuroprotection in spinal cord injury" *Spinal Cord* 47(10):716-26 (2009). Primary injury occurs immediately after trauma and mainly involves axonal loss at the injury epicenter. Subsequent local inflammation induces secondary injury from the release of cytokines, activation of microglia, and post-traumatic ischemia (Tator et al. "Review of the secondary injury theory of acute spinal cord trauma with emphasis on vascular mechanisms. *J Neurosurg* 75(1):15-26 (1991). Secondary injury leads to delayed necrosis and apoptosis resulting in further neuronal loss. In efforts to minimize secondary injury, several neuroprotection strategies have been investigated in randomized control trials. The most notable among these trials were the first and second National Acute Spinal Cord Injury Studies (NASCIS) (Bracken et al. "Efficacy of methylprednisolone in acute spinal cord injury" *JAMA* 251(1):45-52 (1984); Bracken et al. "A randomized, controlled trial of methylprednisolone or naloxone in the treatment of acute spinal-cord injury. Results of the Second National Acute Spinal Cord Injury Study" *N. Engl. J. Med.* 322(20):1405-11 (1990). The results from both these trials, as well as many subsequent studies focusing on the different treatment strategies, have shown no benefit in secondary injury prevention.

The present invention overcomes these shortcomings by providing methods for promoting revascularization and/or

SUMMARY OF THE INVENTION

One aspect of the present invention relates to methods of promoting revascularization in a CNS lesion, comprising delivering to the lesion an amount of a hydrogel of this invention effective to promote revascularization of the lesion. In one embodiment, the hydrogel does not comprise any angiogenic factors.

A further aspect of the present invention relates to methods of promoting revascularization and reenervation of a CNS lesion and/or repair/regeneration of a CNS lesion, comprising delivering to the lesion an amount of a hydrogel of this invention effective to promote revascularization and reenervation of the lesion.

A further aspect of the present invention relates to methods of recruiting neural stem cells to a CNS lesion, comprising delivering a hydrogel of this invention that contains at least one neural stem cell recruiting factor to the lesion in an amount effective to promote both revascularization of the lesion and recruitment of neural stem cells to the lesion. In certain embodiments, the neural stem cell recruiting factor is selected from the group consisting of hepatocyte growth factor, gliotropic factors (e.g., human recombinant annexin A2), stem cell factor-1, stromal cell-derived factor-1 (SDF-1), chemokine monocyte chemoattractant protein-1 (MCP-1, SCYA2, CCL2, MCAF), vascular endothelial growth factor (VEGF), epidermal growth factor (EGF), transmembrane protein 18, glioma-produced ECM (tenascin-C), IGF-1, FGF-2, PDGF and any combination thereof in any ratio.

A further aspect of the present invention relates to methods of repopulating a CNS lesion with functional neurons, comprising delivering a hydrogel of this invention that contains at least one neural stem cell recruiting factor and neurogenic factor to the lesion in an amount effective to promote both revascularization of the lesion and repopulation of the lesion with functional neurons. In certain embodiments, the neural stem cell recruiting factor is selected from the group consisting of hepatocyte growth factor, gliotropic factors (e.g., human recombinant annexin A2), stem cell factor-1, stromal cell-derived factor-1 (SDF-1), chemokine monocyte chemoattractant protein-1 (MCP-1, SCYA2, CCL2, MCAF), vascular endothelial growth factor (VEGF), epidermal growth factor (EGF), transmembrane protein 18, glioma-produced ECM (tenascin-C), IGF-1, FGF-2, PDGF and any combination thereof in any ratio.

A further aspect of the present invention relates to methods of repopulating a CNS lesion with functional neurons, comprising delivering a hydrogel of this invention that contains at least one mitogen for neural stem cell proliferation/expansion to the lesion in an amount effective to promote both revascularization of the lesion and repopulation of the lesion with functional neurons. In some embodiments, the mitogen for neural stem cells is selected from the group consisting of EGF, FGF-2, PDGF and any combination thereof in any ratio.

A further aspect of the present invention relates to methods of repopulating a CNS lesion with functional neurons, comprising delivering a hydrogel of this invention that contains at least one neural differentiation factor to the lesion in an amount effective to promote both revascularization of the lesion and repopulation of the lesion with functional neurons. In certain embodiments, the neural differentiation factor is selected from the group consisting of BDNF, NT-3, GDNF, CNTF and any combination thereof in any ratio.

A further aspect of the present invention relates to methods of repopulating a CNS lesion with functional neurons, comprising delivering a hydrogel of this invention to the lesion in an amount effective to promote revascularization of the lesion, and delivering at least one neural stem cell mobilizing factor to the central nervous system (CNS) of the subject having the lesion. In certain embodiments, the neural stem cell mobilizing factor is delivered to the subventricular zone. In some embodiments, the neural stem cell mobilizing factor is selected from the group consisting of leukemia inhibitory factor, granulocyte-colony stimulating factor and any combination thereof in any ratio.

A further aspect of the present invention relates to methods of repopulating a CNS lesion with functional neurons, comprising: delivering a hydrogel of this invention to the lesion in an amount effective to promote revascularization of the lesion, and delivering both a neural stem cell recruiting factor and a neural stem cell mobilizing factor to the CNS of the subject having the lesion. In certain embodiments, the neural stem cell recruiting factor is present in the hydrogel and the neural stem cell mobilizing factor is delivered to the subventricular zone. In other embodiments, the neural stem cell recruiting factor is hepatocyte growth factor and the neural stem cell mobilizing factor is leukemia inhibitory factor.

A further aspect of the present invention relates to methods of repairing a CNS lesion, comprising delivering to the lesion an amount of a hydrogel of this invention effective to promote the revascularization and reenervation of the lesion, thereby repairing the CNS lesion.

A further aspect of the present invention relates to methods of treating a disorder resulting from a CNS lesion, comprising delivering to the lesion an amount of a hydrogel of this invention effective to promote the revascularization and reenervation of the lesion and to treat at least one symptom of the disorder resulting from the CNS lesion.

A further aspect of the present invention relates to methods of preventing scar tissue growth in a CNS lesion, comprising delivering to the lesion an amount of a hydrogel of this invention comprising at least one agent that blocks the biosynthesis of inhibitory ECM components, wherein said amount is effective to prevent scarring. In certain embodiments, the agent is selected from the group consisting of p-nitrophenyl-b-D-xylopyranoside, dimethyloxalylglycine, cyclic nucleotides, and any combinations thereof in any ratio.

A further aspect of the present invention relates to methods of digesting scar tissue in a CNS lesion, comprising delivering to the lesion an amount of a hydrogel of this invention comprising at least one ECM-degrading enzyme, wherein said amount is effective to digest scar tissue. In certain embodiments, the enzyme is selected from the group consisting of chondroitinase ABC, collagenase IV, and any combination thereof in any ratio.

A further aspect of the present invention relates to methods of maintaining a scar-reduced environment in a CNS lesion, comprising delivering to the lesion site an amount of a hydrogel of this invention comprising at least one agent that blocks the biosynthesis of inhibitory ECM components and/or reduces recruitment of inflammatory cells to the lesion site and/or reduces activity of inflammatory cells at the lesion site and, optionally, at least one ECM-degrading enzyme, wherein said amount is effective to maintain a scar-reduced environment at the lesion site. In certain embodiments, the agent can be, e.g., p-nitrophenyl-b-D-xylopyranoside, dimethyloxalylglycine, cyclic nucleotides, and any combination thereof, and the enzyme can be chondroitinase ABC, collagenase IV, and any combination thereof.

A further aspect of the invention is a method of treating a spinal cord injury, comprising topically delivering to the spinal cord injury site an amount of a neurotrophic factor and/or an anti-inflammatory agent effective to treat the spinal cord injury.

Also provided herein is a method of reducing inhibition of axonal regeneration at a spinal cord injury site, comprising topically delivering to the site an amount of a neurotrophic factor and/or an anti-inflammatory agent effective in reducing inhibition of axonal regeneration at the spinal cord injury site.

Another aspect of this invention is a method of decreasing secondary injury at a spinal cord injury site, comprising topically delivering to the site an amount of a neurotrophic factor and/or an anti-inflammatory agent effective in decreasing secondary injury at the spinal cord injury site.

In additional aspects, the present invention provides a method of delivering a neurotrophic factor and/or an anti-inflammatory agent to a spinal cord injury site, comprising topically delivering to the spinal cord injury site a vehicle comprising the neurotrophic factor and/or anti-inflammatory agent, wherein the vehicle is selected from the group consisting of a hydrogel, a nanosphere, microsphere, membrane, scaffold or any combination thereof, thereby delivering the neurotrophic factor and/or the anti-inflammatory agent to the spinal cord injury site.

A further aspect is a method of preventing or reducing scar tissue growth at a spinal cord injury site, comprising topically delivering to the site an effective amount of at least one agent that blocks the biosynthesis of inhibitory extracellular matrix components and/or reduces recruitment of inflammatory cells to the site and/or reduces activity of inflammatory cells, thereby preventing or reducing scar tissue growth at the spinal cord injury site.

The present invention also provides a method of recruiting stem cells to a spinal cord injury site, comprising topically delivering to the site at least one neural stem cell recruiting factor.

In a further aspect, the present invention provides a method of treating a spinal cord injury, comprising topically delivering to the spinal cord injury site an amount of a chitosan-gelatin based hydrogel effective to treat the spinal cord injury.

Also provided herein is a method of reducing inhibition of axonal regeneration at a spinal cord injury site, comprising topically delivering to the site an amount of a chitosan-gelatin based hydrogel effective in reducing inhibition of axonal regeneration at the spinal cord injury site.

Another aspect of this invention is a method of decreasing secondary injury at a spinal cord injury site, comprising topically delivering to the site an amount of a chitosan-gelatin based hydrogel effective in decreasing secondary injury at the spinal cord injury site.

In additional aspects, the present invention provides a synthetic cell culture platform, comprising: a two dimensional and/or three dimensional surface comprising peptides conjugated to said surface, said peptides comprising one or more peptides of this invention (e.g., a peptide having the amino acid sequence of any one of SEQ ID NOS:1 to 14 or a combination thereof). In a representative embodiment, the peptide comprises the amino acid sequence CCR-RIKVAVWLC (SEQ ID NO:1).

In a further aspect, the present invention provides a method of increasing cell adhesion, stable attachment and/or proliferation of cells, the method comprising: contacting the cells with a platform of the invention; and culturing the cells on said platform, wherein the cells have increased cell adhesion, stable attachment and proliferation as compared to control cells not grown on a platform of the invention (e.g., a platform that does not comprise, consist essentially of, consist of peptides of this invention.

In still further embodiments, a method of promoting differentiation of neural stem cells into neurons is provided, comprising: contacting neural stem cells with a platform of the present invention; and culturing the cells on said platform, wherein the differentiation of the neural stem cells into neurons is promoted.

These and other aspects of the present invention will be discussed in more detail in the description of the invention set forth below.

BRIEF DESCRIPTION OF THE FIGURES

FIGS. 5A, 5C, 5D. Adult rat brain four weeks after focal ischemic stroke (untreated). FIGS. 5B, 5E, 5F. Adult rat brain treated with an in-situ crosslinkable hydrogel four weeks after focal ischemic stroke. FIGS. 5A-5B depict the gross morphology of the brains. FIGS. 5C, 5E contain mosaic image reconstructions of the lesions. Higher resolution images of the lesion interfaces are provided in FIGS. 5D and 5F. Light grey corresponds to GFAP staining for astrocytes. Dark grey represents Reca-1 staining for blood vessels. As shown in panel E, a well-structured vasculature network was rebuilt at the lesion injected with the in-situ crosslinkable hydrogel of the present invention.

Cells were stained with DAPI (blue), GFAP (green), and β III tubulin (red). Scale bar=100 µm.

FIG. 21A-21C. Oscillatory time sweep (A), stress sweep (B), and frequency sweep (C) of hydrogel based on 4-arm thiolated PEG (2%) and PEGTA (2%) conjugated with lam-IKVAV (100 µM) and our novel IKVAV peptide of different concentrations of 0, 10, 50, and 100 µM. (A) The gelation time (when G'=G") is determined by time sweep. (B) At 2 h, the hydrogel is with G' of 600 Pa. (C) Frequency sweep shows the hydrogel is stable at 2 h.

FIGS. 22A1-22D3. Human NPCs cultured on the surface of hydrogels conjugated with (A) lam-IKVAV (100 µM) and our novel IKVAV peptide at different concentrations of (B) 0, (C) 10, and (D) 100 µM at the day (1) 1, (2) 3, and (3) 7. Scale bar=100 µm.

FIG. 23A-23D. Immunostaining of hNPCs cultured on the surface of hydrogels conjugated with (A) lam-IKVAV (100 µM) and our novel IKVAV peptide of different concentrations of (B) 0, (C) 10, and (D) 100 µM at the day 7. Cells were stained with DAPI for nuclei (blue), and phalloidin for actin (red). Scale bar=100 µm.

Figure 24:
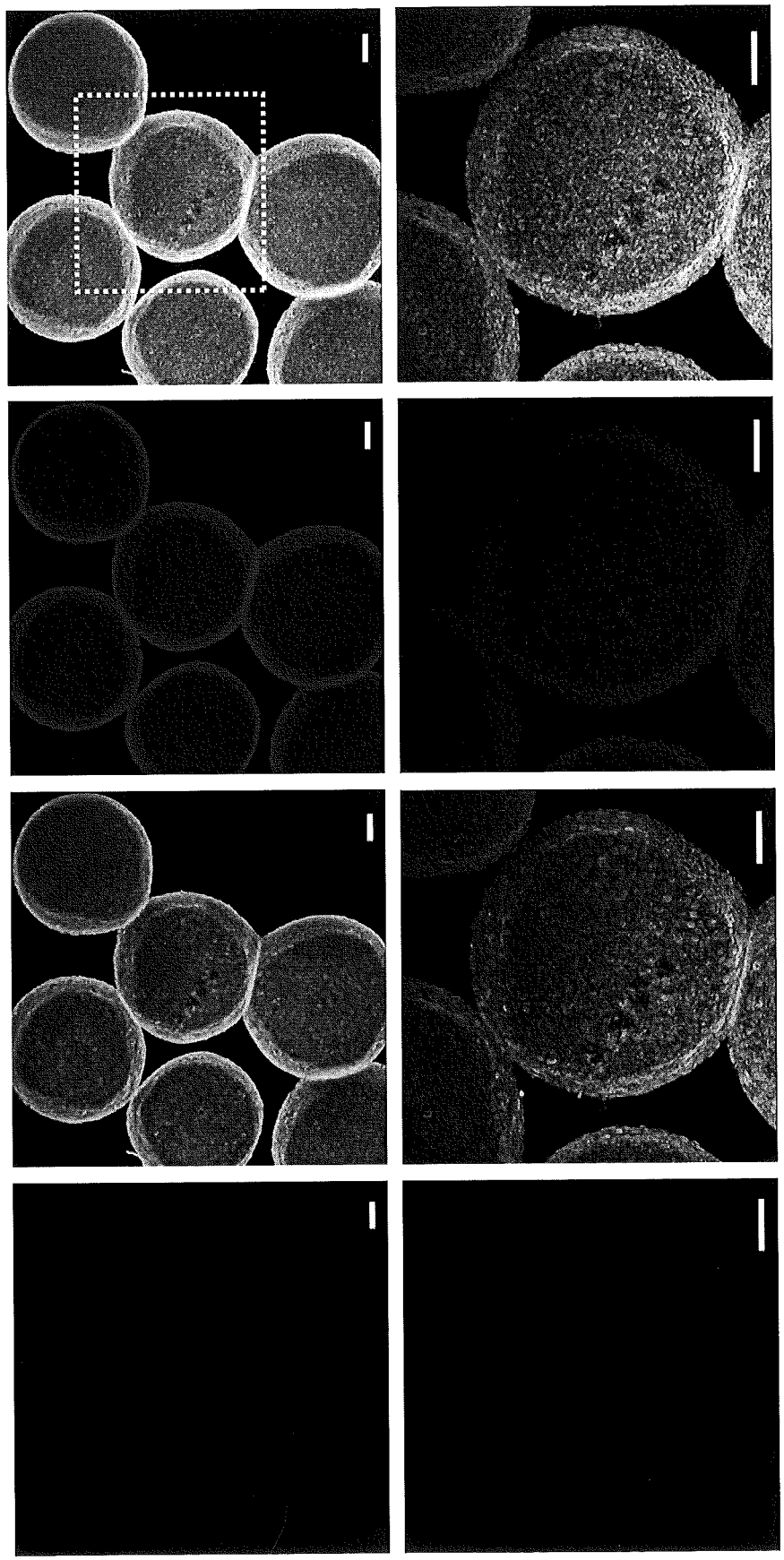
Figures 25A, 25B, 25C, 25D, 25E:
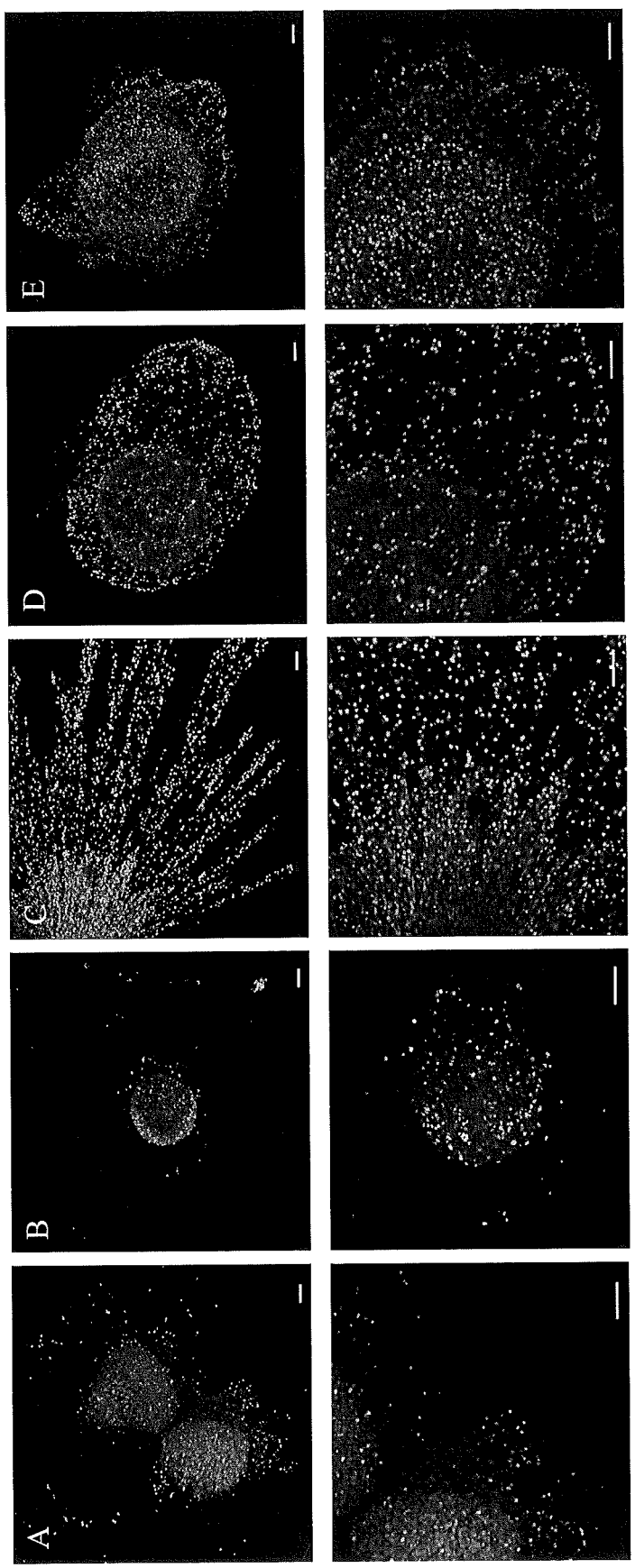

FIG. 24. Immunostaining of hNeurospheres with uniform size of 400 µm. Cells were stained with DAPI (blue), nestin (green), and human mitochondria (red). Scale bar=100 µm.

FIG. 25A-25E. Human neurospheres survived inside hydrogels conjugated with (A) lam-IKVAV (100 µM) and our novel IKVAV peptide of different concentrations of (B) 0, (C) 10, (D) 50, and (E) 100 µM at the day 21. Bottom panel shows the lager review of neurospheres inside hydrogels. Cells were stained with LIVE/DEAD (Green/Red) kit. Scale bar=100 µm.

Figure 26:
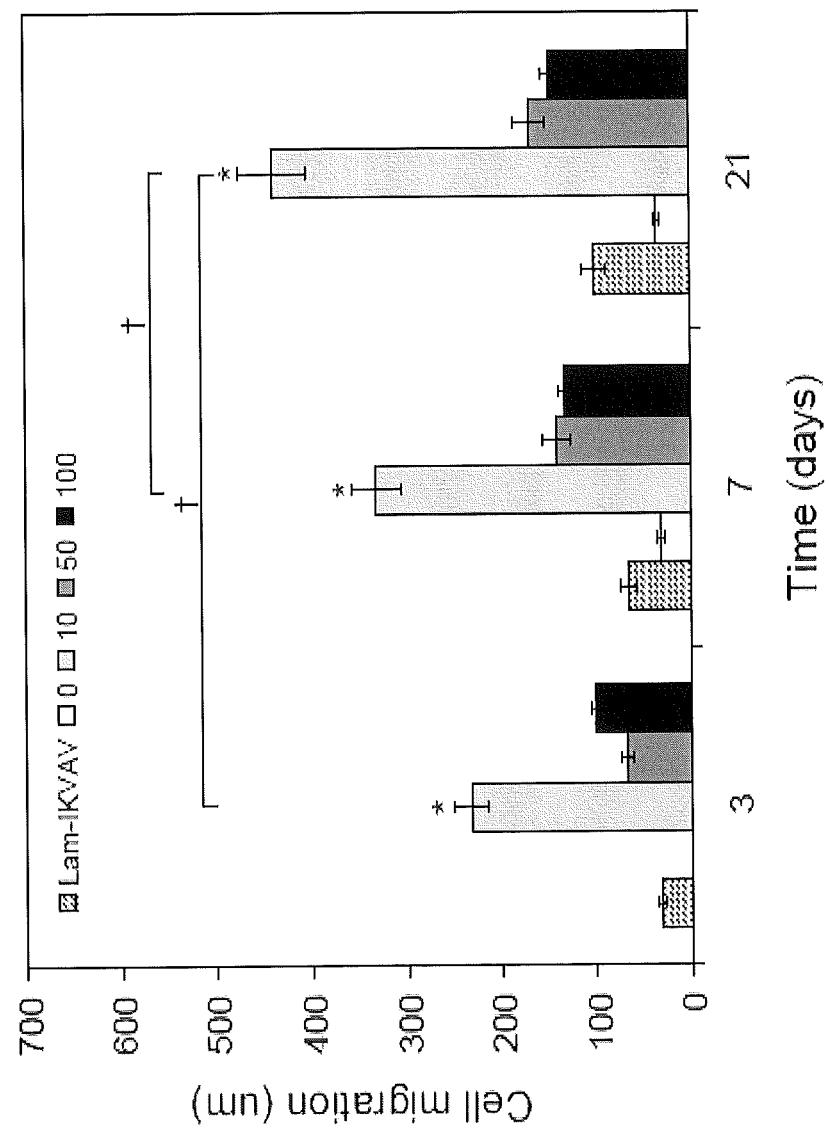

FIG. 26. Quantification of cell migration from human neurospheres cultured inside hydrogels conjugated with lam-IKVAV (100 µM) and our novel IKVAV peptide of different concentrations of 0, 10, 50, and 100 µM at the day 3, 7, and 21. A greater number of neurite outgrowth was seen in the hydrogels conjugated with our peptide at 10 µM than other concentrations at all the day 3, 7, and 21 (*p<0.05). Migration of cells was statistically significant as a function of time (†p<0.05).

FIG. 27A-27D. Human neurospheres cultured inside hydrogels conjugated with our novel IKVAV peptide (10 µM) at the day (A) 1, (B) 3, (C) 7, and (D) 21. (D and D') The same field of view in two different planes of focus showing hNeurospheres encapsulated in hydrogels at the day 21. Scale bar=100 µm.

FIG. 28A-28B. Scheme of (A) lam-IKVAV peptide and (B) our novel IKVAV conjugated to gold-coated cover slips.

FIG. 29A-29B. Morphology of (A) lam-IKVAV peptide and (B) our novel IKVAV conjugated to gold-coated cover slips by atomic force microscope.

DETAILED DESCRIPTION OF THE INVENTION

The present invention will now be described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

Unless indicated otherwise, explicitly or by context, the following terms are used herein as set forth below.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of 20%, 10%, 5%, 1%, 0.5%, or even 0.1% of the specified amount.

An "effective" amount as used herein is an amount of a composition of this invention that provides some improvement or benefit to the subject. Alternatively stated, an "effective" amount is an amount that provides some revascularization, reenervation, repopulation, recruitment, treatment, etc. Those skilled in the art will appreciate that such effects need not be complete or curative, as long as some benefit is provided to the subject.

By the terms "treat," "treating" or "treatment of," it is intended that the severity of the patient's condition is reduced or at least partially improved or modified and that some alleviation, mitigation or decrease in at least one clinical symptom is achieved.

The terms "increase," "increasing," "increased," (and grammatical variations thereof), as used herein, describe an elevation in the cell adhesion, stable attachment and/or proliferation of cells by contacting the cells with a hydrogel or stem cell platform of the invention. This increase in cell adhesion, stable attachment and/or proliferation of cells can be observed by comparing the cell adhesion, stable attachment and/or proliferation of cells not contacted with a hydrogel or stem cell platform of the invention of the invention. Thus, as used herein, the terms "increase," "increasing," "increased," (and grammatical variations thereof), and similar terms indicate an elevation of at least about 5%, 10%, 15%, 20%, 25%, 30%, 35%, 40%, 45%, 50%, 55%, 60%, 75%, 80%, 85%, 90%, 95%, 100%, 150%, 200%, 300%, 400%, 500% or more as compared to a control (e.g., a cell that is not contacted with a hydrogel of the invention and/or stem cell platform of the invention).

As used herein, the term "in-situ crosslinkable hydrogel" describes a hydrogel of this invention in which the gelation process can occur at a local tissue site. The material components of the hydrogel can be injected into a local tissue site in the form of liquid precursors, and gelation starts at the local tissue site right after and/or simultaneously with the injection. The gelation normally occurs in the presence of crosslinkers, and it is accelerated at elevated temperatures (such as at body temperatures when compared to room temperature). To control the gelation in situ, the crosslinker is mixed into the liquid precursors right before the injection so that gelation starts right after the injection. The concentration of the crosslinker in the material also determines the length of time necessary for the gelation to be completed at the tissue site.

As used herein, the term "preventing scar tissue growth in a CNS lesion" refers to any activity that effectively inhibits the growth of scar tissue in a CNS lesion, e.g., an inhibition of about 10%, 20%, 30%, 40%, 50%, 60%, 70%, 80%, 90%, 95%, or more. Those skilled in the art will appreciate that such inhibition need not be complete, as long as scar tissue growth is inhibited, e.g., in an amount that can be detected and or measured.

As used herein, the term "an agent that blocks the biosynthesis of inhibitory ECM components" refers to any molecule or compound that inhibits the biosynthesis of one or more of the molecules that comprise the ECM of scar tissue normally found in or around CNS lesion sites, e.g., an inhibition of about 10%, 20%, 30%, 40%, 50%, 60%, 70%, 80%, 90%, 95%, or more. ECM components are known to those of skill in the art, and include (but are not limited to) collagen IV and chondroitin sulphate proteoglycans. Exemplary agents include p-nitrophenyl-b-D-xylopyranoside (PNPX) and prolyl hydroxylase inhibitors (PHIs), such as ethyl-3,4 dihydroxybernoate (EDHB) and dimethyloxalylglycine (DMOG).

As used herein, the term "an agent that reduces recruitment of an inflammatory response" or "reduces activity of inflammatory cells" refers to a molecule or compound that blocks or interferes with the migration or movement of cells that are involved in an inflammatory response (e.g., macrophages, neutrophils, astrocyes, etc.) to the lesion site and/or inhibits or interferes with the activity of inflammatory cells such that inflammation at the lesion site is reduced or inhibited. A reduction in recruitment and/or a reduction in activity as described herein can be about 10%, 20%, 30%, 40%, 50%, 60%, 70%, 80%<90% OR 100% as compared to the amount of recruitment or activity that would be present in the absence of said molecule or compound. Nonlimiting examples of such molecules or compounds include methylprednisone, dexamethasone, erythropoietin, minocyclin, progesterone, estrogen, anti CD-11 antibodies, magnesium sulfate, riluzole, polyethylene glycol, atorvastatin, ionosin, pioglitazone, chondrotinase ABC, anti Nogo antibodies and any combination thereof.

As used herein, the term "ECM-degrading enzyme" refers to any enzyme that promotes the breakdown and/or digestion of one or more molecules that comprise the ECM of scar tissue normally found in or around CNS lesion sites. Exemplary ECM-degrading enzymes include collagenase IV and chondroitinase ABC ($Ch^{ase}ABC$).

As used herein, the term "scar-reduced environment" refers to any environment that is substantially lacking glial scar tissue. An environment is substantially lacking glial scar tissue when less than about 20%, e.g., less than about 15%, 10%, 5%, or 1% of the total volume of the environment is occupied by glial scar tissue. Methods of measuring the total volume of a CNS lesion are known to those of skill in the art.

As used herein, the term "neural stem cell recruiting factor" refers to any molecule that promotes the attraction and/or proliferation of neural stem cells. In one embodiment, neural stem cell recruiting factors are naturally occurring proteins or active fragments or analogs thereof. Such factors include, but are not limited to, hepatocyte growth factor (HGF), insulin-like growth factor 1 (IGF-1), fibroblast growth factor 2 (FGF-2), platelet-derived growth factor (PDGF), gliotropic factors (Human recombinant annexin A2), stem cell factor-1, stromal cell-derived factor-1 (SDF-1), chemokine monocyte chemoattractant protein-1 (MCP-1, SCYA2, CCL2, MCAF), vascular endothelial growth factor (VEGF), epidermal growth factor (EGF), transmembrane protein 18 and glioma-produced ECM (tenascin-C). In other embodiments, the factor may be a small molecule, e.g., less than about 1000 Da, less than about 2000 Da, less than about 3000 Da, less than about 4000 Da less than about 5000 Da, less than about 6000 Da, less than about 7000 Da, less than about 8000 Da, less than about 9000 Da or less than about 10,000 Da.

As used herein, the term "neural differentiation factor" refers to any molecule that promotes the differentiation of neural stem cells and their precursors into neurons and/or glia. Such factors include, but are not limited to, nerve growth factor (NGF), brain-derived neurotrophic factor (BDNF), neurotrophin-3 (NT-3), neurotrophin-4 (NT-4), novel neurotrophin-1 (NNT-1), glial-cell-line-derived neurotrophic factor (GDNF), and conserved dopamine neurotrophic factor (CNTF).

As used herein, the term "neural stem cell mobilizing factor" refers to any molecule that promotes the motility of neural stem cells. Such factors include, but are not limited to, leukemia inhibitory factor (LIF) and granulocyte-colony stimulating factor (G-CSF).

I. Revascularization

Previous reports have implicated the crucial role of vasculature in inducing, supporting, and sustaining neurogenesis, neuronal survival, and brain architecture, which are fundamental for brain tissue regeneration (Ohab et al. *J. Neurosci.* 26:13007 (2006); Leventhal et al., *Mol. Cell, Neurosci.* 13:450 (1999)). Thus, reconstructing the damaged vasculature network within a CNS lesion is a fundamental step in alleviating tissue injury and promoting brain tissue regeneration.

In designing therapeutic strategies to reconstruct the damaged vasculature network of a CNS lesion, one must seek to minimize the surgical trauma to the brain tissue during the implantation procedure to protect healthy brain tissue and the integrity of the blood-brain barrier. For this purpose, biopolymer liquid precursors that are able to undergo in situ polymerization to form scaffolds that conform to the irregular dimensions of the lesion site without producing toxic residues are highly desirable.

To that end, the present invention comprises, consists essentially of, or consists of an in-situ crosslinkable hydrogel that acts as a substrate to promote angiogenesis and neural regeneration. In general, embodiments of the present invention comprise a hydrogel with mechanical properties similar to those of native CNS tissue (~10-40 Pa) and cell adhesion motifs. Most importantly, the hydrogel of the present invention is able to undergo in situ gelation in CNS tissue, allowing it to conform to the irregular dimensions of the CNS lesion.

In some embodiments of the present invention, the in-situ crosslinkable hydrogel comprises at least one synthetic or ECM molecule; in other embodiments, the hydrogel comprises at least two different synthetic or ECM molecules. The synthetic molecule(s) or ECM molecule(s) may be chemically modified, such as by the addition of thiol groups or acrylate groups.

In some embodiments, the hydrogel of this invention can comprise, consist essentially of or consist of a hydrophilic component and an adhesive component. The hydrophilic component can comprise, consist essentially of or consist of, e.g., a polyalkylene glycol (PAG) (e.g., polyethylene glycol (PEG)), hyaluronic acid, chitosan and any combination thereof. The adhesive component of the hydrogel can comprise, consist essentially of or consist of gelatin, collagen, laminin, fibronectin, vitronectin and any combination thereof. Any of the components of the hydrogel of this invention can be thiolated (e.g., thiolated hyaluronic acid, thiolated gelatin, thiolated collagen, thiolated fibronectin, thiolated vitronectin, thiolated laminin, thiolated chitosan, thiolated PEG, thiolated heparin, etc.) or any of the components of the hydrogel can be non-thiolated, in any combination of thiolated and nonthiolated components. The molar ratio of hydrophilic component to adhesive component in the hydrogel can be from about 500:1 to about 1:500, including any ratio between these values not explicitly recited here (e.g., 300:1, 100:1, 50:1, 1:250, 1:100, etc.). The weight ratio of the hydrophilic component to adhesive component in the hydrogel can be from about 1500:1 to about 1:1500, including any ratio between these values not explicitly recited here (e.g., 1300:1, 1000:1, 1:1000, etc.) In some embodiments in which hyaluronic acid or thiolated hyaluronic acid is included in the hydrogel, it can be present in a range of about 2% to about 25% (e.g., about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%) of the weight of the hydrogel.

The hydrogel of the present invention may comprise any extracellular matrix molecule, including one or more of hyaluronic acid, collagen, heparin, laminin, gelatin, fibronectin, dextran, and/or chitosan. In certain embodiments, the hydrogel comprises both hyaluronic acid and collagen. In a still more preferred embodiment, the ratio of hyaluronic acid to collagen, laminin, chitosan or gelatin can range from about 15:1 to about 1:15 (including e.g., a range of about 10:1 to about 1:10; a range of about 5:1 to about 1:5, a range of about 3:1 to 1:3). In one embodiment, the ratio of hyaluronic acid to collagen is about 1:3. In further embodiments, the hydrogel may comprise hyaluronic acid, collagen, and laminin. In yet further embodiments the hydrogel may comprise hyaluronic acid and gelatin in any of the ratios described herein. In some embodiments, the hydrogel can comprise chitosan and gelatin in any ratios described herein.

The hydrogel of the present invention may also comprise any types of polyethylene glycol (PEG), including one arm PEG or multi-arm PEG. PEG may have thiol groups or acrylate groups. The hydrogel of the present invention may comprise any types of ECM derived short peptide sequences, including short peptides from collagen, laminin, gelatin, fibronectin, vitronectin, and so on. In certain embodiments, the hydrogel comprises both PEG and peptide sequence(s). In a still further embodiment, the ratio of PEG to peptide sequence ranges from about 10:1 to about 1:10 (including e.g., about 5:1 to about 1:5 or about 3:1 to about 1:3). In one embodiment, the ratio of PEG to peptide sequence is about 1:3.

In some embodiments, the hydrogel of the present invention promotes angiogenesis in a CNS lesion without using angiogenic growth factors. Thus, in one embodiment, the hydrogel does not comprise any angiogenic growth factors. In other embodiments, the hydrogel does comprise angiogenic growth factors. Angiogenic growth factors include, without limitation, VEGF and PDGF.

A lesion of this invention can be but is not limited to, a lesion in the brain, a lesion in the spinal cord, a lesion due to ischemia, a lesion due to hemorrhage, a lesion due to stroke, a lesion due to traumatic brain injury, a lesion due to anoxic brain injury, a lesion due to acute spinal cord injury, a lesion due to chronic spinal cord injury and a lesion due to multiple sclerosis, as well as any combinations thereof.

In some embodiments, the hydrogel of this invention can comprise, consist essentially of or consist of at least one synthetic molecule or ECM molecule. In other embodiments, the hydrogel can comprise, consist essentially or of consist of at least two (e.g., 2, 3, 4, 5, 6, 7, 8, 9, 10, etc.) different synthetic molecules or ECM molecules. Such synthetic or ECM molecules can be chemically modified, and/or can be thiolated and/or acrylated. In some embodiments, the hydrogel of this invention can comprise hyaluronic acid, collagen, heparin, laminin, gelatin, polyethylene glycol (in some embodiments with up to 10 arms), and/or thiolated peptide sequences as well as any combination thereof. In certain embodiments, the hydrogel of this invention comprises hyaluronic acid and collagen. In some embodiments, the ratio of hyaluronic acid to collagen can range from about 10:1 to about 1:10 (e.g., 9:1, 8:1, 7:1, 6:1, 5:1, 4:1, 3:1, 2:1, 1:1, 1:2, 1:3, 1:4, 1:5, 1:6, 1:7, 1:8, 1:9, 1:10). In particular embodiments, the ratio of hyaluronic acid to collagen ranges from about 5:1 to about 1:5 and in more particular embodiments, the ratio of hyaluronic acid to collagen is about 1:3. In other embodiments, the hydrogel can comprise hyaluronic acid, collagen and laminin. In other embodiments, the hydrogel can comprise hyaluronic acid and gelatin in any of the ratios described herein.

In particular embodiments, the hydrogel of this invention can comprise, consist essentially of, or consist of chitosan and gelatin. The chitosan:gelatin ratio in the hydrogel can be from about 0.5:15 to about 15:0.5 (e.g., about 0.5:15, 1:15, 2:15, 3:15, 4:15; 5:15, 6:15, 7:15, 8:15, 9:15; 10:15, 11:15, 12:15, 13:15, 14:15, 15:14, 15:13, 15:12, 15:11, 15:10, 15:9, 15:8, 15:7, 15:6, 15:5, 15:4, 15:3, 15:2, 15:1, 15:0.5, etc.). In some embodiments, the chitosan:gelatin ratio can be about 6:4.

In some embodiments, the hydrogel of this invention does not comprise any angiogenic factors. In some embodiments, the hydrogel can comprise at least one neural stem cell recruiting factor, which can be, e.g., hepatocyte growth factor. In some embodiments, the hydrogel can comprise at least one mitogen (e.g., proliferating factor). In further embodiments, the hydrogel of this invention can comprise at least one neural differentiation factor, which can include but is not limited to BDNF, NT-3, GDNF and CNTF, singly or in any combination.

Some embodiments of the methods of this invention include the step comprising delivering at least one neural stem cell mobilizing factor to the CNS of a subject on whom the methods are being carried out. In particular embodiments, the neural stem cell mobilizing factor can be leukemia inhibitory factor and in some embodiments, the neural stem cell mobilizing factor can be delivered to the subventricular zone. The present invention also encompasses in the methods herein the further step comprising delivering a neural stem cell recruiting factor to a lesion site and delivering a neural stem cell mobilizing factor to the subventricular zone. In the methods described herein, the neural stem cell recruiting factor can be hepatocyte growth factor and the neural stem cell mobilizing factor can be leukemia inhibitory factor.

In the methods of this invention, the factor, agent or enzyme can be present in the hydrogel and/or can be loaded into nanoparticles, microparticles, liposomes, membranes, scaffolds and/or micelles, in any combination. Such nanoparticles, microparticles liposomes, membranes, scaffolds and/or micelles can be biodegradable. In particular embodiments, a nanoparticle of this invention can comprise PLGA or the nanoparticle can be any degradable polymer.

In some embodiments, the hydrogel, nanoparticle, microparticle, liposome, membrane, scaffold and/or micelle of this invention can comprise cells and/or constructs and/or implants, nonlimiting examples of which include neural stem cells, embryonic stem cells, olfactory ensheathing cells, neural progenitor cells, neural stem cell derived precursor cells, fibroblasts, bone marrow derived stem cells, dorsal root ganglion, axonal constructs, peripheral nerve implants, Schwann cells and any combination thereof. In some embodiments, the cells are human cells (e.g., human stem cells, human neuronal cells, and the like). These cells, constructs and/or implants are added to, positioned in or on and/or incorporated into the vehicle of this invention prior to delivery, contact or administration of the vehicle to a subject. In other embodiments, the hydrogel, nanoparticle, microparticle, liposome, membrane, scaffold and/or micelle of this invention can be devoid of cells or devoid of particular types of cells (e.g., as exemplified herein) prior to delivery, contact or administration of the hydrogel, nanoparticle, microparticle, liposome, membrane, scaffold and/or micelle to the subject.

In some embodiments, the hydrogel of this invention is designed for sustained release of the factor, agent and/or enzyme. The hydrogel can be designed for sustained release of an effective amount of the factor, agent and/or enzyme for at least 5 days, at least 30 days or at least 60 days.

In the methods described herein for preventing scar tissue growth at a CNS lesion, or maintaining a scar reduced environment in a CNS lesion, the agent that blocks the biosynthesis of inhibitory ECM components can be but is not limited to p-nitrophenyl-b-D-xylopyranoside, dimethyloxalylglycine, cyclic nucleotides, and combinations thereof.

In the methods described herein for digesting scar tissue growth in a CNS lesion or maintaining a scar reduced environment in a CNS lesion, the ECM degrading enzyme can be but is not limited to chondroitinase ABC, collagenase IV, and combinations thereof.

In some methods of this invention, a pure synthetic hydrogel, a extracellular matrix (ECM) based hydrogel, a chemically modified ECM based hydrogel, or a mixture of synthetic and ECM based hydrogels can be used.

In some embodiments of the foregoing, the ECM-based hydrogel comprises at least one ECM molecule. In other embodiments, the hydrogel comprises at least two different ECM molecules. Said ECM molecule(s) may be chemically modified, such as by the addition of a thiol group. In some embodiments, the hydrogel may comprise hyaluronic acid, collagen, heparin, laminin, gelatin, fibronectin, and/or chitosan. In certain embodiments, the hydrogel comprises both hyaluronic acid and collagen. In other embodiments, the ratio of hyaluronic acid to collagen ranges from about 10:1 to about 1:10, e.g., about 1:3. Further embodiments may comprise hyaluronic acid, collagen, and laminin. In certain embodiments, the hydrogel comprises both hyaluronic acid and gelatin. In other embodiments, the ratio of hyaluronic acid to gelatin ranges from about 10:1 to about 1:10, e.g., about 1:3. Further embodiments may comprise hyaluronic acid, gelatin, and laminin. Poly(ethylene glycol)tetra-acrylate (PEGTA) or PEGDA can be used as crosslinker for gelation. The concentration of PEGTA or PEGDA can be from about 0.01% to about 20%.

In some embodiments of the foregoing, the hydrogel comprises at least one synthetic molecule. In other embodiments, the hydrogel comprises at least two (e.g., 3, 4, 5, 6, 7, 8, 9, 10, etc.) different synthetic molecules. The synthetic molecule(s) may be chemically modified, such as by the addition of one or more thiol groups or acrylate groups. In some embodiments, the hydrogel may comprise polyethylene glycol (PEG), also known as polyethylene oxide (PEO). In some embodiments, the hydrogel of this invention can comprise, consist essentially of or consist of synthetic peptide sequences (e.g., laminin peptide sequences, fibronectin peptide sequences, vitronectin peptide sequences, collagen peptide sequences, etc.), which can be thiolated (e.g., thiolated laminin peptide sequence, thiolated fibronectin peptide sequence, vitronectin peptide sequence, thiolated collagen peptide sequence). In certain embodiments, the hydrogel comprises, consists essentially of or consists of thiolated PEG and thiolated laminin peptide sequence(s). In other embodiments, the ratio of thiolated PEG to thiolated peptide sequence can range from about 1500:1 to about 1:1500, e.g., about 1:3, 1:100, 1:500; 1:1300, 1300:1, 500:1, 100:1, 3:1, etc. Further embodiments may comprise thiolated PEG and/or one or more (e.g., 2, 3, 4, 5, 6, 7, 8, 9, 10, etc.) of a thiolated peptide sequence from fibronectin, vitronectin, laminin, collagen etc. PEG can be single arm to multi-arm (e.g., 1, 2, 3, 4, 5, 6, 7, 8, 9, or 10 arms). Poly(ethylene glycol)tetra-acrylate (PEGTA) or PEGDA can be used as crosslinker for gelation. The concentration of PEGTA or PEGDA in the hydrogel can be from about 0.01% to about 20% (e.g., 1.0%, 0.5%, 1.0%, 2.0%>3.0%, 4.0%>5.0%, 6.0%, 7:0%, 8:0%, 9.0%, 10%, 11%, 12%, 13%, 14%, 15%, 16%, 17%, 18%, 195, 20%).

Nonlimiting examples of laminin peptides of the invention include CCRRIKVAVWLC (SEQ ID NO:1), CCRRYVVLPRWLC (SEQ ID NO:3), CCRRNIAEIIKDIWLC (SEQ ID NO:4), CCRRYIGSRWLC (SEQ ID NO:5), CDPVCCGTARPGYIGSRGTARCCAC (SEQ ID NO:6), CDPVCCGTARPGNIAEIIKDIGTARCCAC (SEQ ID NO:7), CDPVCCGTARPGYVVLPRGTARCCAC (SEQ ID NO:8), CDPVCCGTARPGIKVAVGTARCCAC (SEQ ID NO:9) and any combination thereof. Nonlimiting examples of fibronectin peptides of the invention include CCRRGRGDSPKWLC (SEQ ID NO:10), CCRRAVTGRGDSPASSWLC (SEQ ID NO:11), CDPVCCGTARPGPQVTRGDVFTMPGTARCCAC (SEQ ID NO:12), CDPVCCGTARPGRGDGTARCCAC (SEQ ID NO:13) and any combination thereof. A nonlimiting example of a vitronectin peptide of this invention includes CCRRPQVTRGDVFTMPWLC (SEQ ID NO:14). Any or all of these peptides can be thiolated peptides.

In some embodiments of this invention, the hydrogel comprises at least one synthetic molecule and one ECM. In other embodiments, the hydrogel comprises two or more (e.g., 2, 3, 4, 5, 6, 7, 8, 9, 10, etc.) different synthetic molecules and two or more (e.g., 2, 3, 4, 5, 6, 7, 8, 9, 10, etc.) ECMs. The synthetic molecule(s) or ECM(s) may be chemically modified, such as by the addition of one or more thiol groups or acrylate groups. In some embodiments, the hydrogel may comprise polyethylene glycol, synthetic peptide sequences, hyaluronic acid, and gelatin. In certain embodiments, the hydrogel comprises both thiolated PEG, thiolated laminin short peptide sequences, thiolated hyaluronic acid, and thiolated gelatin. In other embodiments, the ratio of thiolated PEG: thiolated peptide sequence: thiolated hyaluronic acid: thiolated gelatin ranges from about 10:1:1:1 to about 1:1:1:10, e.g., about 4:3:2:1. Further embodiments may comprise thiolated PEG, thiolated peptide sequence from fibronectin, etc. PEG can be single arm to multi-arm (e.g., 1-10 arms). Poly(ethylene glycol)tetra-acrylate (PEGTA) or PEGDA can be used as crosslinker for gelation. The concentration of PEGTA or PEGDA can be from about 0.01% to about 20%.

In some embodiments of the present invention, the factor, agent, and/or enzyme present in the hydrogel is loaded into nanoparticles (e.g., biodegradable nanoparticles), lipsomes, micelles or any combination thereof.

In some embodiments of the present invention, the hydrogel is designed for sustained release of the factor, agent, and/or enzyme present therein. In certain embodiments, the hydrogel releases an effective amount of the factor, agent, and/or enzyme for at least about 5 days, e.g., at least about 10 days, at least about 15 days, at least about 20 days, at least about 25 days, at least about 30 days or at least about 60 days.

One of skill in the art will appreciate that the factors, agents, and enzymes discussed above with relation to certain embodiments of the present invention may likewise be included in alternate embodiments of the claimed invention. Indeed, particular embodiments of the claimed invention may incorporate factors, agents, and enzymes from each of the aforementioned categories: neural stem cell recruiting factors, neural stem cell proliferation factors, neural stem cell differentiation factors, neural stem cell mobilization factors, agents that block the biosynthesis of inhibitory ECM components, and ECM-degrading enzymes.

II. Reenervation

For the ultimate repair following cerebral stroke, neuronal and glial repopulation of the cranial lesion cavity is important. An example of a cell source for neural replacement includes endogenous neural stem cells (NSCs). These cells normally reside in the forebrain subventricular zone (SVZ)-olfactory bulb pathway in adult mammalian brain, and are able to generate neurons and glia throughout life (Gage, *Science* 287:1433 (2000)). Accumulating evidence indicates the ability of SVZ-endogenous NSCs/precursors to proliferate and migrate to areas of ischemic injury in adult brain (Jin et al., *Mol. Cell. Neurosci.* 24:171 (2003); Parent, *Neuroscientist* 9:261 (2003)). Further, NSCs are able to form appropriate neural cell types to replace damaged neurons and glia cells (Arvidsson et al., *Nature Med.* 8:963 (2002); Parent et al., *Ann. Neurol.* 52:802 (2002), suggesting that the manipulation of endogenous NSCs may be a potential strategy for brain stroke repair.

Thus, embodiments of the present invention comprise, consist essentially of, or consist of a method of delivering an in-situ crosslinkable hydrogel that contains a neural stem cell recruiting factor, mitogen/proliferation factor, and/or neural differentiation factor to the lesion in an amount effective to promote both revascularization of the lesion and recruitment of neural stem cells to the lesion. In certain embodiments, the hydrogel contains at least one neural stem cell recruiting factor and/or at least one neural differentiation factor. Neural stem cell recruiting factors suitable for use in the present invention include, but are not limited to, HGF, LIF, IGF-1, SDF-1, FGF-2, and PDGF. Neural differentiation factors suitable for use in the present invention include, but are not limited to, BDNF, NT-3, GDNF, and CNTF.

Further embodiments of the claimed invention comprise supplementing the delivery of a revascularization-promoting amount of an in-situ crosslinkable hydrogel with the delivery of a neural stem cell mobilizing factor to the CNS. In certain embodiments, the neural stem cell mobilizing factor is delivered to the subventricular zone. In other embodiments, the neural stem cell mobilizing factor can be, e.g., LIF and/or G-CSF.

Additional embodiments of the claimed invention comprise a method of delivering an in-situ crosslinkable hydrogel to a lesion in an amount effective to promote revascularization of the lesion, and delivering both a neural stem cell recruiting factor and a neural stem cell mobilizing factor to the CNS. In certain embodiments, at least one neural stem cell recruiting factor is present in the hydrogel and at least one neural stem cell mobilizing factor is delivered to the subventricular zone. In other embodiments, the neural stem cell recruiting factor is HGF and the neural stem cell mobilizing factor is LIF.

In some embodiments, the present invention provides a method of increasing cell adhesion, stable attachment and/or proliferation of cells in a hydrogel, comprising: contacting cells with a hydrogel of the invention, wherein the hydrogel is conjugated to peptides of the invention (e.g., peptides having the amino acid sequence of SEQ ID NOs:1-27); and culturing the cells, wherein the cells have increased cell adhesion, stable attachment and proliferation as compared to a control (cells contacted with a hydrogel that is not conjugated to peptides of this invention such as a hydrogel comprising laminin-IKVAV peptide, CSRARKQAASIKVAVSADR). In representative embodiments, the peptide of the invention conjugated to the hydrogel comprises, consists essentially of, consists of the amino acid sequence of CCRRIKVAVWLC (SEQ ID NO:15). As described herein, the cells can be any cell type useful with this invention including but not limited to stem cells, neural stem cells, embryonic stem cells, olfactory ensheathing cells, neural progenitor cells, neural stem cell derived precursor cells, fibroblasts, bone marrow derived stem cells, Schwann cells and the like or any combination thereof In other embodiments of the invention, a method of promoting differentiation of neural stem cells in neurons is provided, the method comprising: contacting neural stem cells with a hydrogel of the present invention, wherein the hydrogel is conjugated to peptides of the invention (e.g., peptides having the amino acid sequence of SEQ ID NOS:1-14); and culturing the cells, wherein the differentiation of the cells into neurons is promoted compared to a control (e.g., neural stem cells contacted with a hydrogel that is not conjugated to peptides of this invention such as a hydrogel comprising laminin-IKVAV peptide, CSRARKQAASIKVAVSADR, SEQ ID NO:15). In a representative embodiments, the peptide of the invention conjugated to the hydrogel comprises, consists essentially of, or consists of the amino acid sequence CCRRIKVAVWLC (SEQ ID NO:1).

In still other embodiments, a method for increasing neuronal stem cell migration from neurospheres cultured inside hydrogels is provided, the method comprising: contacting neural stem cells with a hydrogel of the invention and producing neurospheres in the hydrogel, wherein the hydrogel is conjugated to peptides of the invention (e.g., peptides having the amino acid sequence of SEQ ID NOS:1-14) and the migration of the neuronal stem cells from the neurospheres is increased as compared to a control (e.g., neural stem cells contacted with a hydrogel that is not conjugated to peptides of this invention such as a hydrogel comprising laminin-IKVAV peptide, CSRARKQAASIKVAVSADR, SEQ ID NO:15). In representative embodiments, the peptide of the invention conjugated to the hydrogel comprises, consists essentially of, or consists of the amino acid sequence of CCRRIKVAVWLC (SEQ ID NO:1).

In further embodiments, the epitope density of a hydrogel of the invention conjugated to peptides of the invention can be amplified at least 10 times (e.g., 10, 15, 20, 25, 30, 35, 40, 45, 50 times or more) as compared to the epitope density of a laminin monolayer. Thus, in particular embodiments, the epitope density of a hydrogel of the invention conjugated to peptides comprising, consisting essentially of, or consisting of the amino acid sequence of SEQ ID NO:1 can be amplified at least 10 times (e.g., 10, 15, 20, 25, 30, 35, 40, 45, 50 times or more) as compared to the epitope density of a laminin monolayer.

III. Scar Tissue

A detailed characterization of the cellular and biomolecular sequelae arising from ischemic stroke has led to the recognition of the predominant role of the dense ECM-rich scar tissue that forms at the lesion site in inhibiting brain tissue regeneration. Following acute focal ischemic stroke, cells undergo two major modes of deaths: necrosis, and apoptosis (Lipton, *Physiol. Rev.* 79:1431 (1999)). While necrosis is more common in the core tissue, penumbral cells that are located centrifugally from the core may undergo either mode of death. Accompanying the cell deaths, the infarcted region starts to lose structural integrity in a radial fashion from the core to the penumbra. Injured neurons and activated inflammatory cells, such as microglia, macrophages, and reactive astrocytes, may release toxic mediators at the lesion site, which amplify tissue damage (Trendelenburg et al., *Glia* 50:307 (2005)). Scattered dead neurons in the ischemic core are initially seen after 10 to 20 minutes, followed by the actual infarct formation at about 1 hour. Eventually (beyond 1-2 weeks), persistent cell dysfunction and poor neural regenerative capabilities at the ischemic core and beyond lead to the formation of a cystic cavity encapsulated in a dense layer of glial scar tissue (Lipton, *Physiol. Rev.* 79:1431 (1999)).

Scar tissue, which consists primarily of reactive astrocytes and proteoglycans (Lindsay, Reactive gliosis. In: Fedoroff S, Vernadakis A, editors. Astrocytes. Orlando: Academic Press; 1986. p 231-262), acts as a major physical barrier for brain tissue regeneration across the lesion and the structural and functional integration of the regenerating tissue with existing neural circuitry (Lipton, *Physiol. Rev.* 79:1431 (1999); Gartshore et al., *Exp. Neurol.* 147:353 (1997)). In addition, scar tissue may serve as a diffusion barrier, obstructing the delivery of pharmacological agents and the transport of oxygen and nutrients to cells implanted within the lesion cavity.

In the acute and subacute stages of stroke, inflammatory cells travel from the vasculature into the ischemic region, and interact to form a dense structure known as a glial scar. The response of astrocytes to injury is characterized by hypertrophy and hyperplasia (Barrett et al., *Exp. Neurol.* 84:374 (1984)), accompanied by an increased production of intermediate filaments (such as GFAP (Bignami et al., *J. Comp. Neurol.* 153:27 (1974); Eng, *J. Neuroimmunol.* 8:203 (1985)) and vimentin (Yang et al., *Mol. Chem. Neuropathol.* 21:155 (1994))). In addition, astrocytes—along with other CNS-resident cells, such as microglia and oligodendrocytes, and hematogenous cells, like macrophages—play a role in the regulation of ECM production after CNS injury (Fitch et al., *J. Neurosci.* 19:8182 (1999); Preston et al., *J. Neurotrauma* 18:83 (2001)). The resulting ECM contains several classes of molecules that are inhibitory to brain tissue regeneration, including proteoglycans (Gallo et al., *Exp. Cell Res.* 187:211 (1990); Gallo et al., *Dev. Biol.* 123:282 (1987)), collagen type IV (Hermanns et al., *Restor. Neurol. Neurosci.* 19:139 (2001); Hermanns et al. *J. Neurosci. Meth.* 110:141 (2001); Stichel et al. *Eur. J. Neurosci.* 11:632 (1999)), and the basal membrane (Lips et al. *J. Neurocytol.* 24:449 (1995); Stichel et al. *J. Neurocytol.* 23:615 (1994); Stichel et al. *Eur. J. Neurosci,* 7:401 (1995); Timpl et al. *Int. Rev. Exp. Pathol.* 29:1 (1986)).

Proteoglycans represent a special class of heavily glycosylated glycoproteins characterized by a protein core that is covalently linked by four sugar moieties to a sulphated glycosaminoglycan (GAG) chain. Among the four types of proteoglycans (Johnson-Green et al. *Glia* 4:314 (1991)), the chondroitin sulphate proteoglycans (CSPGs) are a relatively large family. Up-regulation of CSPG production has been documented in glial scars in both the brain and spinal cord of adult mammalians (Jones et al. *Exp. Neurol.* 182:399 (2003); McKeon et al. *J. Neurosci.* 19:10778 (1999); Tang et al. *J. Neurosci. Res.* 71:427 (2003)). The inhibitory effects of CSPGs on axonal outgrowth and CNS tissue regeneration have been demonstrated both in vitro (Hynds et al. *Exp. Neurol.* 160:244 (1999); Snow et al. *Exp. Neurol.* 109:111 (1990)) and in vivo (Jones et al. *J. Neurosci.* 22:2792 (2002); Moon et al. *Neuroscience* 109:101 (2002)), suggesting that elimination of these ECM molecules may be essential to promote CNS tissue repair and regeneration.

In addition to the inhibitory effects of CSPGs, several other molecules are known to be up-regulated in the glial scar and to contribute to regeneration failure. Collagen IV, a matrix molecule that is primarily secreted by meningeal fibroblasts, is a major component of the basal membrane, and has been implicated in the inhibition of regeneration after CNS injury (Klapka et al. *J. Neurotrauma* 23:422 (2006)). In a brain lesion model of post-commissural formix transaction, collagenous basal membrane was shown to be a major impediment for axon regeneration (Hermanns et al. *Restor. Neurol. Neurosci.* 19:139 (2001)). Blocking collagen IV deposition promoted axonal regeneration across the lesion site following mechanical injury to adult rat brain (Stichel et al. *Eur. J. Neurosci.* 11:632 (1999)).

Since any form of treatment designed to regenerate brain tissue after stroke, TBI, or SCI will have to occur at the lesion site, sustaining a scar-reduced, permissive environment is key to successful brain tissue regeneration. To that end, the present invention provides methods of preventing scar tissue growth in a CNS lesion, digesting existing scar tissue in a CNS lesion, and maintaining a scar-reduced environment in a CNS lesion.

Selective enzymatic removal of ECM molecules from glial scar tissue results in the degradation of pre-existing scars within the CNS lesion (Zuo et al., *J. Neurosci.* 18:5203 (1998); Zuo et al., *Exp. Neurol.* 154:654 (1998)), thereby enhancing CNS repair. For example, chondroitinase ABC ($Ch^{ase}ABC$) may be used to digest the GAG moieties of CSPGs, resulting in the dissolution of pre-existing scar tissue and enhanced axonal regeneration (Snow et al., *Exp. Neurol.* 109:111 (1990); Bradbury et al., *Nature* 416:636 (2002); Moon et al., *Nature Neurosci.* 4:465 (2001); Li et al., *J. Neurosci. Res.* 85:536 (2007)). Likewise, the degradation of collagen IV quells the lesion-induced deposition of basal membrane and partially facilitates CNS tissue regeneration (Stichel et al., *Eur. J. Neurosci.* 11:632 (1999); Guth et al., *J. Neurosurg.* 52:73 (1980)).

Thus, some embodiments of the present invention comprise a method of delivering to a lesion an amount of an in-situ crosslinkable hydrogel comprising at least one ECM-degrading enzyme, wherein said amount is effective to digest scar tissue. Appropriate enzymes may include, without limitation and in any combination, CSPG-digesting enzymes, such as $Ch^{ase}ABC$, and collagen-eliminating enzymes, such as collagenase IV. In certain embodiments, the ECM-based hydrogel comprises both $Ch^{ase}ABC$ and collagenase IV.

In addition to digesting pre-existing glial scar tissue, it is desirable to prevent the formation of new scar tissue in the lesion site. The formation of new scar tissue can be prevented by blocking the biosynthesis of repair-inhibiting ECM molecules. Several compounds have been found to be useful in the present invention to inhibit scar formation, including CSPG suppressors such as p-nitrophenyl-b-D-xylopyranoside (PNPX) (Zhang et al., World Congress on Tissue Engineering and Regenerative Medicine (2006) Pittsburgh, Pa., presented Apr. 27, 2006), and prolyl hydroxylase inhibitors (PHIs), such as ethyl-3,4 dihydroxybenoate (EDHB) and dimethyloxalylglycine (DMOG) (Zhang et al., Abstracts of Papers of the American Chemical Society 229:U911 (2005) San Diego, Calif., presented Mar. 13, 2005), which notably inhibit collagen IV synthesis. In addition, it is known that cyclic nucleotides are able to convert myelin-associated glycoproteins from an axon-repulsive state to one in which they attract axonal outgrowth.

Thus, embodiments of the present invention comprise a method of delivering to a lesion an amount of an in-situ crosslinkable hydrogel comprising at least one agent that blocks the biosynthesis of inhibitory ECM components, wherein said amount is effective to prevent scarring. Appropriate agents include those that block the biosynthesis of CSPG, such as PNPX, agents that block the biosynthesis of collagen IV, such as EDHB and DMOG, and cyclic nucleotides as well as any combination thereof. In certain embodiments, the in-situ crosslinkable hydrogel comprises at least one agent that blocks the biosynthesis of CSPG and at least one agent that blocks the biosynthesis of collagen IV.

Further embodiments of the present invention are aimed at maintaining a scar-reduced lesion site. These embodiments comprise a method of delivering to a lesion an amount of an in-situ crosslinkable hydrogel comprising at least one agent that blocks the biosynthesis of inhibitory ECM components and, optionally, at least one ECM-degrading enzyme, wherein said amount is effective to maintain a scar-reduced environment. Certain embodiments comprise an in-situ crosslinkable hydrogel that contains agents that block the biosynthesis of CSPG and collagen IV, as well as the enzymes $Ch^{ase}ABC$ and collagenase IV, in any combination.

Given the ubiquitous nature of CSPGs and collagen IV within the CNS, one skilled in the art will appreciate the need to carefully control the release of enzymes and/or agents that interfere with the normal life cycle of these ECM components. The present invention provides for such control via the slow, sustained release of ECM-degrading enzymes and biosynthesis-blocking agents within the lesion, with the release rate controlled by the composition (e.g., density, charge, shape) of the hydrogel.

IV. Topical Treatment of Spinal Cord Injury

Particular embodiments of this invention are based on the unexpected discovery that topical administration of a vehicle of this invention (e.g., a hydrogel, nanoparticle, microparticle, micelle, a membrane, a scaffold, or any combination thereof) to a spinal cord injury site can have a therapeutic effect. The vehicle can deliver factors and/or agents topically to the spinal cord injury site to impart a therapeutic effect. Such topical administration provides improved results as compared with administration of such vehicles and/or factor and agents via injection.

Thus, in one embodiment of this invention, a method is provided of treating a spinal cord injury, comprising topically delivering to the spinal cord injury site an amount of a neurotrophic factor and or an anti-inflammatory agent effective to treat the spinal cord injury.

Also provided herein is a method of reducing inhibition of axonal regeneration at a spinal cord injury site, comprising topically delivering to the site an amount of a neurotrophic factor and/or an anti-inflammatory agent effective in reducing inhibition of axonal regeneration at the spinal cord injury site.

In further aspects, the present invention provides a method of decreasing secondary injury at a spinal cord injury site, comprising topically delivering to the site an amount of a neurotrophic factor and/or an anti-inflammatory agent effective in decreasing secondary injury at the spinal cord injury site.

In the methods described herein, the spinal cord injury can be an acute spinal cord injury in some embodiments and the spinal cord injury can be a chronic spinal cord injury in some embodiments. For example, an acute spinal cord injury would be treated according to the methods described herein to decrease secondary injury at the spinal cord injury site.

In the methods described herein, the neurotrophic factor and/or anti-inflammatory agent can be in a vehicle that can be, but is not limited to, a hydrogel, a nanoparticle, a nanosphere, a microparticle, a microsphere, a liposome, a micelle, a membrane, a scaffold, or any combination thereof.

In some embodiments of this invention, the vehicle is a hydrogel, which in particular embodiments is a chitosan-gelatin based hydrogel. Thus, the neurotrophic factor and/or anti-inflammatory agent can be present in a chitosan-gelatin based hydrogel. Nonlimiting examples of other hydrogels include a chitosan-laminin based hydrogel.

Nonlimiting examples of a neurotrophic factor or other factor (e.g., growth factor) that can be used in this invention include, in any combination, glial derived neurotrophic factor (GDNF), brain derived neurotrophic factor (BDNF), vascular endothelial growth factor V(EGF), neurotrophin-3 (NT-3), neurotrophin-4 (NT-4), ciliary neurotrophic factor (CNTF), hepatocyte growth factor (HGF), nerve growth factor (NGF), granulocyte colony stimulating factor (G-CSF), fibroblast growth factor (FGF), etc., as are well known in the art (see, e.g., Hempstead. "Dissecting the diverse actions of pro- and mature neurotrophins" *Curr Alzheimer Res* 3(1):19-24 (2006); Reichardt. "Neurotrophin-regulated signalling pathways" *Philos. Trans. R. Soc. Lond., B, Biol. Sci.* 361:1545-64 (2006); Allen and Dawbarn "Clinical relevance of the neurotrophins and their receptors" *Clin. Sci.* 110(2):175-91 (2006).

The present invention further provides a method of delivering a neurotrophic factor, growth factor and/or an anti-inflammatory agent to a spinal cord injury site, comprising topically delivering to the spinal cord injury site a vehicle comprising the neurotrophic factor, growth factor and/or anti-inflammatory agent, wherein the vehicle is selected from the group consisting of a hydrogel, a nanosphere, microsphere, membrane, scaffold or any combination thereof, thereby delivering the neurotrophic factor, growth factor and/or the anti-inflammatory agent to the spinal cord injury site.

Additionally provided herein is a method of preventing or reducing scar tissue growth at a spinal cord injury site, comprising topically delivering to the site an effective amount of at least one agent that reduces recruitment of particular cells (e.g., macrophages, neutrophils, astrocytes fibroblasts, lymphocytes, microglia, eosinophils, mast cells, monocytes, granulocytes, T-cells, B-cells, NK cells) to the injury site and/or reduces the inflammatory response of these cells at the spinal cord injury site, thereby preventing or reducing scar tissue growth at the spinal cord injury site. Nonlimiting examples of such agents of this invention include methylprednisone, dexamethasone, erythropoietin, minocyclin, progesterone, estrogen, anti CD-11 antibodies, magnesium sulfate, riluzole, polyethylene glycol, atorvastatin, ionosin, pioglitazone, chondrotinase ABC, anti Nogo antibodies and any combination thereof.

Furthermore, the present invention provides a method of recruiting stem cells to a spinal cord injury site, comprising topically delivering to the site at least one neural stem cell recruiting factor. Nonlimiting examples of a neural stem cell recruiting factor include stromal cell-derived factor 1α (SDF-1α) (Imitola et al. "Directed migration of neural stem cells to sites of CNS injury by the stromal cell-derived factor 1α/CXC chemokine receptor 4 pathway" *PNAS* 101(52): 18117-18122 (2004), hepatocyte growth factor (HGF), human recombinant annexin A2, stem cell factor-1, MCP-1, SCYA2, CCL2, MCAF, VEGF, EGF, transmembrane protein 18, tenascin-C, IGF-1, FGF-2, PDGF and any combination thereof.

In the above methods, the agent that reduces recruitment of cells to the injury site and/or reduces the inflammatory response of these cells at the injury site can be in a vehicle that can be a hydrogel, a nanoparticle, a nanosphere, a microparticle, a microsphere, a liposome, a micelle, a membrane, a scaffold and any combination thereof. In some embodiments, the vehicle is a hydrogel, which in particular embodiments is a chitosan-gelatin based hydrogel.

In the above methods, wherein the neural stem cell recruiting factor is in a vehicle that can be a hydrogel, a nanoparticle, a nanosphere, a microparticle, a microsphere, a membrane, a scaffold and any combination thereof. In some embodiments, the vehicle is a hydrogel, which in particular embodiments is a chitosan-gelatin based hydrogel.

In some embodiments, a hydrogel can be topically administered or delivered to a spinal cord injury site to impart a therapeutic effect. Thus, the present invention provides a method of treating a spinal cord injury, comprising topically delivering to the spinal cord injury site an amount of a chitosan/gelatin based hydrogel effective to treat the spinal cord injury.

Also provided herein is a method of reducing inhibition of axonal regeneration at a spinal cord injury site, comprising topically delivering to the site an amount of a chitosan-gelatin based hydrogel effective in reducing inhibition of axonal regeneration at the spinal cord injury site.

In further aspects, the present invention provides a method of decreasing secondary injury at a spinal cord injury site, comprising topically delivering to the site an amount of a chitosan-gelatin based hydrogel effective in decreasing secondary injury at the spinal cord injury site.

In some embodiments, the hydrogel can comprise, consist essentially of or consist of chitosan and gelatin. In some embodiments, the hydrogel can comprise, consist essentially or of consist of chitosan and laminin. In some embodiments, the hydrogel can comprise cells, constructs and/or implants (e.g., neural stem cells, embryonic stem cells, olfactory ensheathing cells, neural progenitor cells, neural stem cell derived precursor cells, fibroblasts, bone marrow derived stem cell, Dorsal root ganglion, axonal constructs, peripheral nerve implants, Schwann cells and any combination thereof) prior to delivery or administration to a subject. In some embodiments, the hydrogel contains no cells (e.g., no stem cells) prior to delivery or administration to the subject.

In some embodiments of this invention, the hydrogel is designed for sustained release of the factor, agent, or other substance or material present in the hydrogel. Nonlimiting examples include sustained release for at least 5 days, 10 days, 15 days, 20 days, 30 days, 40 days, 50 days, 60 days, etc. To design the hydrogel for sustained release as described herein, the polymer concentration of the hydrogel can be modified. For example higher gelatin concentration stabilizes the hydrogel and slows release of the factor, agent or other substance or material in the hydrogel. The crosslinking density also affects the release rate. This can be modified by adjusting the crosslinking time by adding different cross linkers and changing crosslinker concentration. Finally the factor, agent or other substance or material can be stabilized by adding heparin and/or albumin, which protect the factor, agent or other substance of material and also cause slow and timed release. It would known to one of skill in the art how to determine the appropriate polymer concentration (e.g., a polymer formed by combining chitosan and gelatin in particular ratios as described herein), crosslinker type, crosslinker concentration, heparin and/or albumin concentration, etc., to achieve a particular controlled release rate from the hydrogel as described herein.

The chitosan/gelatin hydrogel of this invention can comprise a crosslinker, nonlimiting examples of which include genipin (covalent cross linker) and glycerol phosphate (ionic crosslinker). In some embodiments, genipin is added first, right after mixing of chitosan and gelatin. This acts as the first crosslinker directly between the ingredients for the formation of the polymer. Glycerol phosphate can be added immediately before application/administration to the subject and further reinforces the structure and gives it the unique property of being a gel at the body temperature of the subject. In some embodiments, the concentration of genipin in the hydrogel can be about 0.4 mM (e.g., about 0.2 mM, 0.25 mM, 0.3 mM, 0.35 mM, 0.4 mM, 0.45 mM, 0.5 mM, 0.55 mM or 0.6 mM, etc.). In some embodiments, the concentration of glycerol phosphate in the hydrogel can be about 3 mg/ml (e.g., 0.1 mg/ml, 0.5 mg/ml, 1.0 mg/ml, 1.5 mg/ml, 2.0 mg/ml, 2.5 mg/ml, 3.0 mg/ml, 3.5 mg/ml, 4.0 mg/ml, 4.5 mg/ml, 5.0 mg/ml, 6.0 mg/ml, 7.0 mg/ml, 8.0 mg/ml, 9.0 mg/ml, 10 mg/ml, 15 mg/ml, 20 mg/ml, 25 mg/ml, 30 mg/ml, 35 mg/ml, 40 mg/ml, 45 mg/ml, 50 mg/ml, 60 mg/ml, 70 mg/ml, 80 mg/ml, 90 mg/ml, 100 mg/ml, etc.)

Further embodiments of the present invention comprise in-situ crosslinkable hydrogels wherein the factor, agent, and/or other material or substance contained therein is present as a nanoparticle. In certain embodiments, the factor, agent, and/or other material or substance will be loaded into a biodegradable nanoparticle, such as PLGA, liposomes, micelles, and/or any other suitable degradable polymers, as are well known in the art.

The hydrogels of this invention can further comprise a polyalkylene glycol (PAG) moiety, which is some embodiments can be poly(ethylene glycol (PEG). The PAG or PEG can have a molecular weight in the range of about 10,000 to about 40,000. The PEG of this invention can be single arm or multi-arm (e.g., 1, 2, 3, 4, 5, 6, 7, 8, 9, or 10 arms, etc.) PEG.

"Polyalkylene glycol" means straight or branched polyalkylene glycol polymers including, but not limited to, polyethylene glycol (PEG), polypropylene glycol (PPG), and polybutylene glycol (PBG), as well as co-polymers of PEG, PPG and PBG in any combination, and includes the monoalkylether of the polyalkylene glycol. Thus, in various embodiments of this invention, the polyalkylene glycol in the compositions of this invention can be, but is not limited to, polyethylene glycol, polypropylene glycol, polybutylene glycol, and any combination thereof.

In certain embodiments, the polyalkylene glycol of the composition is polyethylene glycol or "PEG." The term "PEG subunit" refers to a single polyethylene glycol unit, i.e., —($CH_2CH_2O$)—.

In some embodiments, the polyalkylene glycol (e.g., PEG) can be non-polydispersed, monodispersed, substantially monodispersed, purely monodispersed, or substantially purely monodispersed.

"Monodispersed" is used to describe a mixture of compounds wherein about 100 percent of the compounds in the mixture have the same molecular weight.

"Substantially monodispersed" is used to describe a mixture of compounds wherein at least about 95 percent of the compounds in the mixture have the same molecular weight.

"Purely monodispersed" is used to describe a mixture of compounds wherein about 100 percent of the compounds in the mixture have the same molecular weight and have the same molecular structure. Thus, a purely monodispersed mixture is a monodispersed mixture, but a monodispersed mixture is not necessarily a purely monodispersed mixture.

"Substantially purely monodispersed" is used to describe a mixture of compounds wherein at least about 95 percent of the compounds in the mixture have the same molecular weight and have the same molecular structure. Thus, a substantially purely monodispersed mixture is a substantially monodispersed mixture, but a substantially monodispersed mixture is not necessarily a substantially purely monodispersed mixture.

V. Synthetic Cell Platform

In some embodiments of the invention, a synthetic cell culture platform is provided, comprising: a two dimensional and/or three dimensional surface comprising, consisting essentially of, or consisting of peptides conjugated to said surface, said peptides comprising, consisting essentially of, or consisting of one or more peptides of this invention (e.g., a peptide having the amino acid sequence of any one of SEQ ID NOS:1 to 14 or a combination thereof). In a representative embodiment, the peptide comprises, consists essentially of; or consists of the amino acid sequence CCRRIKVAVWLC (SEQ ID NO:1).

In particular embodiments, the two dimensional surface includes but is not limited to an in vitro cell culturing surface. In some embodiments, the three-dimensional surface includes but is not limited to a hydrogel as described herein.

In still other embodiments, the peptides are conjugated to the two- and three-dimensional surfaces at a concentration of 10 μM or less. Thus, the peptides of the invention can be conjugated to the surfaces at a concentration of 0.25 μM, 0.5 μM, 1 μM, 2 μM, 3 μM, 4 μM, 5 μM, 6 μM, 7 μM, 8 μM, 9 μM, 10 μM, and any range therein.

In further embodiments, the present invention provides a method of increasing cell adhesion, stable attachment and/or proliferation of cells, the method comprising: contacting the cells with a platform of the invention; and culturing the cells on said platform, wherein the cells have increased cell adhesion, stable attachment and proliferation as compared to a control cells not grown on a platform of the invention (e.g., a platform that does not comprise, consist essentially of, consist of peptides of this invention). As described herein, the cells can be any cell type including but not limited to stem cells, neural stem cells, embryonic stem cells, olfactory ensheathing cells, neural progenitor cells, neural stem cell derived precursor cells, fibroblasts, bone marrow derived stem cells, Schwann cells, and the like, or any combination thereof. In representative embodiments, the cells are human cells (e.g., human stem cells, human neural stem cells and the like)

In still further embodiments, a method of promoting differentiation of neural stem cells into neurons is provided, comprising: contacting neural stem cells with a platform of the present invention; and culturing the cells on said platform, wherein the differentiation of the neural stem cells into neurons is promoted. In some particular embodiments, the differentiation of the neural stem cells into neurons is promoted as compared to a control (e.g., neural stem cells contacted and cultured on a stem cell platform that does not comprise, consist essentially of, consist of peptides of this invention).

The present invention is explained in greater detail in the following non-limiting examples.

EXAMPLES

Example 1

Composition of Synthetic Hydrogels

Figures 1A, 1B:
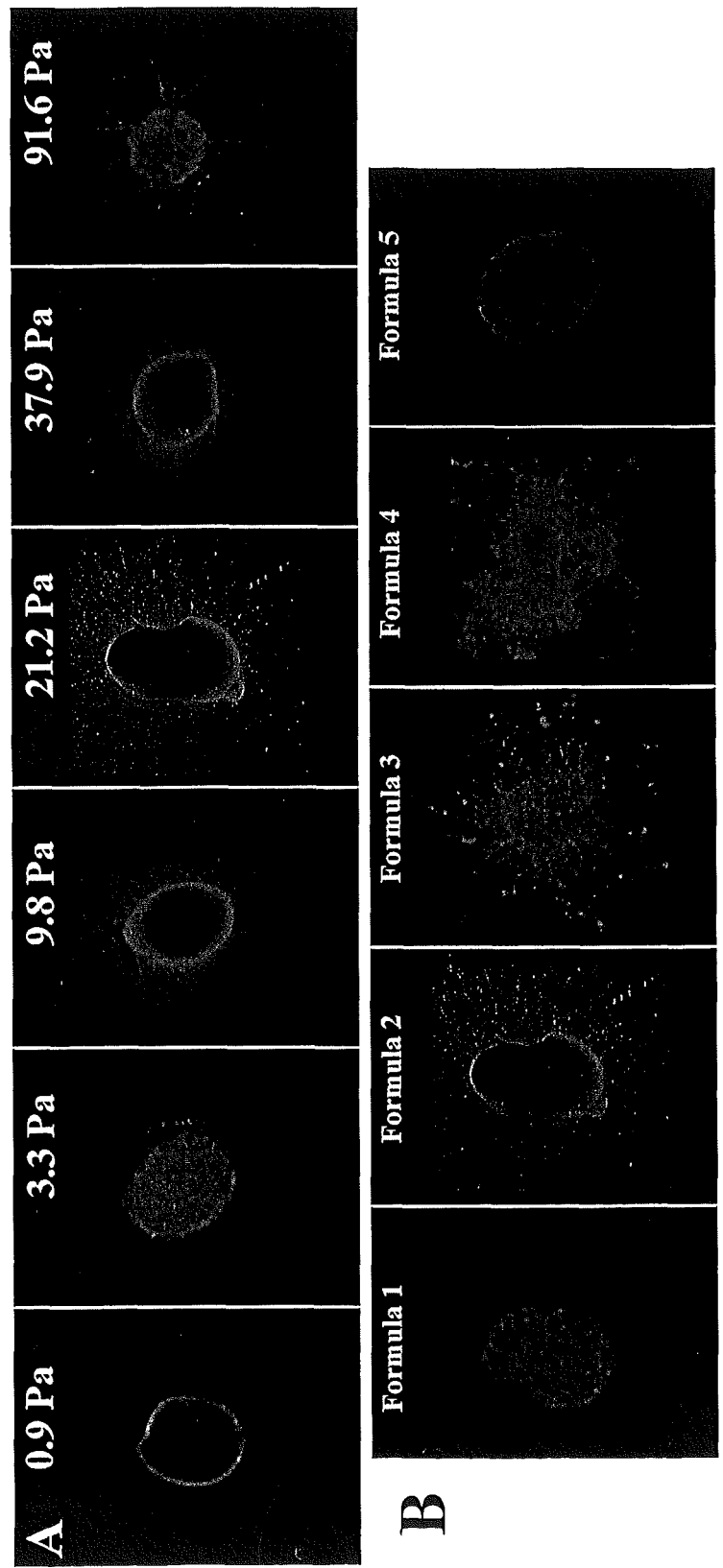
FIGS. 1A-1B show human embryonic stem cell derived neurospheres cultured inside hydrogels comprising different ratios on thiolated multi-arm PEG and a laminin-derived short peptide sequence (CDPVCC GTARPGYIGSRG-TARCCAC, SEQ ID NO:2). Formula 1 is 100% PEG, Formula 2 is 75% PEG, Formula 3 is 50% PEG, Formula 4 is 25% PEG, and Formula 5 is 0% PEG.

FIGS. 1A-C show human embryonic stem cell derived neurospheres cultured in hydrogels comprising different ratios of 4-Arm PEG and short peptide sequence (CDPVCC GTARPGYIGSRGTARCCAC, SEQ ID NO:2). While all of the hydrogels supported growth of the cells, a PEG:peptide ratio of 25:75 produced the best results.

Example 2

Figure 2A:
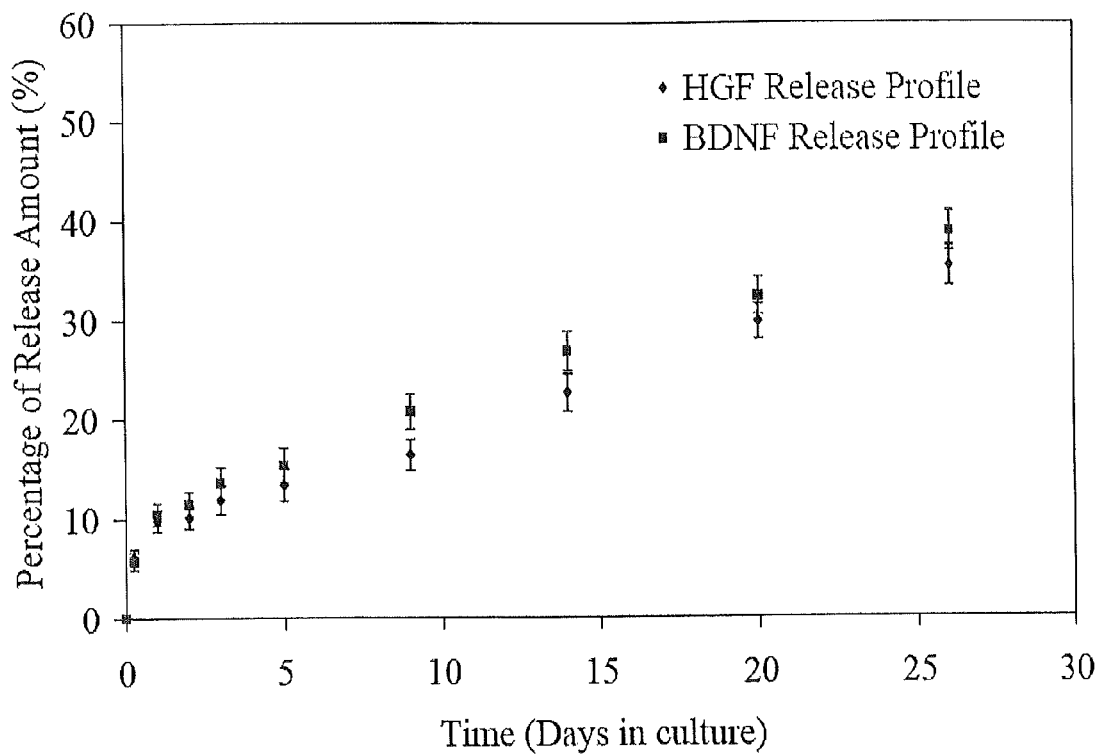
FIGS. 2A-2B show sustained release of biologically active molecules from an ECM-based hydrogel.
Figure 2B:
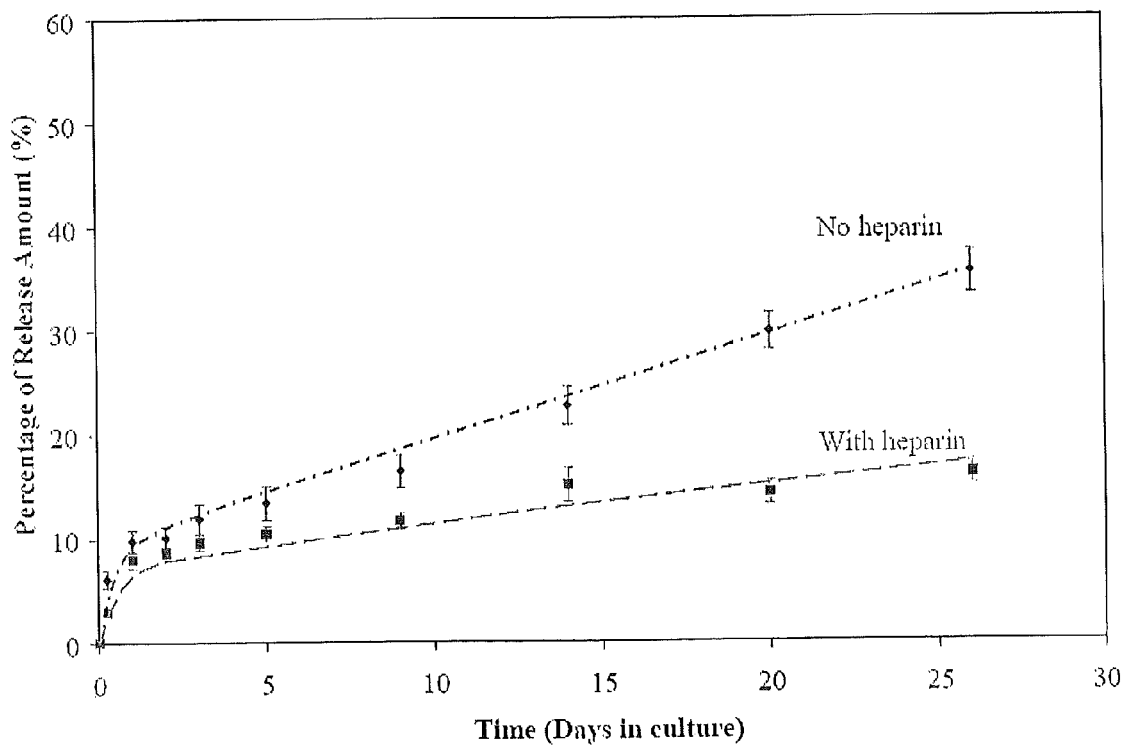
Figure 2C:
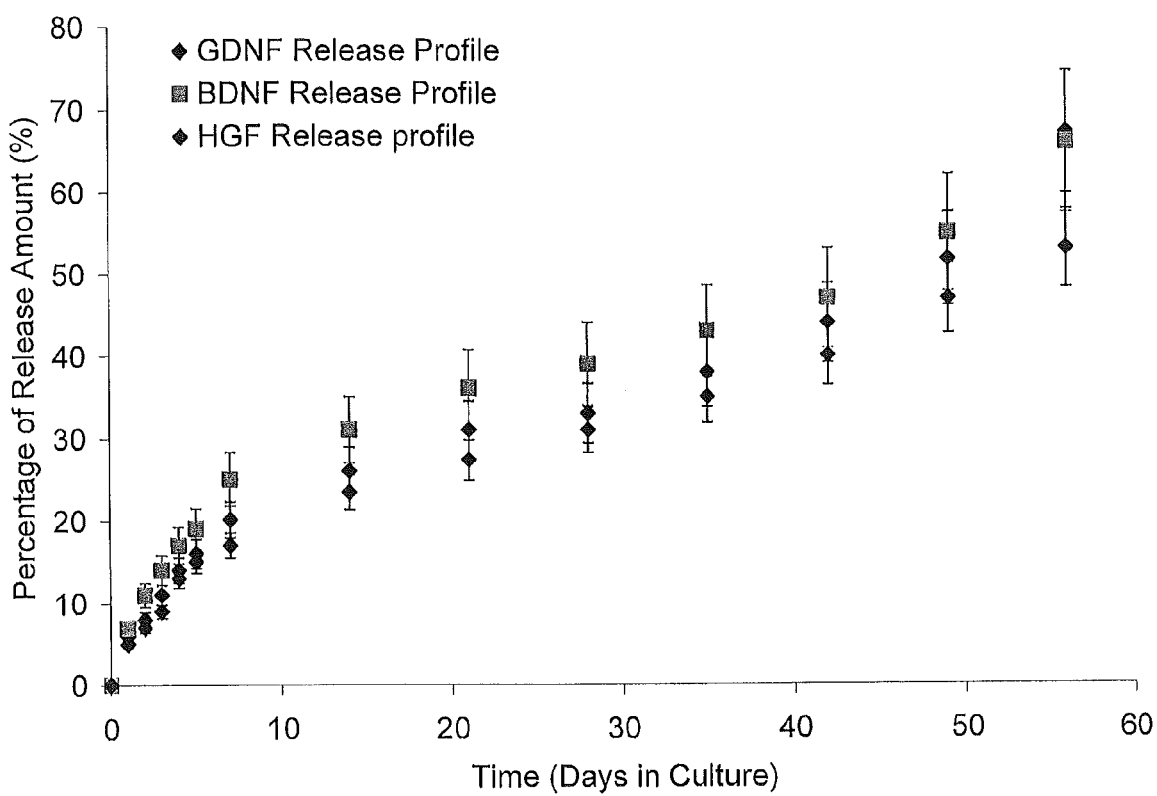
FIG. 2C shows sustained release of biologically active molecules from 4-arm thiolated PEG and thiolated laminin short peptide based hydrogel. Cumulative in vitro GDNF, BDNF and HGF release from the synthetic hydrogel is measured. After 1 and 2 months, about 35% and 70%, respectively, of the growth factors are released.

Sustained Release of Biologically Active Molecules from In-Situ Crosslinkable Hydrogels FIGS. 2A-C show sustained release of biologically active molecules from an ECM-based hydrogel. (A) Cumulative in vitro HGF and BDNF release from an ECM-based hydrogel comprising hyaluronic acid and collagen. After 26 days, approximately 35-40% of each growth factor was released from each hydrogel. (B) Cumulative in vitro HGF release from ECM-based hydrogels comprising hyaluronic acid and collagen (circles), or hyaluronic acid, collagen and heparin (squares). Addition of heparin in HA-collagen hydrogel doubles the release duration of HGF from the hydrogels. The hydrogel provides sustained release of biologically active growth factor in vitro, with release sustained for 3-6 months. This is a dramatic increase in time of availability compared to the short half-life of free growth factors in vivo. (C) Cumulative in vitro GDNF, BDNF and HGF release from the synthetic hydrogel. After 1 and 2 months, about 35% and 70%, respectively, of the growth factors are released.

Example 3

Attracting Stem Cells In Vitro and In Vivo

Figures 3A, 3B:
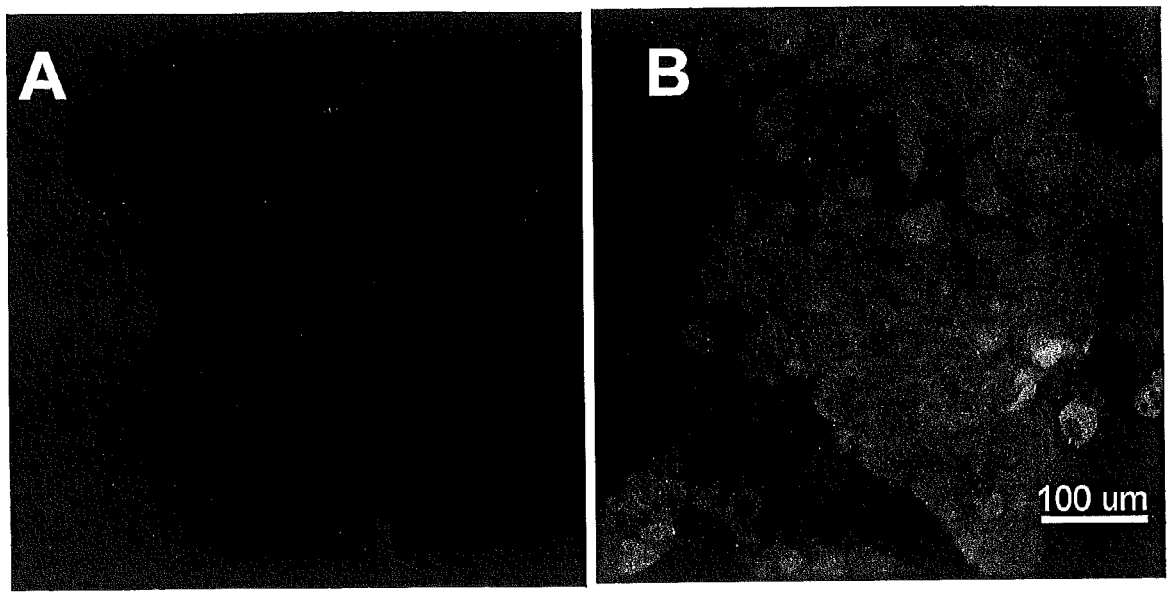
FIGS. 3A-3B show recruitment of stem cells to hydrogels containing hepatocyte growth factor in vitro. Sustained and localized release of HGF from hydrogels (B) is able to induce neural stem cell migration and recruitment into the hydrogel. Dark grey is staining for cell nuclei; black spotting is neurofilament staining, and light grey is nestin staining for neural stem cells. (A) is no HGF control.
Figure 4A:
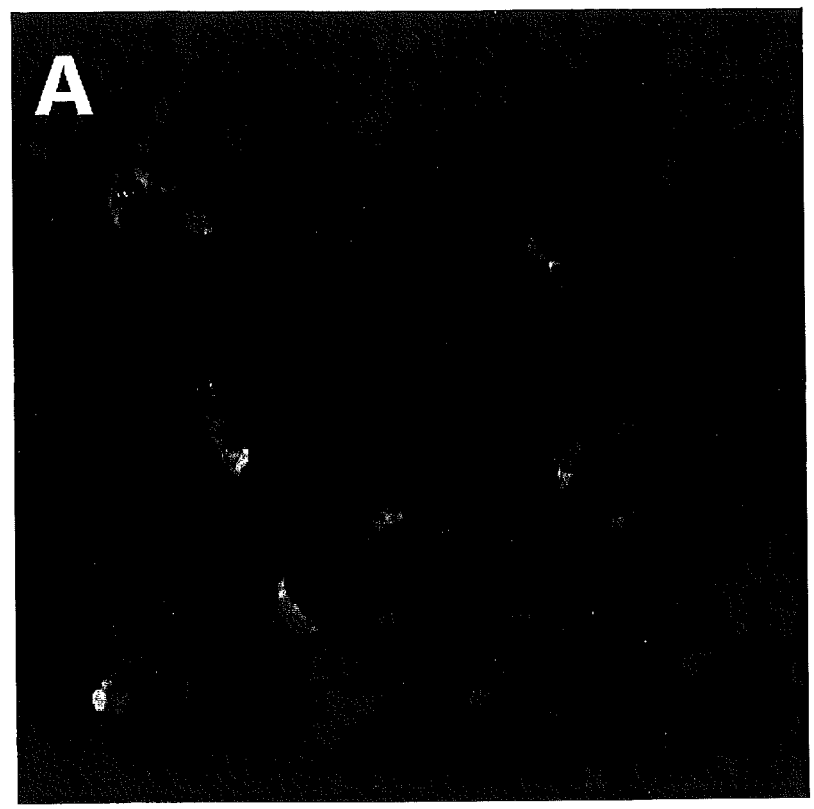
FIGS. 4A-4D show recruitment of endogenous stem cells to hydrogels containing hepatocyte growth factor. ECM-based hydrogels loaded with (A) control or (B) HGF were implanted into the subcutaneous space on the back of mice. Hydrogels were harvested 1 week after implantation, and samples of each were stained. C. Quantitative analysis of the total number of cells that migrated into control and HGF-containing hydrogels. D. HGF-loaded hydrogel stained with anti-STRO-1 following 1 week incubation in the subcutaneous space on the back of a mouse.
Figure 4B:
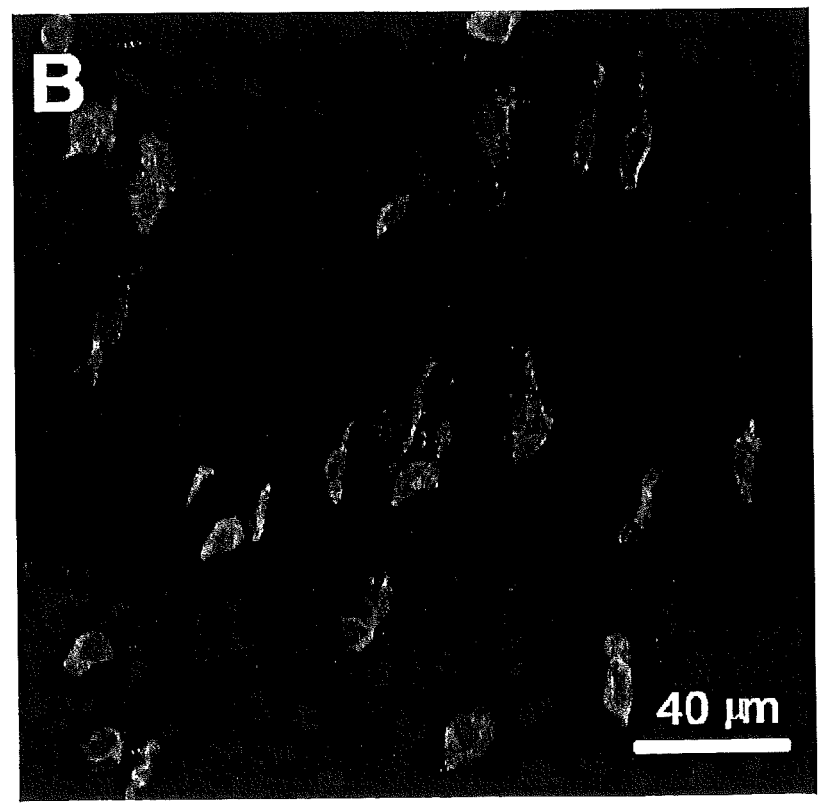
Figure 4C:
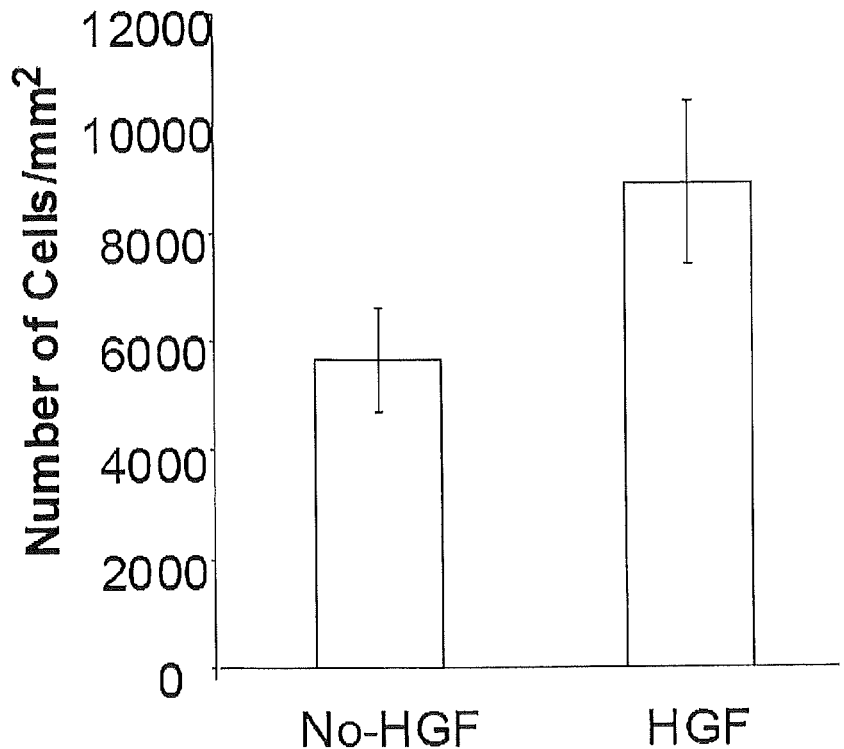
Figure 4D:
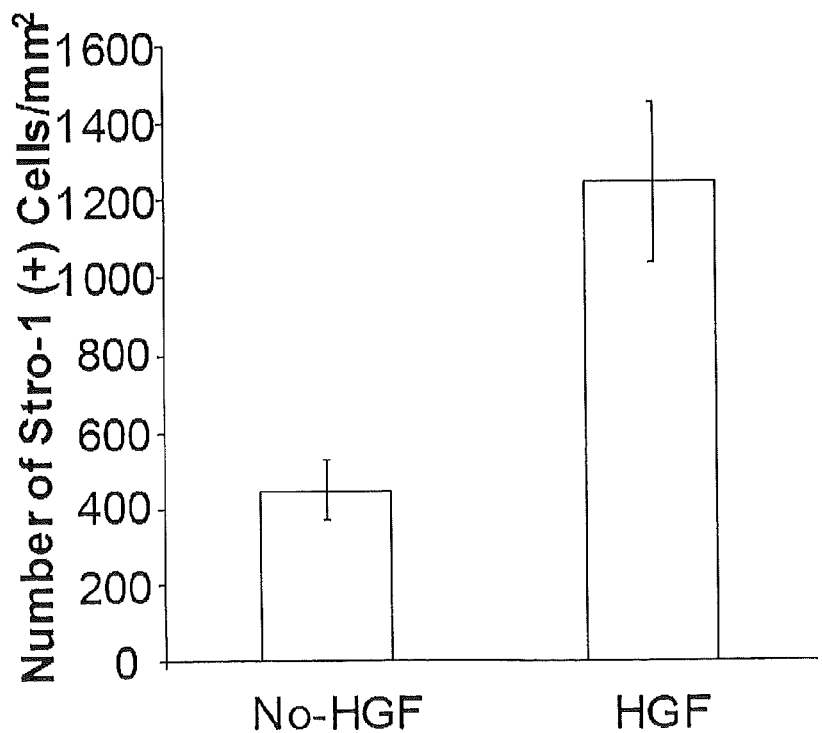
Figure 5A:
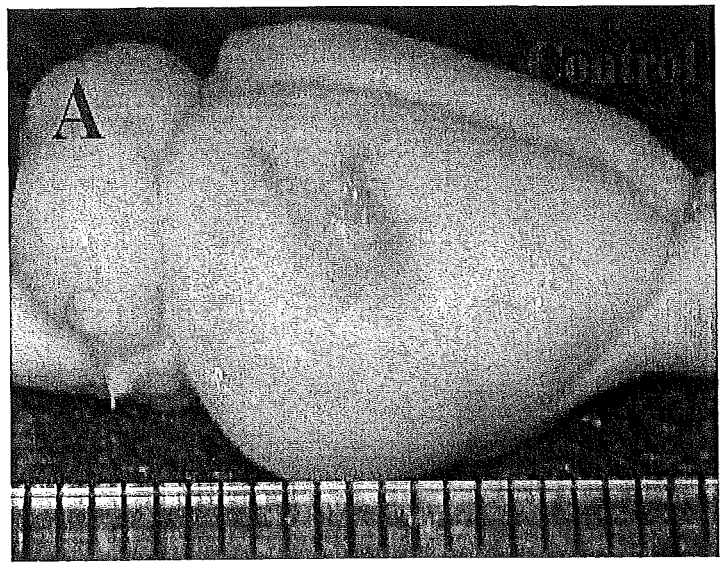
FIGS. 5A-5F show revascularization of a CNS lesion with injection of in-situ crosslinkable hydrogel following stroke.
Figure 5B:
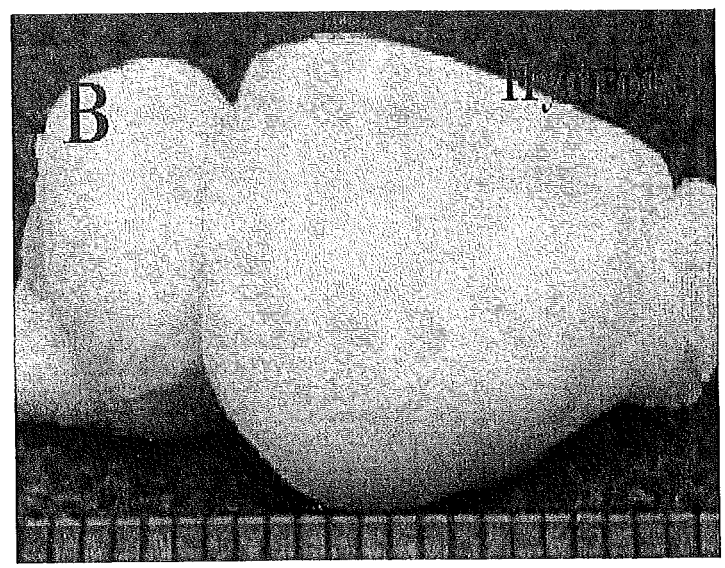
Figures 5C, 5D, 5E, 5F:
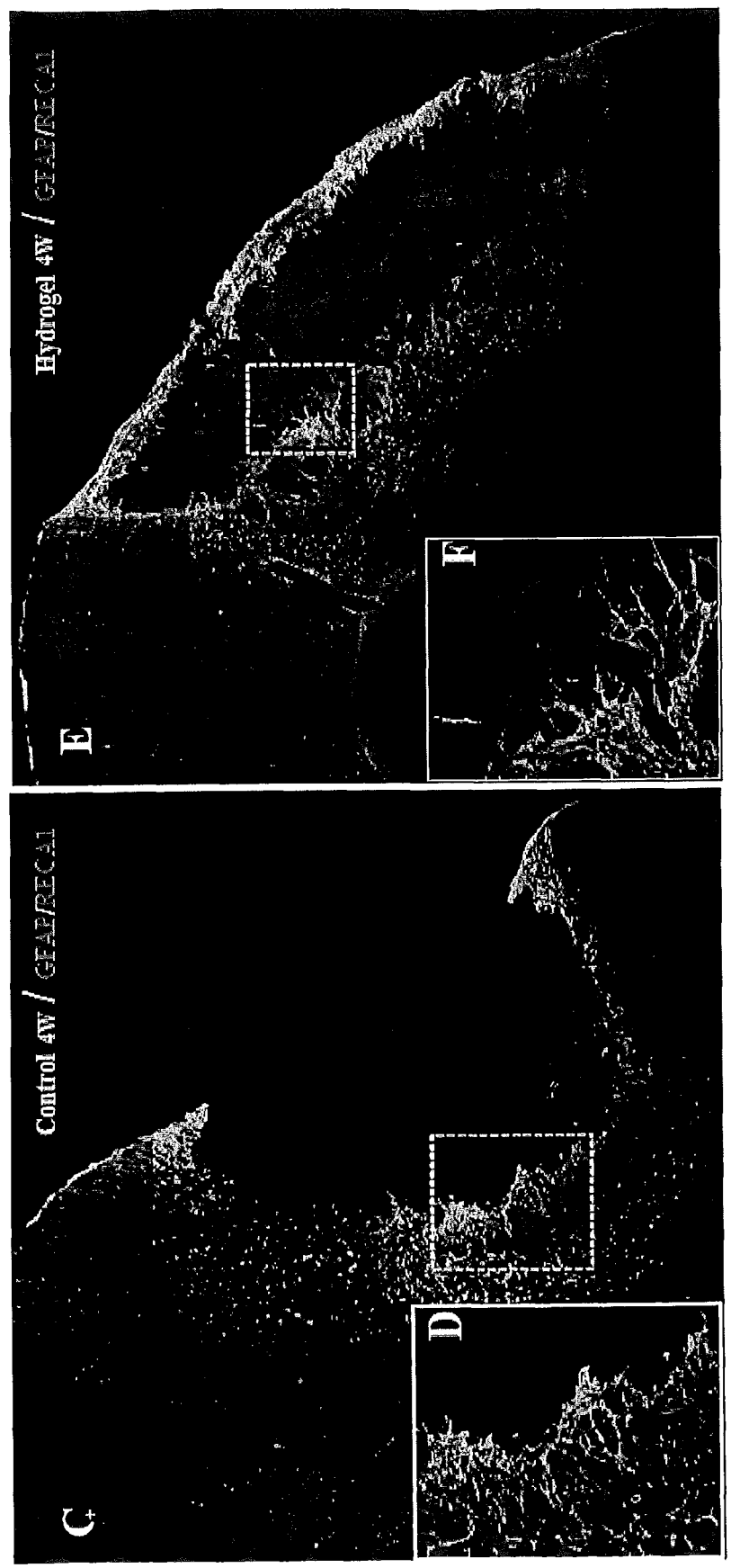
Figures 6A, 6B, 6C, 6D, 6E:
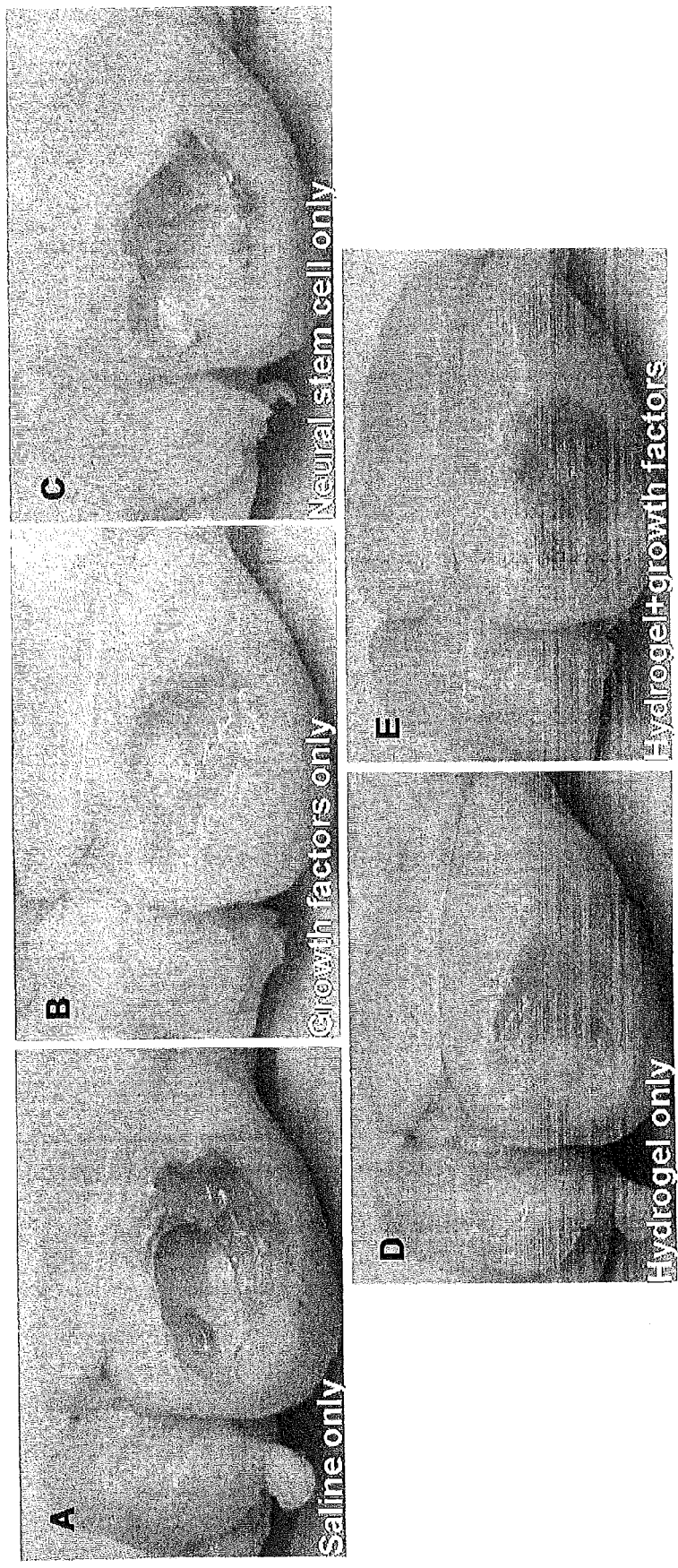
FIGS. 6A-6E show different outcomes after TBI. (A) Cavity formed at the lesion site 8 weeks after saline injection at the 3rd day after traumatic brain injury (TBI). (B) Cavity formed at the lesion site 8 weeks after direct injection of growth factors (HGF, GDNF, BDNF, FGF2) without using hydrogels. (C) Cavity formed at the lesion site 8 weeks after direct injection of neural stem cells without using hydrogels. (D) No cavity formation was found 8 weeks after hydrogel injection at the 3rd day after traumatic brain injury (TBI). (E) No cavity formation was found 8 weeks after injection of growth factors (HGF, GDNF, BDNF, FGF2) loaded in hydrogel at the 3rd day after traumatic brain injury (TBI).

FIGS. 3A-B show recruitment of stem cells to in-situ crosslinkable hydrogels containing hepatocyte growth factor (HGF). Neural stem cells ($5\times10^3$ in 200 µl culture media) were added to the upper compartment of a transwell. The lower compartment was filled with 400 µl of culture medium and an in-situ crosslinkable hydrogel as control (A), or an in-situ crosslinkable hydrogel containing 80 ng/ml solubilized HGF (B). Hydrogels were harvested following an 8-hour incubation period and stained. Sustained and localized release of HGF from the hydrogel (B) is able to induce neural stem cell migration and recruitment into the hydrogel.

FIGS. 4A-D show recruitment of endogenous stem cells to ECM-based hydrogels containing hepatocyte growth factor (HGF). ECM-based hydrogels loaded with control (A) or HGF (B) were implanted into the subcutaneous space on the back of mice. Hydrogels were harvested 1 week after implantation and samples of each were stained. (C) Quantitative analysis of the total number of cells that migrated into control and HGF-containing hydrogels. (D) HGF-loaded hydrogel stained with anti-STRO-1 following 1 week incubation in the subcutaneous space on the back of as mouse.

Example 4

Stroke Animal Model

FIGS. 5A-F show revascularization of a CNS lesion following stroke. (A, C, D) Adult rat brain four weeks after focal ischemic stroke (untreated). (B, E, F) Adult rat brain treated with an in-situ crosslinkable hydrogel four weeks after focal ischemic stroke. A and B depict the gross morphology of the brains. C and E contain mosaic image reconstructions of the lesions. Higher resolution images of the lesions interfaces are provided in D and F. As shown in panel E, a well-structured vasculature network was rebuilt at the lesion injected with the in-situ crosslinkable hydrogel of this invention.

Example 5

TBI Animal Model

FIGS. 6A-E show different outcomes after traumatic brain injury (TBI). (A) Cavity formed at the lesion site 8 weeks after saline injection at the 3rd day after traumatic brain injury (TBI). (B) Cavity formed at the lesion site 8 weeks after direct injection of growth factors (HGF, GDNF, BDNF, FGF2) without using hydrogels. (C) Cavity formed at the lesion site 8 weeks after direct injection of neural stem cells without using hydrogels. (D) No cavity formation was found 8 weeks after hydrogel injection at the 3rd day after traumatic brain injury (TBI). (D) No cavity formation was found 8 weeks after injection of growth factors (HGF, GDNF, BDNF, FGF2) loaded in hydrogel at the 3rd day after traumatic brain injury (TBI).

Example 6

Endogenous Neural Stem Cell Recruitment

Figures 7A, 7B:
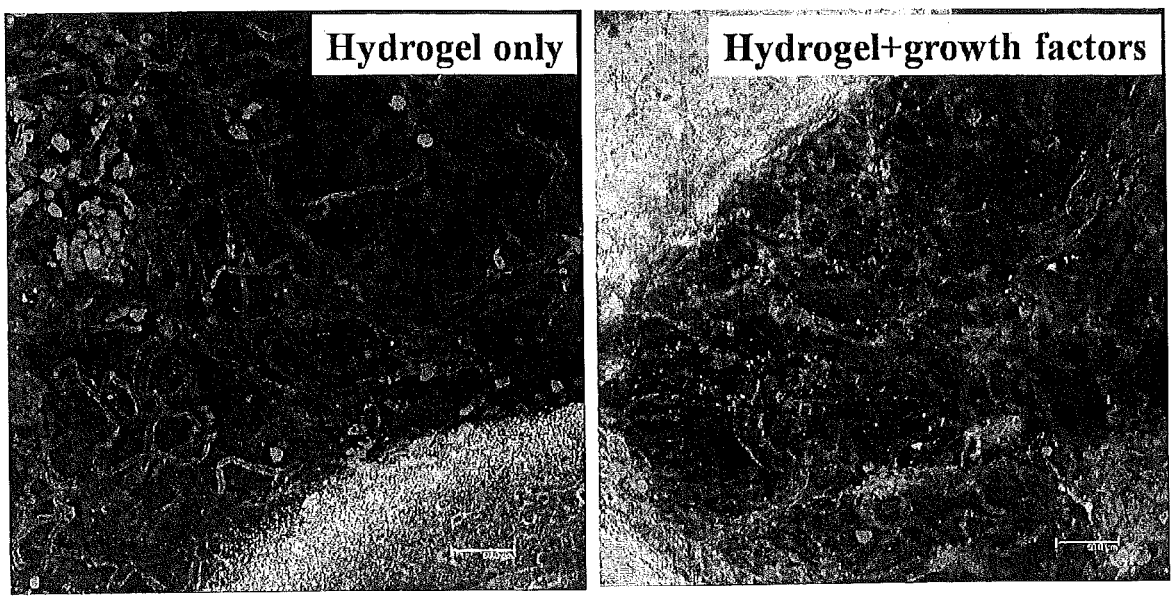
FIGS. 7A-7B. Neural regeneration after hydrogel injection. (A) There is robust vascular formation (light grey), but no neuronal regeneration in the TBI lesion site after only hydrogel injection without the use of growth factor cocktail. (B) There is robust vascular formation and neuronal regeneration (very light grey) after growth factor cocktail (HGF, FGF2, GDNF, BDNF) loaded hydrogel injection.

FIGS. 7A-B show neural regeneration after hydrogel injection. (A) There is robust vascular formation, but no neuronal regeneration in the TBI lesion site after only hydrogel injection without the use of the growth factor cocktail. (B) There is robust vascular formation and neuronal regeneration after growth factor cocktail (HGF, FGF2, GDNF, BDNF)-loaded hydrogel injection.

Example 7

Carrier for Transplantation

Figures 8A, 8B:
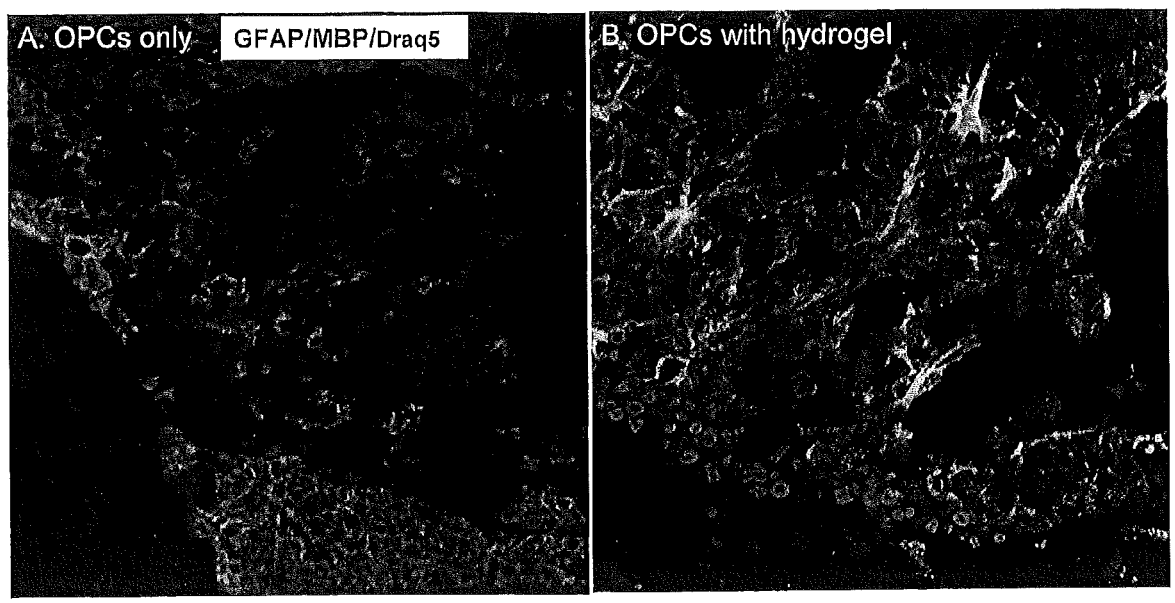
FIGS. 8A-8B. Four weeks after oligodendrocytes precursor cells (OPCs) transplanted into the ethidium bromide localized lesion rat spinal cord. (A) OPC only and (B) OPC transplanted with the hydrogel. Light grey is MBP (myelin basic protein) staining for differentiated oligodendrocytes. Very light grey is GFAP staining for astrocytes and dark grey is Draq-5 staining for cell nuclei. As shown in (B), more functionally viable oligodendrocytes and more myelination are seen in the hydrogel groups.
Figure 9A:
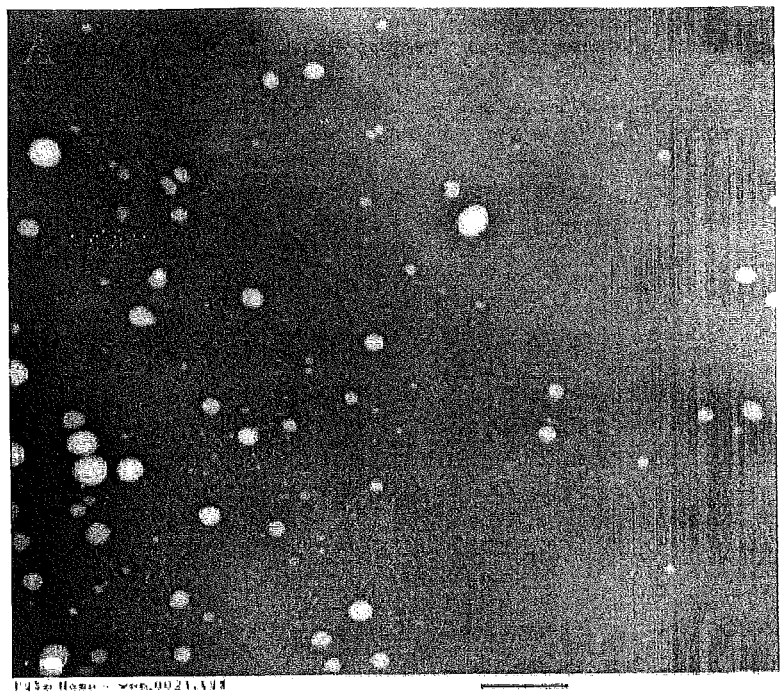
FIGS. 9A-9D. Inhibition of collagen IV biosynthesis using dimethyloxalylglycine (DMOG) nanoparticles. (A) Degradable nanoparticles loaded with DMOG. (B) Size distribution of DMOG-loaded nanoparticles (average size=45 nm). (C) Nanoparticles stained with anti-collagen IV antibody 4 weeks after the implantation of control nanoparticles. (D). nanoparticles containing DMOG. Scale bar=75 um. Dotted lines indicate the borders of implanted hollow fibers.
Figure 9B:
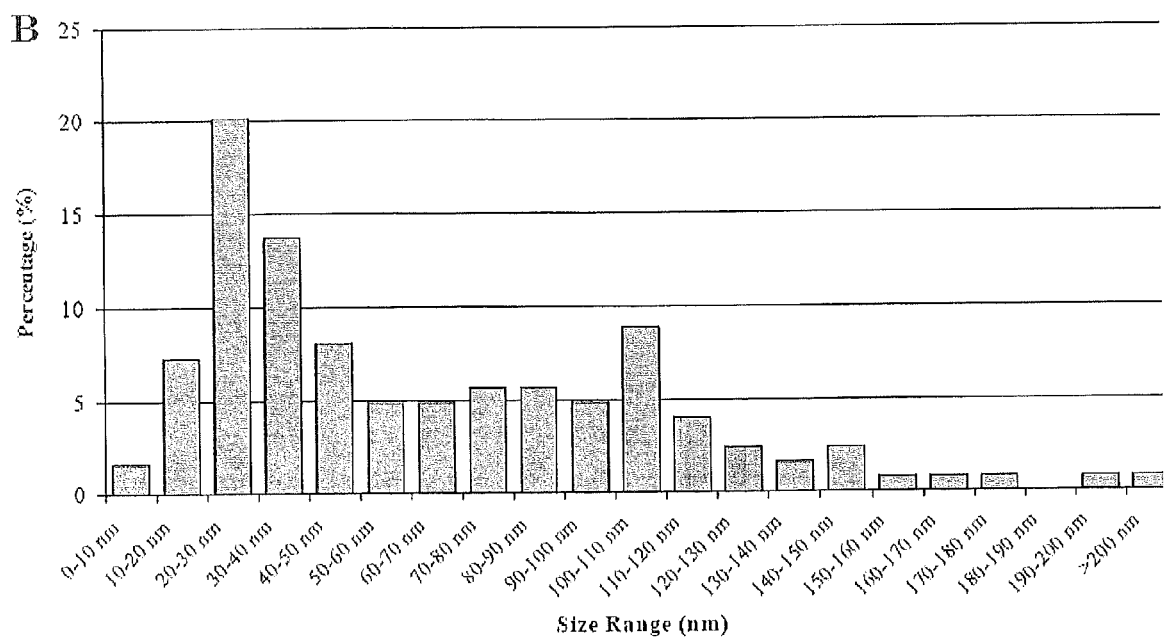
Figure 9C:
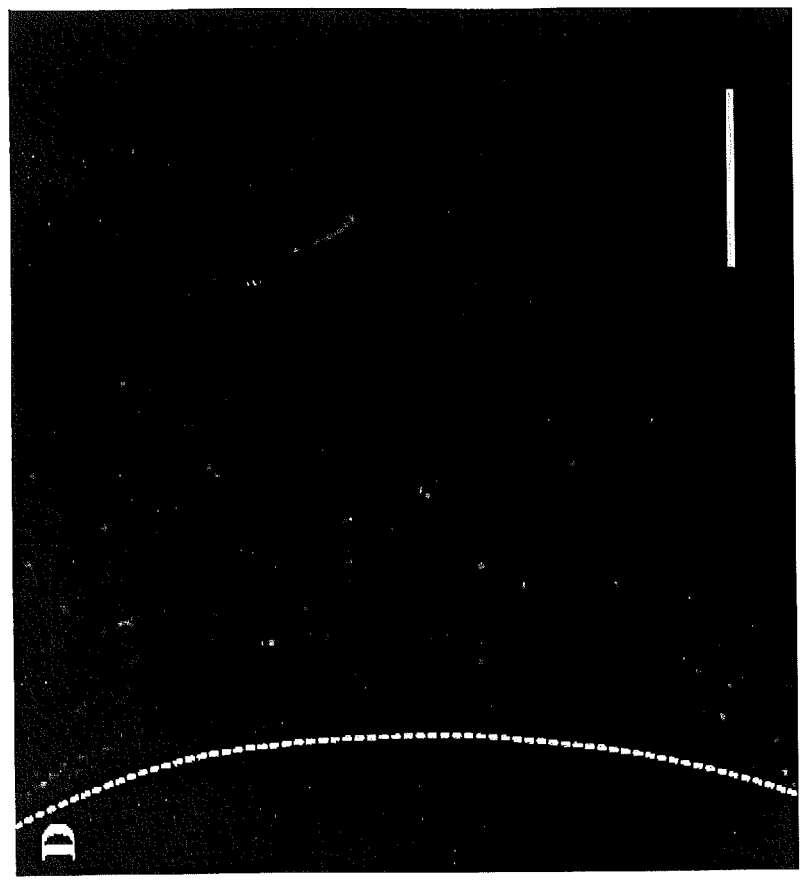
Figure 9D:
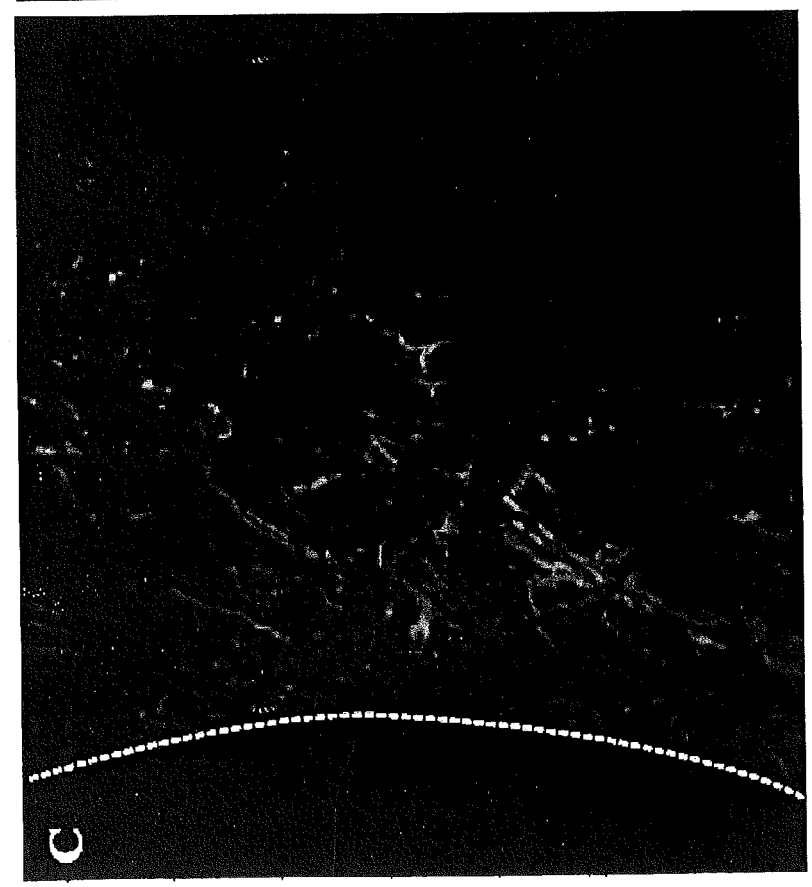

Myelin is damaged in many diseases, such as multiple sclerosis (MS) and leukodystrophies. Myelin is also destroyed in neural tissue injury, such as spinal cord injury (SCI) and traumatic brain injury (TBI). Remyelination has to occur in order to cure these diseases and is also the key step to fully regenerate injured spinal cord or brain tissue. At present, there are no effective therapies in the clinic that promote remyelination. There is growing evidence that exogenous cell transplantation is one promising strategy to promote remyelination. However, direct injection of neural stem cells or oligodendrocyte precursor cells (OPCs) to the lesion site may not be an optimal therapeutic strategy since the viability and functionality of transplanted cells are compromised by the local hostile environment, e.g., in MS disease sites. There is an urgent need to find effective strategies to improve remyelination. In order to improve the viability of the transplanted cells, the microenvironments of the diseased tissue has to be re-conditioned for transplanted cells to survive. One way to manipulate the local microenvironment is to use an injectable neural biocompatible hydrogel system loaded with factors to provide a regeneration permissive microenvironment. To this end, hydrogels made of multi-arm polyethylene glycol (PEG) and modified short laminin peptide sequence were used as a carrier for cell transplantation. These hydrogel systems support remyelination. FIG. 8 shows that increased myelination occurred when OPCs are transplanted with these hydrogels

Example 8

Nanoparticles

FIGS. 9A-D show inhibition of collagen IV biosynthesis using dimethyloxalylglycine (DMOG) nanoparticles. (A)

Degradable nanoparticles loaded with DMOG. (B) Size distribution of DMOG-loaded nanoparticles (average size=45 nm). (C, D) Nanoparticles stained with anti-collagen IV antibody 4 weeks after the implantation of control nanoparticles (C) or nanoparticles containing DMOG (D). Scale bar=75 um. Dotted lines indicate the borders of implanted hollow fibers.

Example 9

Functional Outcomes after Application of Chitosan-Gelatin Hydrogel in a Rat Model of Severe Spinal Cord Injury The studies described herein employ a chitosan-gelatin hydrogel system. This hydrogel is non-neurotoxic and possesses the unique property of gelation at body temperature from its liquid form at room temperature. To maximize therapeutic benefits this hydrogel was loaded with glial derived neurotrophic factor (GDNF). The therapeutic effects of this hydrogel were tested in a rat model of severe acute spinal cord injury.

Fabrication of Chitosan-Gelatin Hydrogel

Chitosan and gelatin are two naturally occurring polymers. Chitosan is a polysaccharide formed by cross linkage of multiple monosaccharide units. It has active acetyl groups available for cross linkage. At acidic pH, chitosan is able to undergo polymerization. Gelatin is a peptide polymer and chemically derived from denatured collagen. It is a part of extracellular matrix and has been shown to be important for extracellular signaling. Chitosan and gelatin co-polymer can be created by mixing chitosan with gelatin using a standard and well known procedure that involves creating acidic pH for chitosan polymerization followed by mixing with heated and stirred gelatin solution. However there are two disadvantages of this approach—high osmolarity of the resultant solution (>500 mM) and acidic pH. There are also concerns for cytotoxicity to biological tissues at such high concentrations. These disadvantages render the use of this copolymer useless for clinical application, In the present invention, chitosan and gelatin were cross linked by two different approaches—the first was a covalent linkage using genipin followed by using ionic cross linkage using glycerol phosphate. Genipin is a plant derived cross linker and quite cheap. The safety and cytotoxic profile of genipin was evaluated and a concentration of 0.4 mM was found to be safe in the in vitro cell cultures. This concentration of genipin was added to chitosan and gelatin mixture. Genipin is able to covalently link both the saccharide and amine groups available in chitosan and gelatin, respectively. This creates a polysaccharide-peptide cross linkage. The addition of genipin offers the advantage of creating a stable co-polymer which is stable over a wide range of temperature. It is in liquid state at room temperature which renders it easy for therapeutic delivery. This copolymer can be easily stored in frozen state and autoclaved for biological applications. At the time of clinical application glycerol phosphate is added for ionic cross linkage. Various concentrations of glycerol phosphate can be utilized depending on the physical property desired. The representative concentrations can be 0.1 mg/ml to 100 mg/ml. Specifically the concentration of 3 mg/ml was tested for this study. Glycerol phosphate has active phosphate moieties that result in further cross linkage between chitosan and gelatin. This provides a clinically useful property of quick gelling of the hydrogel within 30 minutes at room temperature. The osmolarity of this co-polymer can be from about 150 mM to about 300 mM (e.g., 100 mM, 150 mM, 200 mM, 250 mM, 300 mM, 350 mM, 400 mM), which is desirable for clinical application.

GDNF was mixed in a concentration of 75 microgram per mL of hydrogel. Nonlimiting examples of the concentration of GDNF or other growth factor include about 25 microgram per mL to about 250 microgam per mL (e.g., about 25, 50, 75, 100, 125, 150, 175, 200, 225, 250 microgram per mL, etc.)

Chitosan and gelatin were mixed in varying ratios from 0.5-15 to 15-0.5. The ratio of 6:4 was chosen due to its facile gelling properties. The hydrogel polymer was prepared with a synergistic contribution of covalent and ionic crosslinking. A polymer solution was first cross linked via covalent bonds using genipin in low extent to allow easy flow, and then ionic cross linker, glycerol phosphate, was added to reach a facile gelling within about 30 minutes. Growth factor (GDNF) was loaded immediately after ionic cross linker was added.

Animals and Induction of Spinal Cord Injury

All animal experiments were conducted according to the established institutional protocol and NIH guidelines for animal studies. Adult, female Sprague Dawley (SD) rats were used in this study. T10 laminectomy was performed in a standard fashion and severe contusive spinal cord injury was induced with computer-controlled impactor. This technique has previously been shown to yield severe spinal cord injury (Horn et al. "The effects of intrathecal hypotension on tissue perfusion and pathophysiological outcome after acute spinal cord injury" *Neurosurg Focus* 25(5):E12 (2008)).

Animals were divided into one control and four experimental groups. The experimental groups received injection of hydrogel alone (N=10), injection of hydrogel with GDNF (N=8), topical application of hydrogel (N=10), and topical application of hydrogel mixed with GDNF (N=8). The injury only control group received no intervention (N=8). For the injection groups, pre mixed preparations of the hydrogel were injected slowly at the injury site. In the topical application groups, the dura was carefully opened and pre-mixed hydrogel was placed on the exposed surface of injured spinal cord. Post-procedure rats received standard post spinal cord injury care including nutritional support, adequate hydration, pain control, bladder expression three times a day and treatment of complications including urinary tract infections.

Histology and Immunohistochemistry

Animals were sacrificed after 8 weeks of observation. The spinal cord was carefully removed and fixed with paraformaldehyde. Post fixed samples were cut longitudinally and mounted on microscope slides. For immunostaining, sections were permeabilized and blocked with 4% normal goat serum. Primary antibodies were then applied overnight at 4° C. The following primary antibodies were used: REC-1, β-3 tubulin, glial fibrillary acidic protein (GFAP), myelin basic protein (MBP), human macrophage glycoprotein CD-68 and chondroitin sulfate proteoglycan (CSPG).

Assessment Of Functional Outcomes

Weekly behavioral assessments were carried out for 8 weeks. Two pre-trained researchers made independent observations about hind limb function. The animals were placed in an observation area with transparent walls and observed for approximately 2-4 minutes each. Functional improvement was measured using the Beattie, Breshnan, and Basso scale (BBB scale) (Basso et al. "A sensitive and reliable locomotor rating scale for open field testing in rats" (*J Neurotrauma* 12(1):1-21 (1995); Basso et al. "Graded histological and locomotor outcomes after spinal cord contusion using the NYU weight-drop device versus transaction" *Exp Neurol* 139 (2):244-256 (1996))

Data Analysis

The results from immunohistochemistry were qualitatively assessed and reported. Data were entered in Microsoft Excel® software and analyzed in SPSS® version 19 software. Mean (±SD) BBB scores were calculated for experimental and control groups.

Behavioral Scores

The contusion model consistently resulted in minimal recovery. The BBB scores of the hydrogel only group were similar to the scores in the control group implying that neither the hydrogel nor the method of administration had significant negative effects on functional recovery. The topical groups (topical and topical+GDNF) demonstrated partial recovery. The hydrogel with GDNF group resulted in maximum improvement consistently across 8 weeks.

Immunohistochemistry

Staining revealed decreased astrogliosis and preservation of axonal bridge at the injury epicenter.

Conclusions

In this study, functional recovery after severe contusion SCI in rats was demonstrated using a chitosan-gelatin hydrogel mixed with GDNF. Preservation of axons across the lesion epicenter may be a result of neuroprotection.

Example 10

Chitosan-Gelatin Hydrogel Based Delivery of Glial Derived Neurotrophic Factor Prevents Secondary Injury in a Rat Model of Severe Spinal Cord Injury Secondary injury results in exacerbation of axonal loss and poor functional recovery after spinal cord injury (SCI). A chitosan-gelatin hydrogel was designed for prevention and limitation of secondary injury. The histological and functional outcomes were evaluated after application of this hydrogel in a rat model of SCI.

Fabrication of Chitosan-Gelatin Hydrogel-Amounts

Chitosan and gelatin are mixed in ratios of gelatin/chitosan varying from 0.5:15 to 15:0.5. As described above a ratio of 6:4 was chosen due to favorable physical properties. Genipin and proanthocyanidin are used as covalent cross linkers while glycerol phosphate was used as the ionic cross linker. Genipin and proanthocyanidin are plant-derived and are much less toxic than most synthetic cross linkers. Glycerol phosphate is non-toxic as far as the osmolarity is controlled around physiological value. The injectable hydrogel was prepared with a synergic contribution of covalent and ionic crosslinkings. A polymer solution was first cross linked via covalent bonds in low extent that allows the system still flows easily, and then ionic cross linker is added to reach a facile gelling within about 30 minutes. Growth factors when included are loaded immediately after ionic cross linkers.

Animals and Induction of Spinal Cord Injury

All animal experiments were conducted according to the established institutional protocol and NIH guidelines for animal studies. 36 adult, female Sprague Dawley (SD) rats were used in this study. Rats were anesthetized with weight-based intra-peritoneal injection of 4% chloral hydrate. T10 laminectomy was performed in a standard fashion. Severe contusive spinal cord injury was induced with computer-controlled impactor with a velocity of 4 cm/sec with an impact depth of two millimeters. This technique has previously been shown to yield severe spinal cord injury.

Animals were divided into four experimental and two control groups. The experimental groups received injection of hydrogel alone (N=8), hydrogel injection with GDNF (N=6), topical application of hydrogel (N=7), and topical application of hydrogel mixed with GDNF (N=8). The injury only control group received no intervention (N=6), while the sham surgery group (N=1) underwent surgery without injury being induced. For the gel injection groups, pre mixed preparations of the hydrogel were injected at six different sites proximal, within and distal to the lesion bilaterally. By using 6 injection sites the maximal diffusion of the gel throughout the lesion site was ensured. To minimize injection related damage, the hydrogel was administered at a depth of 1 mm (assuming the average spinal cord diameter of 3 mm) at a rate of 10 µl/minute and single injection volume of 10 µl. The microinjector was carefully withdrawn following visual confirmation of gelation. In the topical application groups, after induction of injury, the dura was carefully opened and 60 µl of pre-mixed gel was placed on the exposed spinal cord. The wound was subsequently closed in multiple layers. After these procedures, rats received standard post spinal cord injury care including nutritional support, adequate hydration, pain control, bladder expression three times a day and treatment of complications including urinary tract infections.

Histology and Immunohistochemistry

Rats were sacrificed after eight weeks of observation. After induction of anesthesia with sevoflorane, the rats were trans cardially perfused initially with phosphate buffered saline (PBS) and then with 4% paraformyldehyde. The spinal cord was carefully removed and fixed with paraformayldehyde for 24 hours followed by 30% sucrose. Postfixed samples from the transplant site were cut longitudinally at the epicenter of the lesion and mounted with the cut surfaces facing down in TBS tissue freezing medium. Twenty um thick transverse sections were cut on a cryostat and mounted on microscope slides. For immunostaining, sections were permeabilized and blocked with 4% normal goat serum. Primary antibodies are then applied overnight at 4° C. The following primary antibodies are used: with REC-1, axonal regeneration with β-3 tubulin, astrogliosis with glial fibrillary acidic protein (GFAP), myelination with myelin basic protein (MBP), macrophages with CD-68 and scar tissue with chondroitin sulfate proteoglycan (CSPG). Alexa Fluor secondary antibodies, goat anti mouse, and rabbit 488, 594, and 647 are used at 1:400 (Invitrogen, Carlsbad, Calif.).

Assessment of Functional Outcomes

Behavioral assessments were carried out every week on the same day for 8 weeks following injury and intervention. Because discomfort immediately following surgery and complications associated with SCI can influence functional scores, the first behavioral assessment was carried out at the one week postoperative time point (Basso et al. "Behavioral testing after spinal cord injury: congruities, complexities, and controversies" *J Neurotrauma* 21(4):395-404 (2004). The time at which these assessments were conducted was maintained throughout the duration of the study in order to further standardize the assessment. Two pre-trained researchers made independent observations about hind limb function. The animals were placed in an observation area with transparent walls and observed for approximately 2-4 minutes each. A video recording was also carried out for future reference. Functional improvement was measured using the Beattie, Breshnan, and Basso scale (BBB scale).

Data Analysis

The results from immunohistochemistry were qualitatively assessed and reported. Data were entered in Microsoft Excel® software and analyzed in SPSS® version 19 software. Mean (±SD) BBB scores were calculated for experimental and control groups.

Animal Surgery and Survival

Most of the animals tolerated surgical procedures well, with approximately 90% rate of survival at 8 weeks follow up. Animals that seemed to develop discomfort from sores, or urinary tract infection were sacrificed prior to completion of the study and any data collected prior to sacrifice was excluded.

Immunohistochemistry

Inflammation, Astrogliosis, and Scar Formation

Preserved Axonal Bridge And Myelination Across the Injury Site

Angiogenesis

Behavioral Scores

The contusion model resulted in BBB scores around 1 to 2 yielding a consistent severe SCI model. Some animals demonstrated minor improvements at the first observation more than a week removed from surgery.

The BBB scores of the gel only group were similar to the scores of the control group implying that neither the gel nor the method of administration had significant negative effects on functional recovery. The topical groups (topical and topical+GDNF) demonstrated partial recovery with average BBB scores of 4 (95% CI 1.9-6.1) and 4.06 (95% CI 2.07-6.05) respectively. The hydrogel with GDNF group resulted in maximum improvement which was consistent across 8 weeks (BBB score of 4.33, 95% CI 1.88-6.78). This trend towards improvement was not statistically significant.

A trend towards improvement in hind limb function was observed in the experimental group that received GDNF mixed with chitosan-gelatin hydrogel. Three out of six animals showed movement in all three joints in this group as compared to one out of eight in gel only and one of out six in injury only groups. Although the improvement was gradual over the course of eight weeks, some animals showed significant improvement within the first 10-17 days. Release of neurotrophic factors from this hydrogel slowly over 4 weeks has been demonstrated. Preservation of axons across the lesion epicenter may be a result of both neuroprotection from secondary injury and regeneration.

In this investigation, prevention of axonal loss from secondary injury in a severe contusion spinal cord injury in rats using a chitosan-gelatin hydrogel mixed with GDNF was demonstrated.

A contusion model of severe spinal cord injury was used in this study because it closely emulates clinical presentation. Although a transection model yields consistent, severe spinal cord injury, it seldom represents the human spinal cord injury pattern. Axonal regeneration across the transection cavity proves the effectiveness of the experimental strategy in a lab setting, however the applicability of such results in a clinical setting is speculative. To ensure a uniform distribution of hydrogel, six injection sites proximal, distal, and within the lesion epicenter were selected. A potential disadvantage of multiple injections is the potential of further trauma and foreign body reaction. The microinjection was carried out very slowly at a depth of 1 mm to minimize such adverse reactions.

Example 11

Functional Outcomes after Injection of Chitosan-Gelatin Hydrogel in a Rat Model of Severe Spinal Cord Injury Introduction Functional recovery after severe spinal cord injury is modest due to inhibition of axonal regeneration by several intrinsic factors. Poor axonal regeneration results in limited functional improvement after spinal cord injury. An injectable chitosan-gelatin hydrogel was developed for delivery of neurotrophic factors and/or supporting cells and for enhancement of delivery of neurotrophic factors for axonal regeneration. The functional outcomes were evaluated after injection of this hydrogel in rat model of severe spinal cord injury.

Methods

Twenty eight adult SD rats were randomly assigned to two control (sham surgery (N=2), spinal cord injury only (N=6)) and three experimental groups (hydrogel injection (N=8); hydrogel with GDNF injection (N=6); hydrogel, GDNF and oligodendrocyte precursor cell (OPC) injection (N=6)). Spinal cord injury was induced by a computer controlled impactor with a diameter of 3 mm and depth of 2 mm at a speed of 4 cm/sec. 10 μL of hydrogel solution was administered by injection at six different points bilaterally distal, proximal and within the injury site slowly over one minute. All animals were followed for 8 weeks and weekly behavioral testing was performed using the BBB scale (minimum 0, maximum 21). Subsequently animals were sacrificed and spinal cords removed for studying axonal regeneration and myelination. Immunohistochemical staining with REC-1 (vascularization), 13-3 tubulin (axonal regeneration), GFAP (astrogliosis) MBP (myelination) and CD-68 (macrophage) was performed.

Results

Figure 10:
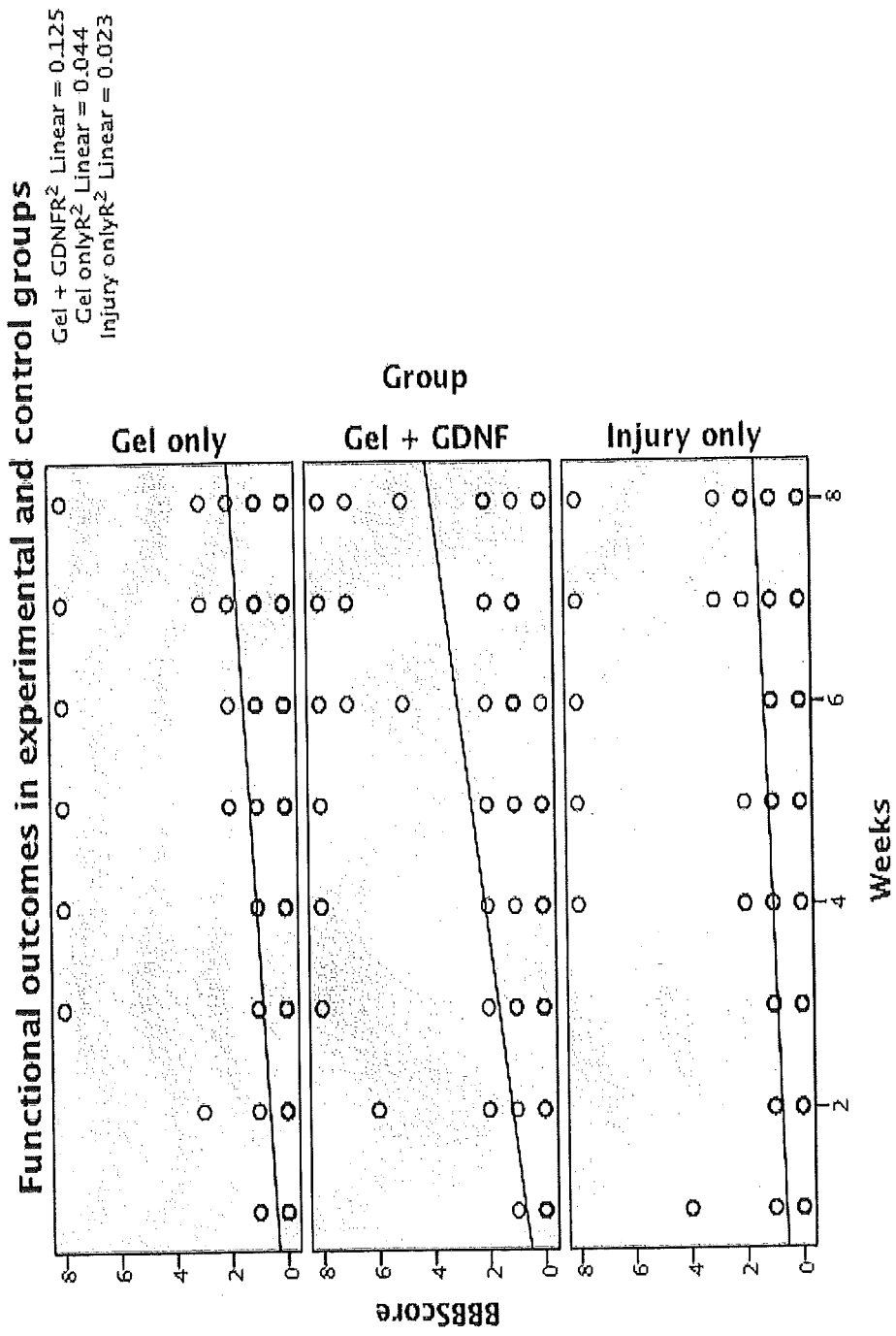
FIG. 10. Scatter plots depicting functional outcomes.
Figure 11:
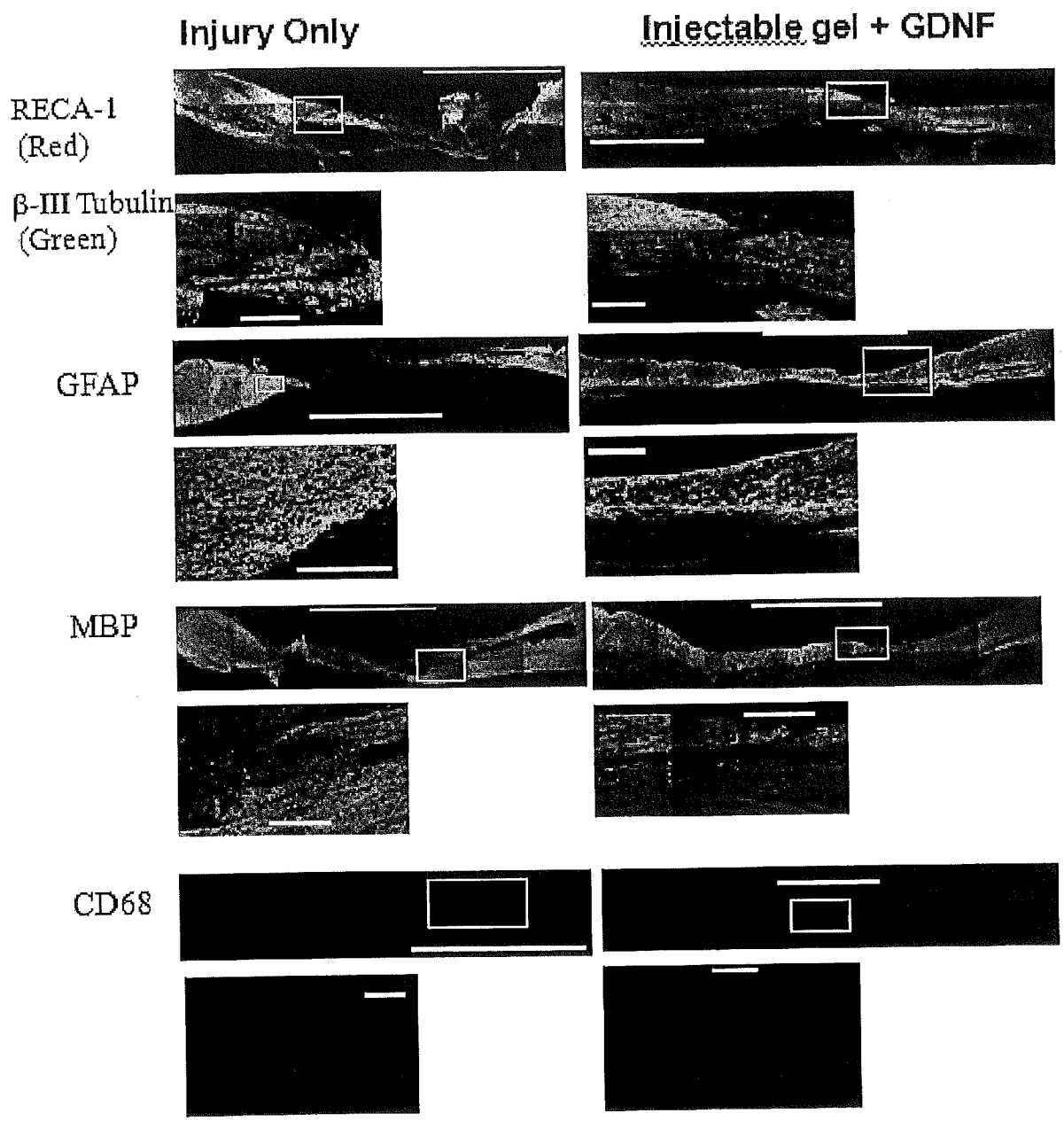
FIG. 11. Immunostaining of control and gel with GDNF groups.

The mean BBB scores (FIG. 10) for control group at eight weeks was 1.67 (95% CI 0.39-2.95). The hydrogel injection did not seem to adversely affect functional recovery (BBB score of gel only group—1.56 (95% CI 0.26-2.86)). The functional score improved with the inclusion of GDNF (BBB score—4.33 (95% CI 1.88-6.78)) but not with simultaneous inclusion of GDNF and OPCs (1.75, 95% CI—0.05-3.1). GDNF in the gel preparation results in preservation of tissue bridge across the injury site (FIG. 11). This bridge has abundant blood vessels and astrocytes. Myelinated axons were observed as well. Although there is evidence of inflammation it appears to be lesser than the control group.

Conclusions

The chitosan-gelatin based injectable hydrogel medium improves functional outcomes when combined with GDNF in a rat model of severe spinal cord injury. Preservation of supporting environment (blood vessels and astrocytes) and decreased inflammation appear to be primary mechanisms of improved functional outcomes.

Example 12

Functional Outcomes after Topical Application of Chitosan-Gelatin Hydrogel for in a Rat Model of Severe Spinal Cord Injury Introduction Functional recovery after severe spinal cord injury is modest due to inhibition of axonal regeneration by several intrinsic factors. Loss of axonal membrane integrity results in significant neuronal loss after spinal cord injury. A topical chitosan-gelatin hydrogel was designed for stabilizing the damaged axonal membrane and simultaneously delivering neurotrophic factors. The effects of this hydrogel were tested in rat model of severe spinal cord injury.

Methods

Figure 12:
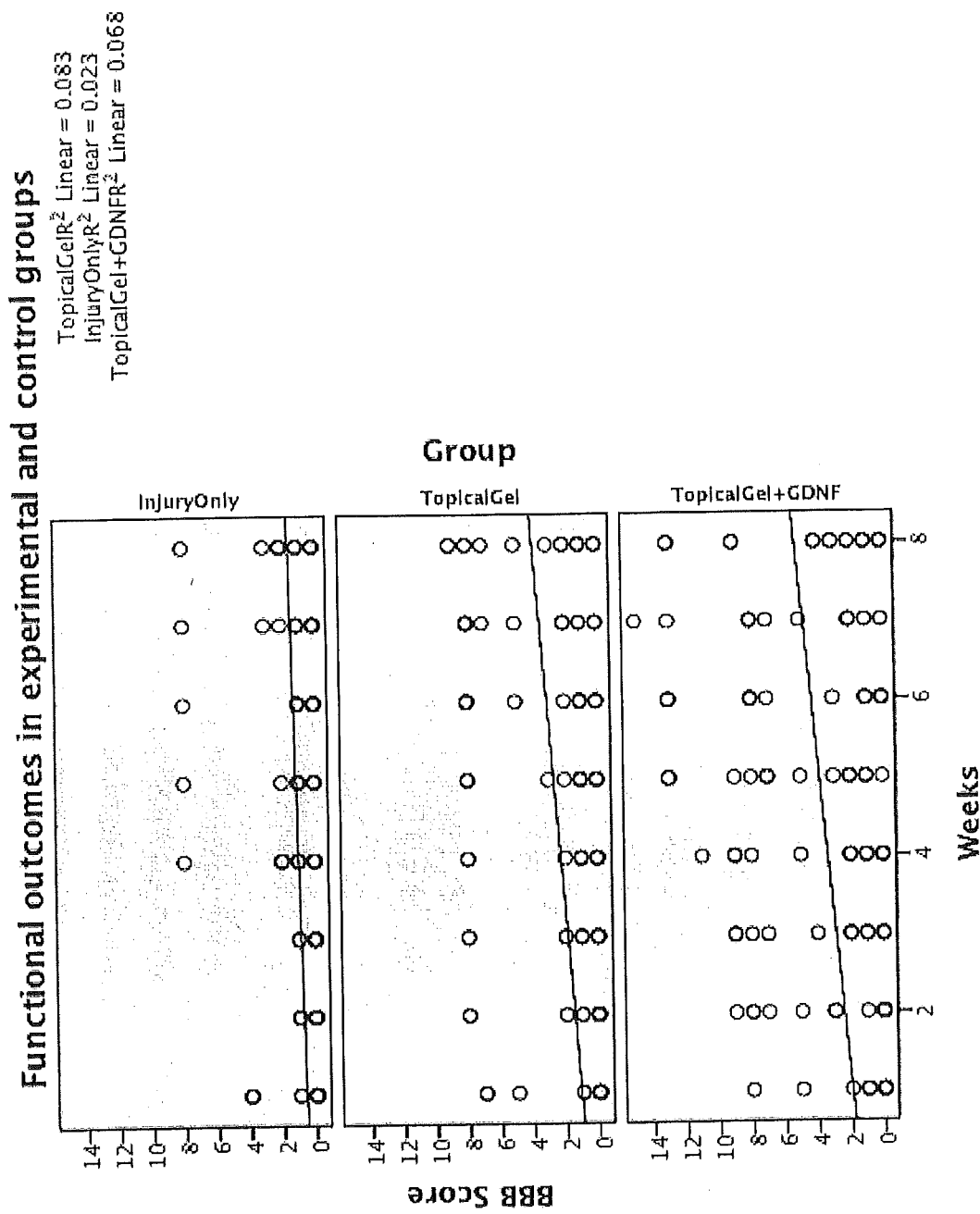
FIG. 12. Scatter plots depicting functional outcomes.
Figure 13:
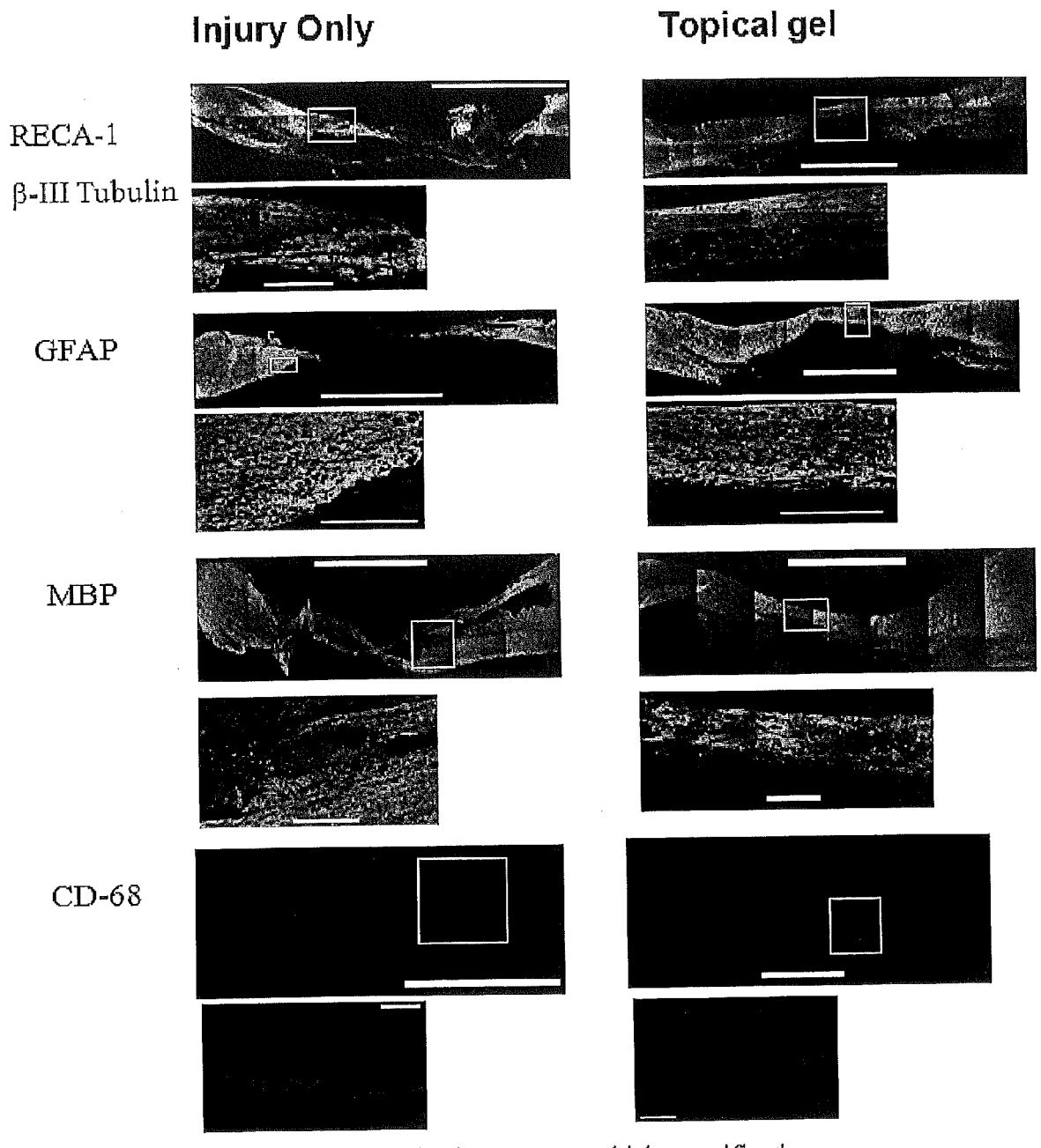
FIG. 13. Immunostaining in control and topical gel groups.

Twenty three adult SD rats were randomly assigned to two control (sham surgery (N=2), spinal cord injury only (N=6)) and two experimental groups (topical hydrogel application (N=7) and topical hydrogel with GDNF (N=8)). Spinal cord injury was induced by a computer controlled impactor with a diameter of 3 mm and depth of 2 mm at a speed of 4 cm/sec. The dura was opened widely to expose the injured segment. 60 µL of hydrogel solution was topically administered and allowed to gelate before closure. All animals were followed for 8 weeks and weekly behavioral testing was performed using the BBB scale (minimum 0, maximum 21). Subsequently animals were sacrificed and spinal cords removed for studying axonal regeneration and myelination. Immunohistochemical staining was performed to study vascularization (REC-1), axonal regeneration (β-3 tubulin), astrogliosis (GFAP), myelination (MBP) and inflammation (CD-68).
Results Improvement in BBB scores was observed in treatment groups as early as the first week (FIG. 12). The mean BBB scores for control group at eight weeks was 1.67 (95% CI 0.39-2.95). The topical hydrogel application significantly improved functional recovery (BBB score of topical gel group—4 (95% CI 1.9-6.1). The functional scores were comparable after the inclusion of GDNF (BBB score—4.06 (95% CI 2.07-6.05)). Immunostaining (FIG. 13) demonstrates a tissue bridge with abundant blood vessels and myelinated axons across the injury area. Although there is evidence of inflammation in the tissue bridge the distribution of astrocytes is relatively uniform and is comparable to sham animals.
Conclusions The topical chitosan-gelatin topical hydrogel improves functional outcomes when used alone or in combination with GDNF after severe spinal cord injury in rats. This treatment strategy appears to preserve axons across injury site and prevent the formation of astroglial scar. Decreased astrogliosis and scar formation; preservation of axons, vasculature and myelination across the injury epicenter; and increased regeneration across the injury epicenter were all observed with topical hydrogel application. Topical application of hydrogel improved hind limb function in rats after 8 weeks follow up.

Example 13

Functional Outcomes after Application of Chitosan-Gelatin Hydrogel in a Rat Model of Severe Spinal Cord Injury Introduction A thermo-sensitive, biodegradable chitosan-gelatin hydrogel for neuroprotection and growth factor delivery after neurotrauma was designed. The functional outcomes were evaluated after application of the hydrogel in a rat model of severe spinal cord injury.
Methods Adult SD rats were randomly assigned to a control (spinal cord injury only) and four experimental groups (hydrogel injection, hydrogel with GDNF injection, topical hydrogel and topical hydrogel with GDNF). Severe spinal cord injury was induced by a computer-controlled impactor. In the injection group, hydrogel solution was administered slowly within the injury site while it was placed on the cord surface in the topical group. All animals were followed for 8 weeks and weekly behavioral testing was performed using the BBB scale (minimum 0, maximum 21). Immunohistochemistry was performed to study scar formation and tissue preservation.
Results The application of hydrogel did not adversely affect the functional outcomes. The BBB scores were better in the topical group as compared to the injection group. Inclusion of GDNF, both in topical and injection groups, appears to improve functional outcomes. Immunohistochemistry revealed preservation of neuronal bridge across the injury epicenter.
Conclusion The application of chitosan-gelatin hydrogel improves functional outcomes when combined with GDNF in a rat model of severe spinal cord injury.

Example 14

Engineering an In Situ Crosslinkable Hydrogel for Enhanced Remyelination

Introduction.

Demyelination is the pathological process in which myelin sheaths are lost from around axons. The loss of myelin sheaths is associated with conduction block, progressive axonal and neuronal loss, and functional deficits. In addition to focal demyelinating diseases, such as multiple sclerosis (MS), and leukodystrophies, axonal demyelination is an inevitable component in many types of neural tissue injury, including spinal cord injury, and traumatic brain injury. Remyelination has to occur in order to cure these diseases, and to fully regenerate injured spinal cords or brain tissues.

At present, there are no effective therapies that promote remyelination. Existing immunosuppressive and immunomodulatory treatments have little efficacy in either preventing long-term disability or in restoring lost functions[1]. Since remyelination involves the generation of new mature oligodendrocytes, current research strategies for remyelination in animal models have been focused on oligodendrogenic stem/precursor cells of both endogenous and exogenous origins[2, 3]. Previous studies on the role of oligodendrocytes and oligodendrocyte progenitors in CNS remyelination have evidenced the dominant contribution of oligodendrocyte precursor cells (OPCs) to remyelinate spinal cord lesions. Although spontaneous remyelination mediated by endogenous OPCs can be a highly effective regenerative process, this response is incomplete and fails over time due to the limited availability, migratory capacity, and myelinating ability[4,5]. In contrast, cell transplantation (exogenous therapies) using glial cell lineages or precursors including OPCs[6], induced pluripotent stem cells[7], mesenchymal stem cells[8], neural stem cells[9], embryonic stem cell-derived precursors[10], and olfactory ensheathing cells[11], have all been shown to achieve some remyelination in demyelinated adult CNS.

The fate of transplanted cells is strongly influenced by the type of diseases/injuries and local microenvironmental signals (biomechanical and biomolecular signals). As to remyelination failure, the scarring and inflammatory tissue environment at the demyelinating site may be deleterious to the survival and directed differentiation of transplanted cells with the presence of differentiation block of oligodendroglial progenitors in chronic MS lesions[1, 2, 5, 14-16]. Control over stem cell trafficking, survival, proliferation, and differentiation within a complex demyelinating in vivo milieu continues to be extremely challenging.

Figure 14:
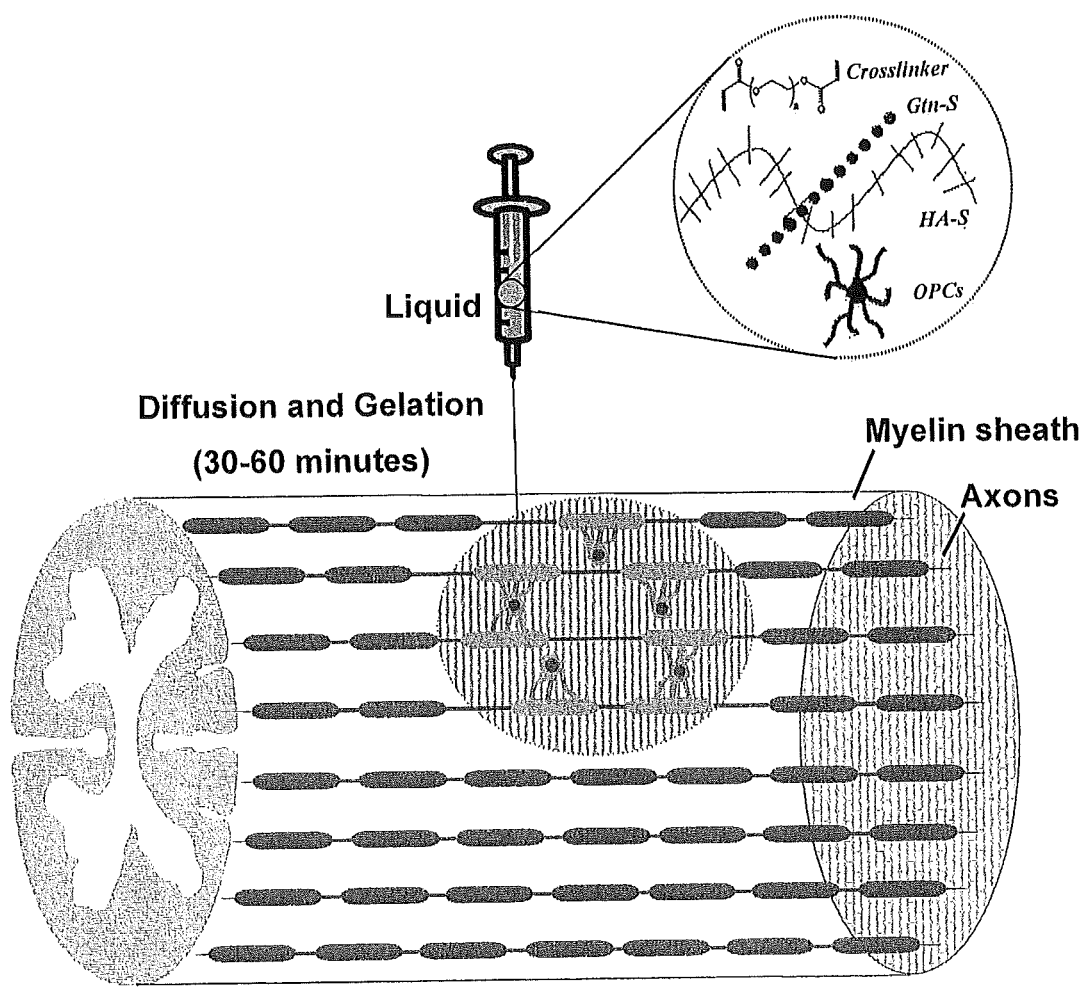
FIG. 14. Schematic drawing of OPCs transplanted with in-situ crosslinkable hydrogels for spinal cord remyelination.

The overall objective of this study was to engineer an injectable biocompatible hydrogel system as a supportive niche to provide a regeneration permissive microenvironment for transplanted OPCs to survive, functionally differentiate, and remyelinate central nervous system (CNS) lesions. The system employs a highly biocompatible hydrogel, based on thiol functionalized hyaluronic acid (HA-S) and thiol functionalized human recombinant gelatin (Gtn-S), which can be crosslinked by poly(ethylene glycol)diacrylate (PEGDA) through Michael-type addition reaction. This hydrogel system was engineered regarding cell adhesive properties and mechanical properties to best support the growth properties of OPCs in culture. Transplanted OPCs with the hydrogels optimized in vitro exhibited enhanced survival, and oligodendrogenic differentiation, and were able to remyelinate demyelinated axons inside ethidium bromide (EB) demyelination lesion in adult spinal cord. The schematic drawing of OPCs transplanted with in-situ crosslinkable hydrogels for spinal cord remyelination is shown in FIG. 14. This study demonstrates extensive remyelination with transplanted stem cells and provides a new treatment for demyelination-related diseases and CNS injuries in which cell therapies may be beneficial.

Mechanical Property of Hydrogel.

Figure 15:
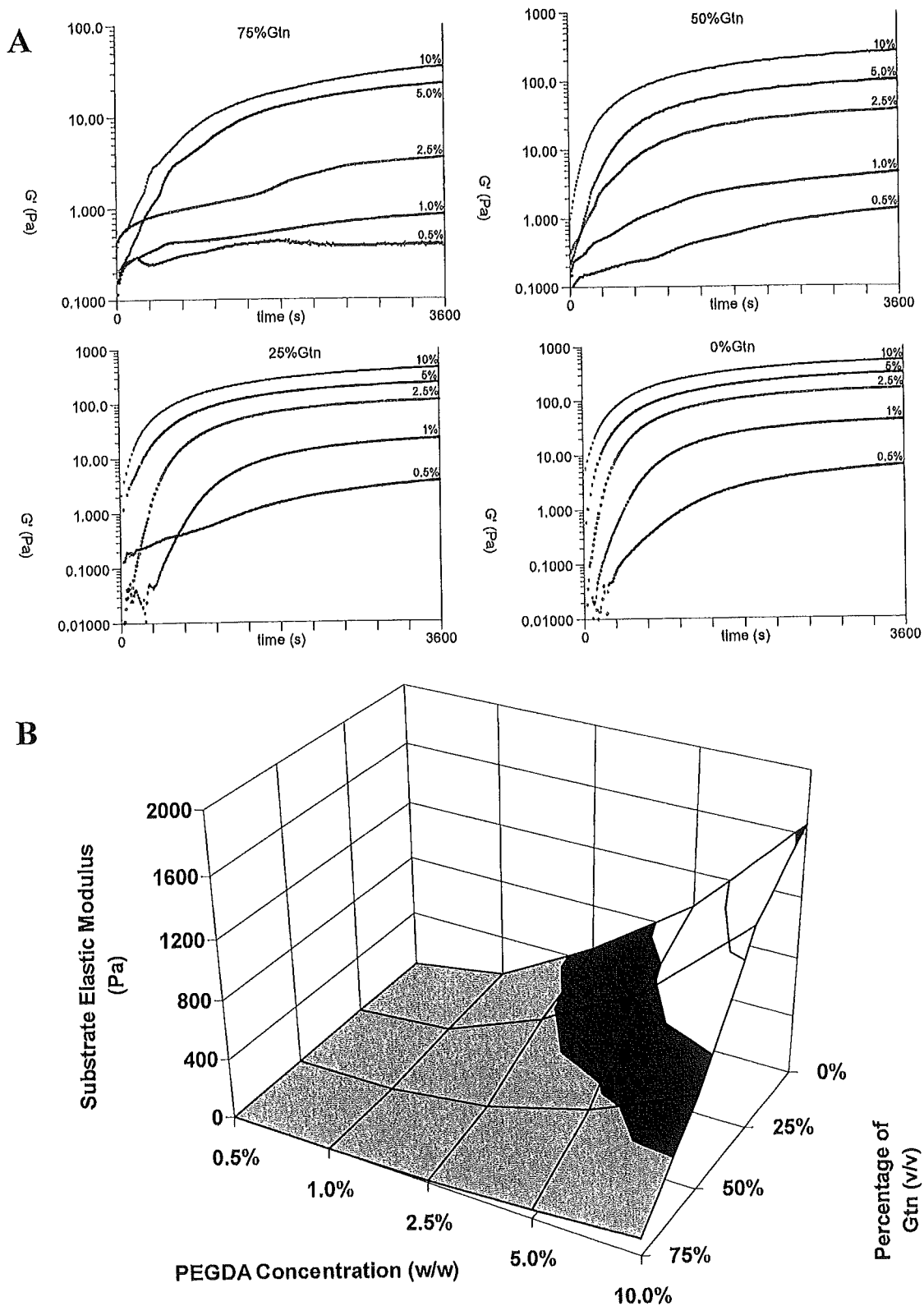
FIGS. 15A-15B. (A) Time sweep of G' as a function of PEGDA concentration (10%, 5%, 2.5%, 1% and 0.5%) and Gtn-S percentage (75%, 50%, 25%, and 0%). (B) the elastic modulus of the hydrogel as a function of PEGDA concentration and Gtn-S percentage.

To develop CNS-compatible hydrogels to be used as cell carriers in the adult CNS, it is appropriate to ensure the mechanical compliance of the hydrogels with native CNS tissue. The storage modulus (G') of rat CNS is about 40 Pa or elastic modulus (E') of around 120 Pa as characterized by rheometer. Note that the storage modulus G' always exceeds the loss modulus G", indicating that the adult rat CNS has an elasticity-dominant rather than viscosity-dominant mechanical property, which is in agreement with previous studies[24]. The mechanical properties of this hydrogel system can be controlled by varying a couple of parameters, such as the concentrations of HA-S and Gtn-S, the ratio of HA-S to Gtn-S, PEGDA concentration, and so on. In this study, the effects of two parameters, i.e., Gtn-S percentage, and PEGDA concentration on hydrogel properties and OPC behaviors are examined. Each of the two parameters was examined independently while keeping other variables constant. By varying the gelatin percentages, or PEGDA concentrations, hydrogels with elastic modulus ranging from 1 Pa to 1600 Pa, which spans the range of that of native CNS tissue (120 Pa), can be achieved (FIG. 15). The gelatin percentage and PEGDA concentration exhibited opposing effects on the hydrogel elastic modulus, i.e., E' increases as a function of decreasing Gtn-S percentage, whereas E' increases with increasing PEGDA concentration. Since PEGDA acts as the crosslinker for the hydrogel system, E' increases with the increasing PEGDA concentration. The cell adhesive component in the hydrogel, Gtn-S, contributes to the viscosity rather than the elasticity of the hydrogels.

Optimizing Hydrogels for OPCs Culture.

Extracellular matrix (ECM) is an important component for the stem cell niche and regulating stem cell behavior and functions. Biomaterials can be used to create a niche to support stem cell survival in vivo by providing the biochemical and biomechanical environments for the tissues to be regenerated. Hyaluronic acid (HA) is an important EMC component for CNS tissues. Inclusion of HA imparts hydrophilic network structures to the hydrogels. However, HA is extremely hydrophilic and polyanionic, which prevents cell attachment and limits its ability to support cell growth and tissue remodeling. To promote cell growth and function, cell adhesive component, human recombinant gelatin, was incorporated in the hydrogel. The effect of biochemical and biomechanical properties of the hydrogels on OPC attachment, proliferation, and directed differentiation were examined in vitro and in vivo.

Figure 16:
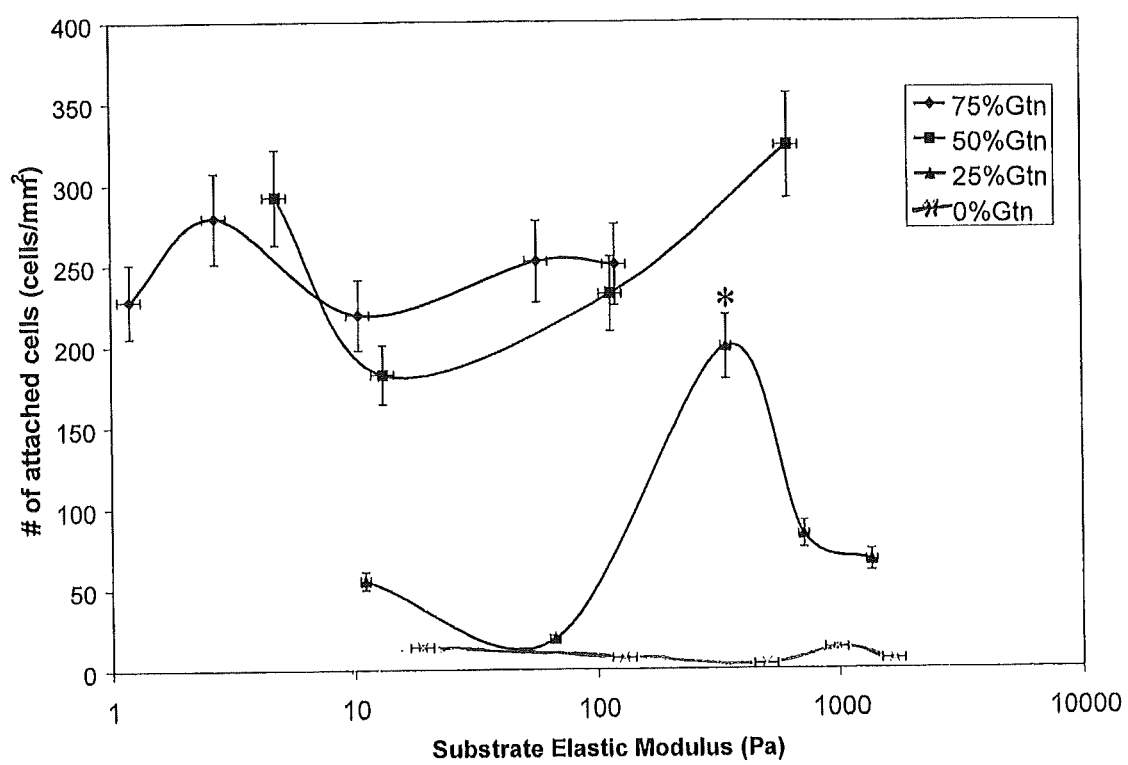
FIG. 16. The numbers of attached OPCs on the surfaces of the hydrogels as a function of hydrogel elastic modulus and Gtn-S content. On the hydrogels with 25% GTn-S, OPCs preferred to attach on hydrogels of medium stiffness ($*P<0.05$).

The effect of the adhesive component Gtn-S in the hydrogels on OPC behavior, such as attachment, morphology, and proliferation, was evaluated by culturing OPCs on the surfaces of the hydrogels with different gelatin content and elastic modulus. When compared to that of the elastic modulus, Gtn-S content in the hydrogels exerted greater effect on cell attachment, as evidenced by magnitude-higher numbers of attached OPCs on hydrogels with high Gtn-S content (exceeding 50%) relative to those with low Gtn-S content (FIG. 16). At low Gtn-S percentages (25%), the numbers of attached OPCs were dependent on hydrogel elastic modulus, manifested by the appearance of a peak on the curve. In comparison, at high Gtn-S percentages (50%), OPC attachment was independent of the elastic modulus with the curves almost flattened over the elastic modulus. These results suggest that when adhesive components present at sufficiently high percentages in the hydrogels, cell adhesive component may dominate over material mechanical properties and dictate cell attachment. There was no significant difference in OPC attachment between the 50% and 75% gelatin groups, perhaps due to the saturation in the presentation of surface binding domains by high-percentage Gtn-S in the hydrogels. Given the range of elastic modulus achieved with each value of gelatin percentage, OPC attachment was best favored on the surfaces of the hydrogels with 50% Gtn-S.

Parallel investigations of the morphologies of attached OPCs on hydrogels of the same elastic modulus (10 Pa) but with different gelatin percentages revealed no significant difference among the groups. All the attached cells displayed spreading cytoskeletons (red is the staining for A2B5, a specific surface marker for OPCs). The proliferation of attached OPCs on hydrogel surfaces was examined using Click iT-EdU kit. All the attached OPCs on the hydrogel surfaces were stained in red using PI, while the proliferating OPCs were stained in blue using Click iT-EdU 647. Regardless of the gelatin percentage, attached OPCs exhibited an approximate 5% proliferation rate (blue to red cell ratio).

Hydrogel Stiffness Affects Cell Behaviors.

OPCs were cultured on the surfaces and inside the hydrogels, representing 2D and 3D culture conditions, respectively. At 3 days in 2D culture (on the surfaces of the hydrogels), OPCs exhibited a biphasic change in morphology over increasing elastic modulus of the hydrogels. On soft hydrogels (4.8 Pa and 13.8 Pa), OPCs displayed round morphology with very few spreading processes. On hydrogels of medium stiffness (116 Pa), OPCs were primarily spreading resembling the natural morphology of OPCs in the body, which is important for oligodendrocytes to spirally enwrap axons, forming multi-lamellar myelin sheaths. On stiff hydrogels (624 Pa), cell spreading was diminished over hydrogel stiffness with OPCs assuming round morphology in cell aggregates. A similar trend of biphasic change was observed in cell morphology vs. hydrogel stiffness at 7 days in 2D culture. OPCs were increasingly spreading with sprouting processes within low to medium range of hydrogel elastic modulus, and were then progressively aggregated and assumed round morphology within medium to high range of hydrogel elastic modulus.

In parallel, OPCs survived in 3D culture (i.e., inside the hydrogels). The viability of OPCs was high (>98%) regardless of the hydrogel elastic modulus (4.8 Pa, 13.8 Pa, 116 Pa, 312 Pa and 624 Pa tested). However, OPCs expressed normal oligo-morphology with hydrogel elastic modulus less than 120 Pa. Hydrogels with higher elastic modulus led to spherical structures of OPCs without sprouting processes. These hydrogels may be too stiff to allow processes sprouting and extension for the OPCs[25].

Cell adhesion and proliferation are important indices to evaluate the appropriateness of a cell carrier to support cell functions. As a function of the hydrogel elastic modulus, the proliferation rate of cultured OPCs on the surfaces of the hydrogels increased when the modulus is lower than 120 Pa and decreased when the modulus is greater than 120 Pa.

Hydrogel with a 120 Pa elastic modulus, which is close to that of native CNS tissue, best supports OPC proliferation.

OPC Transplantation with Optimized Hydrogels as Carrier.

OPCs are most often referred to as a population of adult CNS stem/precursor cells that are capable of differentiating into mature oligodendrocytes[26]. Lines of evidence on the contribution of OPCs as the major source of remyelinating oligodendrocytes have come from studies through in vivo tracing of both endogenous OPCs[4,27] and transplanted OPCs. Complementary studies on mature oligodendrocytes have suggested their inability to contribute to remyelination in adult CNS, further supporting the role of OPCs as the primary cell source for functional remyelination. To remyelinate the axons, OPCs have to establish contact with the axon to be remyelinated, express myelin genes, and form a myelin membrane which then ensheaths the axon. In addition to a deficiency of differentiation-inducing factors, a demyelinating tissue environment presents inhibitory factors that are responsible for differentiation failure[15, 28]. The demyelination model was established by the injection of EB at the left ventrolateral funiculus of the rat spinal cords, which leaves a population of demyelinated axons in a glial-depleted environment. OPCs were transplanted to the EB demyelinated lesion area in two treatment groups, i.e., OPCs only, and OPCs with optimized hydrogel carrier. When compared to the untreated control group (demyelinated lesion+saline injection) in which the demyelinated area remained as a substantial cavity, both treatment groups displayed cell populations at the lesion site, as evidenced by the presence of cell nuclei. In particular, the lesion site in the OPCs with optimized hydrogel group was much more densely repopulated by myelin basic protein (MBP)-positive oligodendrocytes (indicated by the presence of numerous circle-shaped MBP-positive structures typical of normal myelination) when compared to that in the OPCs only treatment group, where very few MBP-positive cells were seen within the lesion site. A few GFAP-positive astrocytes were seen in both treatment groups. The absence of cells at the lesion site in the untreated control suggests that the cells seen at the lesion in the two treatment groups were primarily transplanted cells rather than of endogenous origin. The hydrogel carrier has protected transplanted OPCs within a hostile demyelinated lesion environment for better survival and overcomes environmental cues that normally restrict the differentiation potential of transplanted OPCs, which may have facilitated OPCs differentiation into mature oligodendrocytes.

Conclusions.

A hydrogel system has been developed as a candidate material for OPC niche formation. This study demonstrates extensive remyelination with transplanted stem cells in vivo. The hydrogel harnesses the potential of exogenous OPCs for CNS remyelination by promoting the survival, attachment, natural morphology, proliferation, oligodendrogenic differentiation, and myelin formation of transplanted OPCs in a demyelinated CNS lesion environment. This work exemplifies the efforts to develop material equivalents to the stem/precursor cell niche through engineering strategies based upon an integration of material properties with neural compatible biochemical and biomechanical properties. This study demonstrates the engineering of neural compatible hydrogels as a niche for OPCs to promote remyelination in vivo. The results indicate that human recombinant gelatin benefits OPC attachment without significant effect on OPC proliferation and morphology. Hydrogel elastic modulus affects the overall cell morphology and an optimal range of elastic modulus exists that best supports the natural oligo-morphology, and proliferation of OPCs in both 2D and 3D cultures. OPCs transplanted with hydrogels optimized with cell adhesive properties and mechanical properties as determined in the in vitro experiments exhibited enhanced survival, oligodendrogenic differentiation, and the ability to remyelinate demyelinated axons inside demyelination lesion in adult spinal cord. This study provides a new therapeutic approach to treat demyelination related diseases and other trauma/disease conditions in which cell therapies may be beneficial or essential.

In-Situ Crosslinkable Hydrogels and Rheological Testing.

To test the mechanical properties of the formed hydrogel series, HA-S solution (1% w/v, Glycosan BioSystems Inc. Salt Lake City, Utah) and Gtn-S solution (1% w/v, different Gtn ratio: 75%, 50%, 25% and 0%) with varying PEGDA concentrations (10%, 5%, 2.5%, 1%, and 0.5%) were inspected with oscillatory shear rheometer AR 1000 (TA Instruments Inc.). The time sweep was performed to monitor the in situ gelation at 37° C., recording the temporal evolution of shear storage modulus, G' and the shear loss modulus, G". Frequency sweep tests are used to obtain information about the stability of hydrogel structures[29]. The stress sweep was set up by holding the frequency 1 Hz constant while increasing the stress level from 1 to 10 Pa. The applied range of 1-10 Pa was found to be safe-for-use from a prior experiment where the linear viscoelastic region (LVR) profiles of the hydrogels were determined by shearing them until structural breakdown. Oscillatory stress sweep allows determination of G' of hydrogels. The elastic modulus, E', can be evaluated by E' 2G' (1+γ). When a material can be assumed to be incompressible, its Poisson's ratio, γ, approaches 0.5 and this relationship approaches E'=3G'. This assumption for hydrogels is supported by research showing that n for polyacrylamide hydrogels is nearly 0.5, and because these hydrogels are typically used under very low strain conditions[30]. In addition to using a rheometer to test the mechanical properties of hydrogels, fresh adult rat CNS tissues were examined by rheometer using the same rheological protocol.

OPC Culture.

Oligodendrocyte progenitor cells (OPCs, CG4 cell[31]) were maintained with serum-free growth medium supplemented with platelet-derived growth factor (PDGF, 10 ng/mL) and fibroblast growth factor 2 (FGF2, 10 ng/mL). For 2D culture, OPCs were seeded on the surface of hydrogels at $5\times10^3$ cells/cm$^2$. For 3D culture, $1\times10^4$ cells/mL were mixed into the hydrogels.

Cell Viability.

Viability of cells was examined using a LIVE/DEAD Viability Kit (L-7013, Molecular Probes). Live cells were stained with green fluorescent SYTO 10; and dead cells with compromised cell membranes were stained with red fluorescent ethidium homodimer-2.

Cell Morphology.

Morphology of cells was examined by immunocytochemistry. The OPCs were fixed, stained with A2B5 (MsIgM, ab5321, abeam) and 4',6-Diamidino-2-Phenylindole, Dihydrochloride (DAPI, Molecular Probes), and visualized with a Leica TCS SP5 laser scanning confocal microscope. For each well, 5 images are taken from different regions.

Cell Adhesion and Proliferation.

Proliferation of cells was examined using Click iT-EdU cell proliferation assay (C10085, Invitrogen). The total attached cells were detected by PI staining. The samples were imaged using a Leica TCS SP5 laser scanning confocal microscope. For each well, five images were taken from different regions. The percentage of EdU cells in the population was calculated and compared among groups.

Demyelinating Lesion and Transplantation of OPCs.

An experimental model of toxin-induced focal demyelination using ethidium bromide (EB) to demyelinate specific CNS tracts in a dose-dependent manner[32] was used. A total of 21 female nude rats (150-200 g, Charles River Laboratories) were used throughout the study. The EB model of focal demyelination induced by injecting EB at left ventral white matter of the thoracic spinal cord was conducted as previously described. All transplantations were performed 7 day post-surgery. Following induction of anesthesia, T8/T9 laminectomy site was re-exposed. OPCs ($1\times10^5$ cells/uL) were transplanted in two treatment groups: (1) OPCs only, (2) OPCs with optimized hydrogels. OPCs were delivered at a rate of 0.5 μL/min directly into the EB lesion using the stereotactic coordinates.

Tissue Processing and Immunohistochemistry.

To evaluate OPCs transplanted following demyelination, animals were sacrificed at 4 weeks post transplantation. 20 μm thick transverse sections were cut and stained with glial fibrillary acidic protein (GFAP) for astrocytes (1:1000; Dako), myelin basic protein (MBP) for mature oligodendrocytes (1:500, abcam), and β III tubulin for axons (1:1000; Sigma). The specimens were imaged using a Leica TCS SP5 laser scanning confocal microscope.

Statistical Analysis.

Data were presented as the mean±the standard error of mean for each group. One-way analysis of variance (ANOVA) was performed to determine the effect of hydrogel property and hydrogel use on the outcome using SPSS software. Statistical significance is accepted at $P<0.05$.

References for Example 14

[1] T. Ben-Hur, S. A. Goldman, *Ann. N.Y. Acad. Sci.* 2008, 1142, 218.

[2] J. Yang, A. Rostami, G. X. Zhang, *J. Neurol. Sci.* 2009, 276, 1.

[3] J. Jadasz, L. Aigner, F. Rivera, P. Küry, *Cell Tissue Res.* 2012.

[4] B. E. Deverman, P. H. Patterson, *J. Neurosci.* 2012, 32, 2100.

[5] M. R. Kotter, C. Stadelmann, H.-P. Hartung, *Brain* 2011, 134, 1882.

[6] Q. Cao, Q. He, Y. Wang, X. Cheng, R. M. Howard, Y. Zhang, W. H. DeVries, C. B. Shields, D. S. K. Magnuson, X.-M. Xu, D. H. Kim, S. R. Whittemore, *J. Neurosci.* 2010, 30, 2989.

[7] a Tsuji, K. Miura, Y. Okada, K. Fujiyoshi, M. Mukaino, N. Nagoshi, K. Kitamura, G. Kumagai, M. Nishino, S. Tomisato, H. Higashi, T. Nagai, H. Katoh, K. Kohda, Y. Matsuzaki, M. Yuzaki, E. Ikeda, Y. Toyama, M. Nakamura, S. Yamanaka, H. Okano, *PNAS* 2010, 107, 12704.

[8] D. Gordon, G. Pavlovska, J. B. Uney, D. C. Wraith, N. J. Scolding, *Neuropathol. Exp. Neurol.* 2010, 69, 1087.

[9] O. Einstein, Y. Friedman-Levi, N. Grigoriadis, T. Ben-Hur, *J. Neurosci.* 2009, 29, 15694.

[10] M. Aharonowiz, O. Einstein, N. Fainstein, H. Lassmann, B. Reubinoff, T. Ben-Hur, *PLoS ONE* 2008, 3, e3145.

[11] M. Sasaki, K. L. Lankford, C. Radtke, O. Honmou, J. D. Kocsis, *Exp. Neurol.* 2011, 229, 88.

[12] T. Kuhlmann, V. Miron, Q. Cuo, C. Wegner, J. Antel, W. Bruck, *Brain* 2008, 131, 1749.

[13] E.-M. Hur, I. H. Yang, D.-H. Kim, J. Byun, Saijilafu, W.-L. Xu, P. R. Nicovich, R. Cheong, A. Levchenko, N. Thakor, F.-Q. Zhou, *PNAS* 2011, 108, 5057.

[14] M. Zawadzka, R. J. M. Franklin, *Curr. Opin. Neurol.* 2007, 20, 294.

[15] Y. Wang, X. Cheng, Q. He, Y. Zheng, D. H. Kim, S. R. Whittemore, Q. L. Cao, *J. Neurosci.* 2011, 31, 6053.

[16] K. S. Carbajal, C. Schaumburg, R. Strieter, J. Kane, T. E. Lane, *PNAS* 2010, 107, 11068.

[17] M. C. Cushing, K. S. Anseth, *Science* 2007, 316, 1133.

[18] D. E. Discher, D. J. Mooney, P. W. Zandstra, *Science* 2009, 324, 1673.

[19] A. Mammoto, K. M. Connor, T. Mammoto, C. W. Yung, D. Huh, C. M. Aderman, G. Mostoslaysky, L. E. H. Smith, D. E. Ingber, *Nature* 2009, 457, 1103.

[20] M. W. Tibbitt, K. S. Anseth, *Biotechnol. Bioeng.* 2009, 103, 655.

[21] R. A. Marklein, J. A. Burdick, *Adv. Mater.* 2010, 12, 175.

[22] Z. Liu, H. Wang, Y. Wang, Q. Lin, A. Yao, F. Cao, D. Li, J. Zhou, C. Duan, Z. Du, Y. Wang, C. Wang, *Biomaterials* 2012, 33, 3093.

[23] M. Habib, K. Shapira-Schweitzer, O. Caspi, A. Gepstein, G. Arbel, D. Aronson, D. Seliktar, L. Gepstein, *Biomaterials* 2011, 32, 7514.

[24] Y.-B. Lu, K. Franze, G. Seifert, C. Steinhauser, F. Kirchhoff, H. Wolburg, J. Guck, P. Janmey, E.-Q. Wei, J. Käs, A. Reichenbach, *PNAS* 2006, 103, 17759.

[25] M. J. Mahoney, K. S. Anseth, *Biomaterials* 2006, 27, 2265.

[26] F. J. Sim, J. K. Lang, B. Waldau, N. S. Roy, T. E. Schwartz, W. H. Pilcher, K. J. Chandross, S, Natesan, J. E. Merrill, S. A. Goldman, *Ann Neurol* 2006, 59, 763.

[27] K. S. Carbajal, J. L. Miranda, M. R. Tsukamoto, T. E. Lane, *Glia* 2011, 59, 1813.

[28] D. E. Discher, P. Janmey, Y.-l. Wang, *Science* 2005, 310, 1139.

[29] K. Ghosh, X. Z. Shu, R. Mou, J. Lombardi, G. D. Prestwich, M. H. Rafailovich, R. A. F. Clark, *Biomacromolecules* 2005, 6, 2857.

[30] T. Boudou, J. Ohayon, C. Picart, P. Tracqui, *Biorheology* 2006, 43, 721.

[31] J. C. Louis, E. Magal, D. Muir, M. Manthorpe, S. Varon, *J Neurosci Res* 1992, 31, 193.

[32] R. H. Woodruff, R. J. M. Franklin, *Glia* 1999, 25, 216.

Example 15

Short Laminin Peptide for Improved Neural Progenitor Cell Growth

Introduction

Numerous cell types, including stem cells, primary epithelial cells, and primary endothelial cells, require interactions with extracellular matrix (ECM) molecules to support and regulate their survival and proliferation. The ECM not only serves as important structural elements in formations such as the basement membrane, but interacts with cells to influence adhesion, survival, proliferation, migration, and differentiation, through engaging with cellular adhesion receptors, thereby activating a member of downstream signaling pathways[1], Although animal- and human-derived ECM molecules are often necessary for current cell culture applications, there are many problems related to their use. In particular, the ECM component, such as laminin, is an extremely large, complex, post translationally modified protein (850 kDa) that is difficult to produce via recombinant expression systems and thus is commonly purified from mammalian cell lines or tissues. Such protein preparations run the risk of being contaminated with pathogens and immunogens. In addition, there is considerable lot-to-lot variability in animal- and human-derived ECM because many isoforms can be present and the difficulty associated with purifying such proteins to homogeneity. The development of synthetic stem cell culture platforms that mimic the physical and biochemical properties of natural ECM can benefit both scientific studies and clinical therapies. Several short peptides have been identified from full ECM molecules to support cell adhesion and growth, including RGD (Arg-Gly-Asp), IKVAV (Ile-Lys-Val-Ala-Val, SEQ ID NO:16), YIGSR (Tyr-Ile-Gly-Ser-Arg, SEQ ID NO:17), RYVVLPR (Arg-Tyr-Val-Val-Leu-Pro-Arg, SEQ ID NO:18), RNIAEIIKDI (Arg-Asn-Ile-Ala-Glu-Ile-Ile-Lys-Asp-Ile, SEQ ID NO:19), and so on[2]. RGD and IKVAV (SEQ ID NO:16) are present on the α laminin chain, whereas YIGSR (SEQ ID NO:17) is found on the β laminin chain[3,4]. Short peptide sequences have been identified, but none of these peptides from commercial sources can support attachment, growth and long-term culture of human neural stem/progenitor cells (hNPCs).

In this study, we developed a novel peptide sequence with only 12 amino acids based on the laminin sequence IKVAV (SEQ ID NO:16), CCRRIKVAVWLC (SEQ ID NO:1). The novel peptide was examined for its ability to support the attachment, proliferation, and neuronal differentiation of hNPCs in two different contexts: coating on two-dimensional (2D) substrates and conjugated to PEG-based hydrogels for three-dimensional (3D) culture. With the 2D cultures we compared its effects, relative to CSRARKQAASIKVAVSADR (SEQ ID NO:15) from laminin (lam-IKVAV) and the whole protein laminin, on hPNC attachment, proliferation, and differentiation. When conjugated to PEG-based hydrogels, we examined the effects of this short peptide on hPNC attachment, spreading and proliferation on the surface of hydrogels, and also cell migration from human neurospheres cultured inside hydrogels.

Materials

The laminin-IKVAV peptide, CSRARKQAASIKVAVSADR (Cys-Ser-Arg-Ala-Arg-Lys-Gln-Ala-Ala-Ser-Ile-Lys-Val-Ala-Val-Ser-Ala-Asp-Arg, SEQ ID NO:15) was purchased from American Peptide Company (Sunnyvale, Calif.). Reagents required for peptide synthesis, including Fmoc-Cys (Trt)-Wang resin, were obtained from EMD Biosciences (Gibbstown, N.J.). Poly(ethylene glycol)tetra-acetate (MW, 10 kDa, PEGTA) was obtained from Creative PEGWorks (Winston Salem, N.C.). Recombinant fibroblast growth factor-2 (FGF-2) and epidermal growth factor (EGF) were purchased from Peprotech (Rocky Hill, N.J.). Accutase was purchased from Innovative Cell Technologies (San Diego, Calif.). CyQuant proliferation kit and mouse laminin were obtained from Sigma (St. Louis, Mo.). Alexafluor-543 Phalloidin, DAPI (4',6-Diamidino-2-Phenylindole, Dihydrochloride), and LIVE/DEAD viability kit were obtained from Molecular Probes (Eugene, Oreg.). Rabbit anti-glial fibrillary acidic protein (GFAP) was obtained from Dako (Denmark) and mouse anti-β III tubulin from Sigma Aldrich (St. Louis, Mo.). Fluorophore-conjugated secondary antibodies were purchased from Jackson ImmunoResearch (West Grove, Pa.). All other chemical reagents were purchased from Sigma Aldrich (St. Louis, Mo.).

Neural Progenitor Cell Culture

Human neural progenitor cells were obtained from Millipore (Billerica, Mass.). The stem cell is an immortalized neural progenitor cell line derived from the ventral mesencephalon region of human fetal brain and immortalized by retroviral transduction with the v-myc oncogene. In conventional culture, laminin (20 µg/mL) was used to coat tissue culture plastic-wares at least 2 h before hNPC seeding. Human NPCs were maintained in ReNcell Neural Stem Cell Medium (Millipore) with FGF-2 (20 ng/mL) and EGF (20 ng/mL). Human NPCs were incubated at 37° C. under 5% $CO_2$ and used before passage 5 in this study. For cell adhesion assays, cells were removed from the plate using Accutase, aspirated in growth media, and seeded on peptide or laminin coated substrates at a density of 50, 000 cells/cm². For differentiation study, hNPCs were cultured with the medium without FGF-2 and EGF.

Neurosphere Fabrication

Neurospheres with uniform sizes were fabricated using a robotic fabrication system developed in our lab. Briefly, stamps with micronipple array were designed in SolidWorks and fabricated using ultra-precision lathe. The automatic neurospheres fabricator was built on a TT-C3-4040 robot (IAI Corporation, Shizuoka, Japan) with electric triggered gripper to pick up the stamp and pipette tip uptake and ejection actuator to handle liquid. Agarose solution (2% w/w) was prepared by built-in heating elements in the robot platform. The robot was programmed to first add agarose solution to culture dishes. Then the robot picked up the stamp with micronipple arrays on the bottom and pressed on the agarose solution at room temperature for 2 min. Then the highly uniform size microwells were formed in the agarose gel. Human NPC suspension was uptake by the robot and added to the culture well with microwell arrays. After 24 h of culture at 37° C. and 5% $CO_2$, uniform sized neurospheres were formed for this study use. For 3D culture, human neurospheres with uniform size were mixed with hydrogel precursor solutions before hydrogel formation.

Peptide Synthesis and Characterization

The short peptide, CCRRIKVAVWLC (Ac-Cys-Cys-Arg-Arg-Ile-Lys-Val-Ala-Val-Trp-Leu-Cys, SEQ ID NO:1), was synthesized from Fmoc-Cys (Trt) Wang resin (Novabiochem) using standard Fmoc solid phase peptide synthesis protocols. Prior to cleavage from the resin, the free terminal amine was acetylated using 10% acetic anhydride, 10% pyridine in dimethylformamide. The peptide was cleaved from the resin using 94% trifluoroacetic acid, 2.5% ethanedithiol, 2.5% $H_2$), and 1% triisopropylsilane, and was purified by high-pressure liquid chromatography (HPLC) and characterized by mass spectrometry. HPLC was performed using a Waters RCM 25×10 C-18 column. Ion trap mass spectra were obtained using a Finnigan LCQ Advantage Max mass spectrometer. The peptide was stored at −20° C. before stock solutions were made.

Hydrogel Preparation

We have developed a series of functionalized hydrogels based on in situ gelable, non-immunogenic materials, including multi-arm thiolated polyethylene glycol (PEG). Poly(ethylene glycol)tetra-acrylate (PEGTA) was used as the crosslinker for hydrogel formation. Four-arm PEG was chain-end thiolated by esterification reaction with thioglycolic acid (TGA) using p-toluenesulfonic acid as a catalyzer as described before[6,7]. Briefly, 2.5 g of 4-arm PEG, 0.2 g TGA, and 2.5 mg p-toluenesulfonic acid, were added to 100 mL of toluene preheated to 120° C., The reaction proceeded for 24 h under nitrogen atmosphere. The thiolated prepolymer was purified by precipitation into anhydrous ether (200 mL) at 4° C. This sequence was repeated three times using dichloromethane as a solvent. The product was then dried under vacuum at room temperature for 3 days.

Rheological Characterization of Hydrogel

Rheometer (AR1000, TA Instruments) was used to measure hydrogel mechanical properties, such as storage modulus (G') and loss modulus (G"), and gelation time[8]. Briefly, the time sweep was performed to monitor the in situ gelation at 37° C., recording the temporal evolution of G' and G". Frequency sweep test was used to obtain information about the stability of hydrogel structures. The stress sweep was set up by holding the frequency 1 Hz constant while increasing the stress level from 1 to 10 Pa. The applied range of 1-10 Pa was found to be safe-for-use from a prior experiment where we determined the linear viscoelastic region (LVR) profiles of the hydrogels by shearing them until structural breakdown. Oscillatory stress sweep allowed determination of G' of hydrogels.

Peptide Conjugated to Gold Coated Cover Slips

The lam-IKVAV and our synthesized peptide were conjugated to gold-coated cover slips. For gold-coating on glass surfaces, cover slips were first cleaned with ethanol by sonication for 30 min. Then gold was coated on the cover slips by a sputter coater. For peptide and laminin coating, the peptide (150 μg/mL or 100 μM) or laminin (20 μg/mL) solutions were applied on the cover slips for at least 2 h. Then the solutions were removed from the slips and washed with phosphate buffered saline (PBS) for three times. Atomic force microscope (AFM) was used to examine the 3D configuration of the peptides on the surface.

Conjugation of Peptides into Hydrogels

The lam-IKVAV peptide and our synthesized peptide of different concentrations were conjugated to PEG hydrogels through addition reaction of peptide cys thiols onto the ends of a PEGTA crosslinker as described before[9]. Briefly, peptides containing stock solutions (100 μM) were prepared in the PEGTA stock solution (2% w/w) and stirred for 2 h at room temperature. In the peptide-linker stock solutions, the molar ratio of peptides to PEGTA was 1:20. The reaction kinetics of conjugate addition of cys-containing IKVAV peptides to PEGTA was followed using 5,5'-dithio-bis(2-nitrobenzoic acid) (DTNB) reagent according to previous study[9]. Additional PEGTA solutions with lower peptide concentrations of 50 and 10 μM were prepared by diluting the stock solution with peptide-free PEGDA solution (peptide:PEGTA: 1:40 and 1:200, respectively). Then PEGTA solutions containing different concentrations of peptides were added to 4-arm thiolated PEG (2% w/w) solution and mixed thoroughly to form hydrogels.

Cell Attachment and Proliferation

To determine whether peptide-functionalized surfaces can support cell attachment and long-term culture and proliferation, hNPCs were cultured in complete growth medium, which contains FGF-2 and EGF to maintain hNPCs in the undifferentiated state. Cells were incubated at 37° C. with media changed every other day as we routinely culture hNPCs in laminin coated substrates. At the day 1, 5, and 10, cells were assayed with CyQuant (Invitrogen). The cell number was generated through a standard curve.

Cell Morphology

Morphology of cells was examined by immunostaining of actin. Cells were fixed with 4% (w/v) paraformaldehyde, permeabilized with 0.5% Triton X-100 (t-octylphenoxyplyethoxy-ethanol), and stained with Alexa Fluor-543 Phalloidin for 30 min. The nuclei were counterstained with 1 μg/mL DAPI for 30 min. The cells were imaged using a Leica TCS SP5 laser scanning confocal microscope (Bannockburn, Ill.).

Cell Viability

Viability of cells inside hydrogels was examined using LIVE/DEAD Viability Kit, which is a two color fluorescent assay based on differential permeability of live and dead cells and allows preservation of the distinctive staining pattern for a couple of hours after post-fixation with 4% (w/v) glutaraldehyde. Live cells were stained with green fluorescent SYTO 10; and dead cells with compromised cell membranes were stained with red fluorescent ethidium homodimer-2. The Leica TCS SP5 laser scanning confocal microscope was used to capture the images of the LIVE/DEAD cell staining patterns.

Cell Differentiation

The differentiation of hNPCs on the tested surfaces was assayed by immunocytochemistry. Human NPCs were cultured for 2 weeks with differentiation media without growth factors FGF-2 and EGF. The cells were fixed with 4% (w/v) paraformaldehyde, treated with 5% goat serum in PBS to block non-specific reactivity and incubated overnight at 4° C. with primary antibodies, such as β III tubulin and glial fibrillary acidic protein (GFAP). After washing with PBS three times, the samples were incubated with the secondary antibodies at room temperature for 3 h. Then the nuclei were counterstained with DAPI for 30 min. The samples were imaged using the same microscope as described before. At least 6 random fields per surface were analyzed for each group.

Statistical Analysis

Data are shown as mean±stand deviation. Statistical analyses were performed using one-way ANOVA (analysis of variance) followed by Tukey's post tests and the paired t-test where appropriate. A probability (p) value of <0.05 was considered statistically significant.

Data Analysis

Human NPCs Cultured on Peptide Coated Surface

Figure 17:
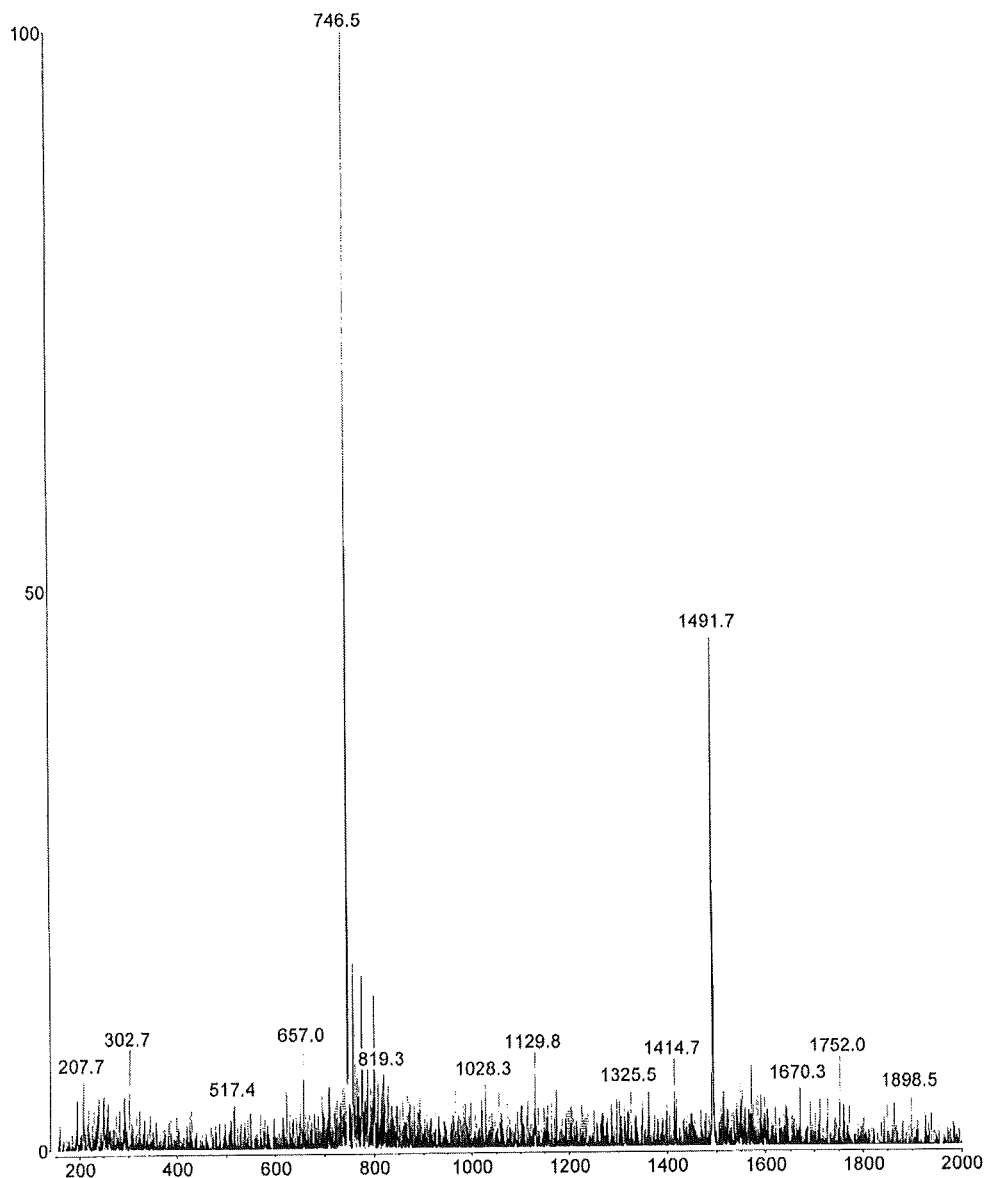
FIG. 17. Mass spectrum of the peptide sequence, CCR-RIKVAVWLC (SEQ ID NO:1).

The sequence of the polypeptide CCRRIKVAVWLC (SEQ ID NO:1) was confirmed by mass spectrometry with the mass to charge ratio of 1491.7 (calculated at 1491.77, FIG. 17). Both our synthesized peptide and the lam-IKVAV peptide were immobilized onto gold coated glass cover slips because of the specific interaction between the sulfur of cysteine and gold.

Figure 18:
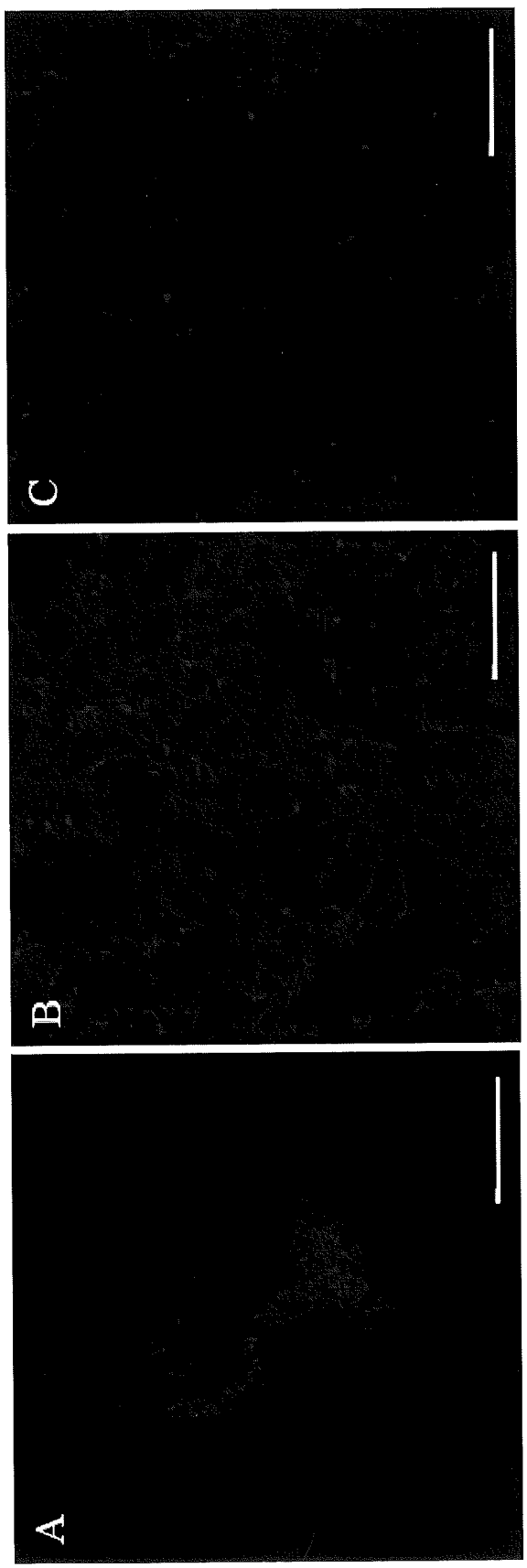
FIG. 18A-18C. Human neuronal progenitor cells (hNPCs) cultured on the gold-coated cover slips conjugated with (A) lam-IKVAV peptide, (B) our novel IKVAV peptide, and coated with (C) laminin. Cells were stained with phalloidin for actin (red). Scale bar=100 µm.
Figure 19:
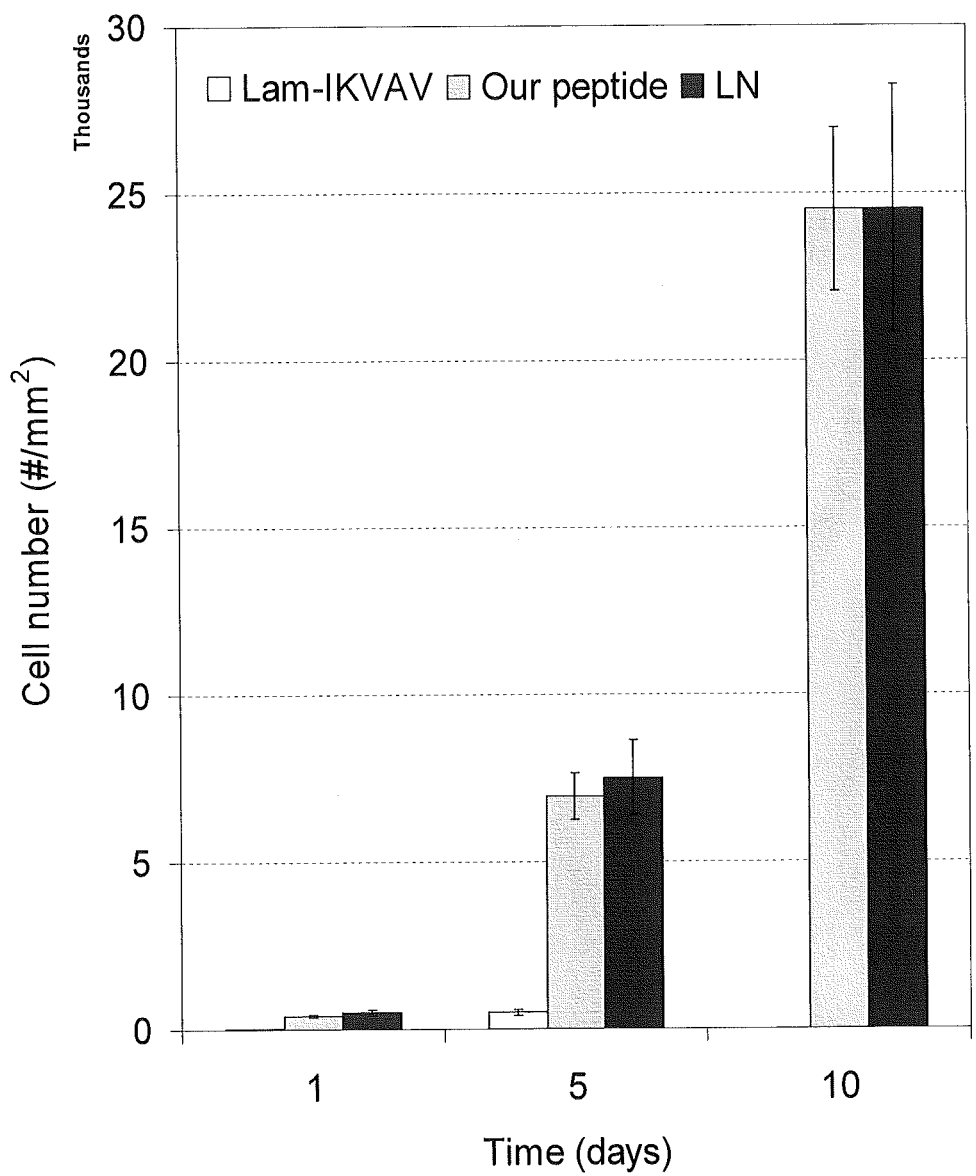
FIG. 19. Quantification of hNPCs attached and proliferated on the gold-coated cover slips conjugated with lam-IKVAV peptide and our novel IKVAV peptide, and coated with laminin (LN). A greater number of cells attached on cover slips conjugated with our peptide than lam-IKVAV peptide at the day 1 (inserted, * p<0.05).

As show in FIG. 18, on the lam-IKVAV modified surface, hNPCs preferred to aggregate together. In contrast, on the surface modified with our synthesized peptide, they spread more evenly, similar to those on whole laminin coated surface. As for cell attachment and proliferation, on the lam-IKVAV modified surface, at the first day, very few cells attached. Later, the adhered cells aggregated together at the day 5 and floated off the surface at the day 10. In contrast, on our new short peptide coated surface, at the day 1, there were significantly much more cells attached compared to lam-IKVAV (FIG. 19, insert, p<0.05). These attached cells spread evenly and proliferated on our novel peptide modified surface. They were totally confluent on the whole surface at the day 10. There was no significant difference between our novel peptide modified surface and laminin coated surface.

Figure 20:
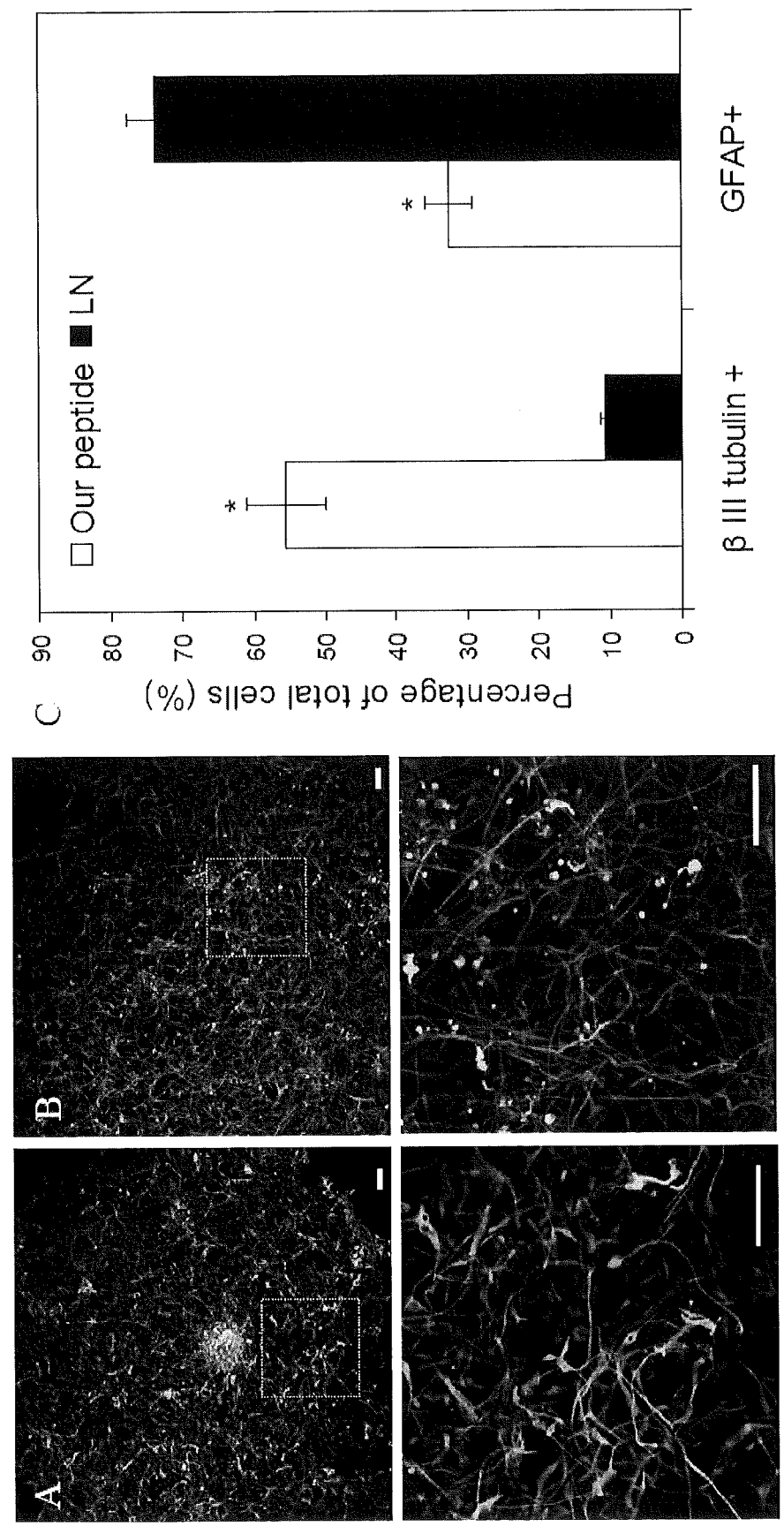
FIG. 20A-20C. (A) Differentiation of hNPCs cultured on cover slips (A) conjugated with our novel peptide and (B) coated with laminin (LN) at the day 14. (C) Qualification of cells that differentiated into neurons (β tubulin+) and astrocytes (GFAP+). Our novel peptide had significantly much neurons and fewer astrocytes compared to LN (*p<0.05).

Since lam-IKVAV could not support long-term culture of hNPCs, in order to investigate the effects of our short peptide on cell differentiation, laminin coated surface was used as control for comparison. The cells were cultured in differentiation media without FGF-2 and EGF for 2 weeks. Immunocytochemistry was used to establish in vitro differentiation of hNPCs. In addition to cellular morphology, neurons can be identified by expression of β III tubulin and astrocytes by expression of GFAP (FIG. 20). More than half of hNPCs on our short peptide coated surface differentiated into neurons. In contrast, there were about 30% GFAP astrocyte differentiation after 2 weeks. When compared to whole laminin coating, our novel peptide had significantly much more neurons (54% as opposed to 11%, p<0.05) and fewer astrocytes (33% as opposed to 74%, p<0.05) by 2 weeks (FIG. 20 C).

Human NPCs Cultured on the Surface of Hydrogels Conjugated with Peptides

Figure 21:
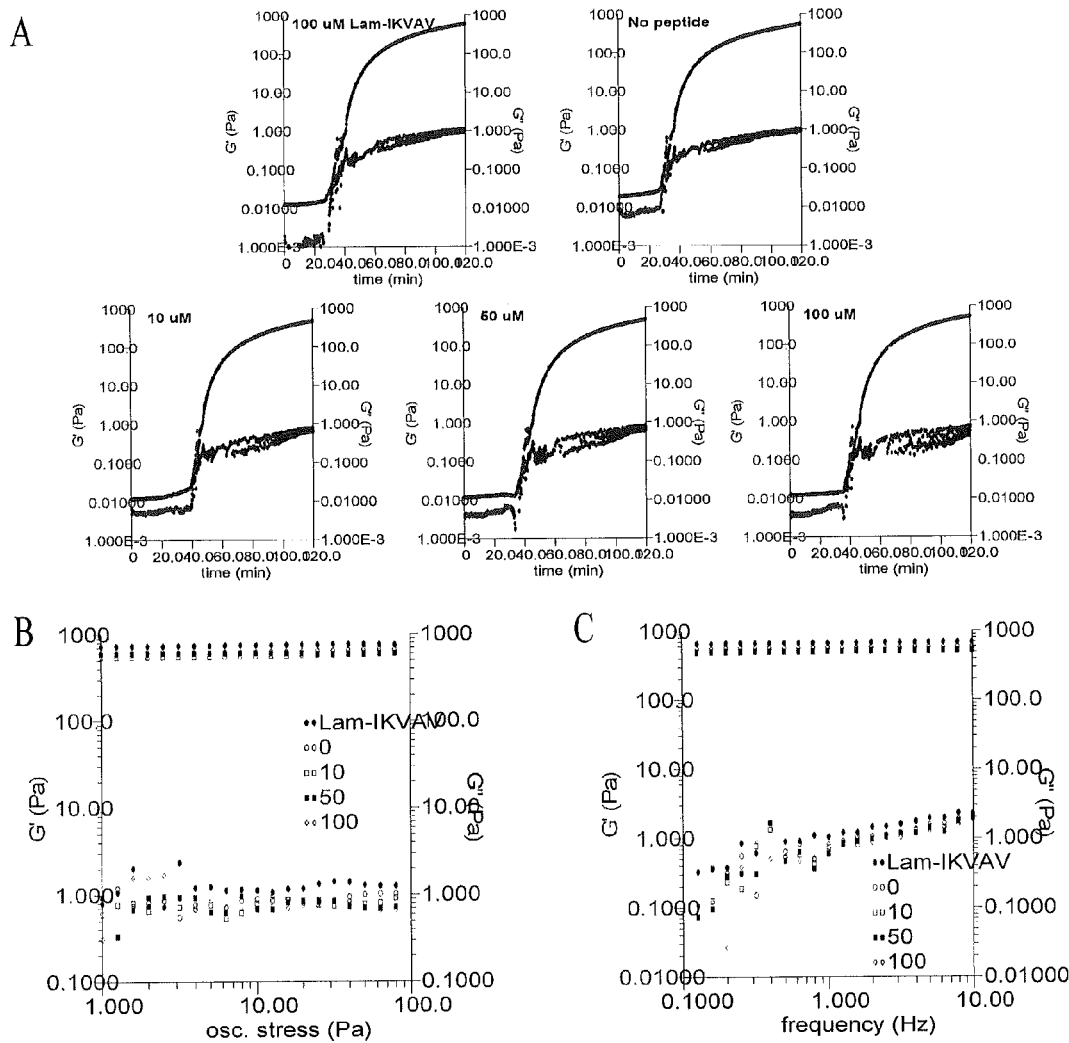

Four-arm thiolated PEG was crosslinked by PEGTA through Michael-type addition reaction. As shown in FIG. 21, the solutions of 4-arm thiolated PEG (2% w/w) and PEGTA (2% w/w), started the gelation process at 30 min (when G'>G", FIG. 21A, no peptide) and formed the stable hydrogel at 2 h with G' about 600 Pa (FIGS. 21B and 21C).

Peptides were incorporated into the hydrogel by conjugate addition of peptide cys thiols onto the ends of PEGTA. The conjugation reaction was complete within 5 min according to the DTNB test (data not shown). Since this conjugation reaction just consumed very small amount of PEGTA (less than 2.5% of total amount) even with the highest concentration of our peptide (100 µM), the peptide addition did not affect the subsequent use of PEGTA for hydrogel crosslinking. Hydrogels conjugated with different amounts of our peptide (10, 50, and 100 µM) expressed similar stiffness about 600 Pa (FIGS. 21B and 21C), even though the gelation process of all of our peptide conjugated hydrogels started a little bit later (40 min) than both blank hydrogel and lam-IKVAV conjugated hydrogel (30 min).

Figure 22:
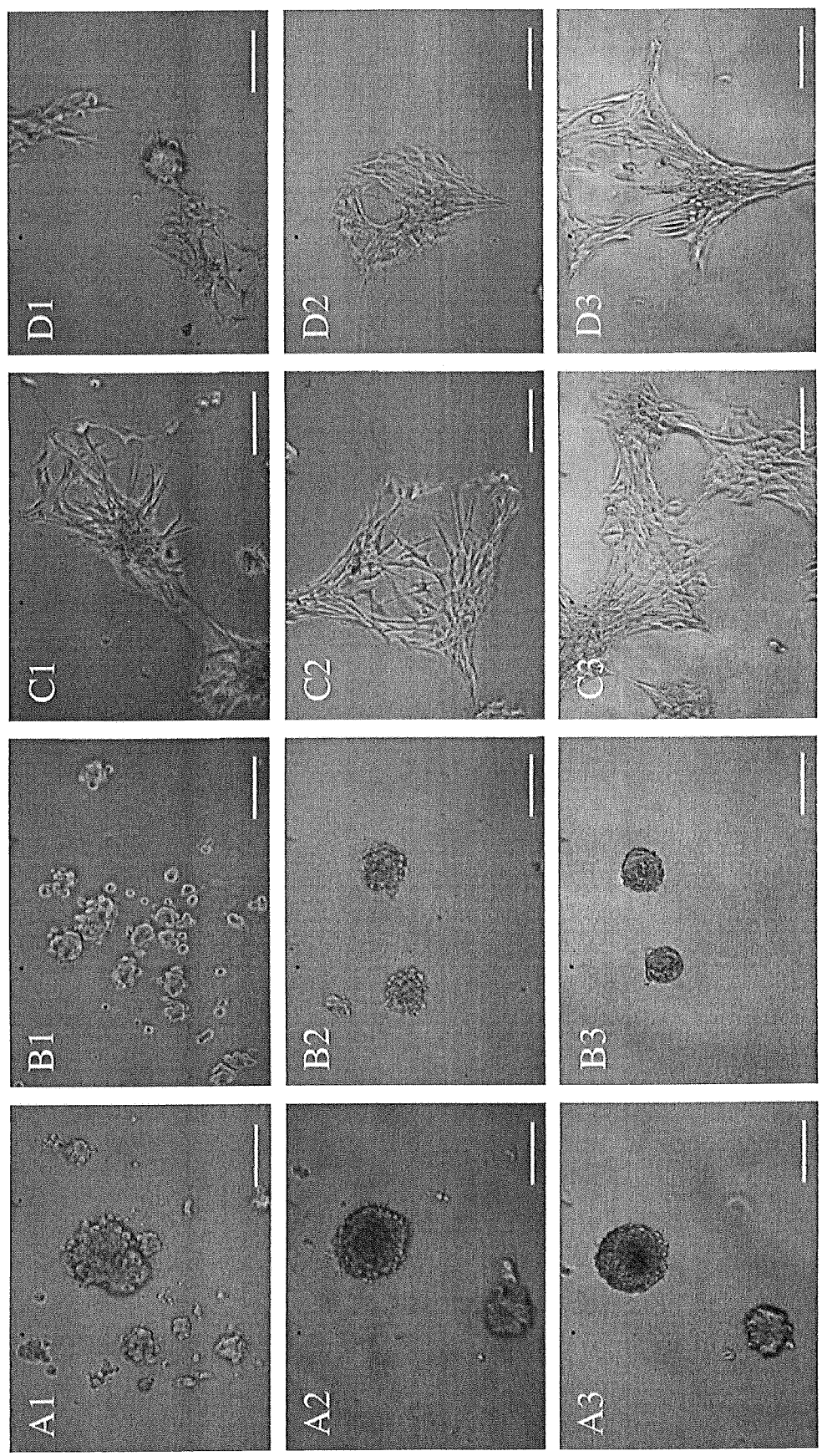
Figure 23:
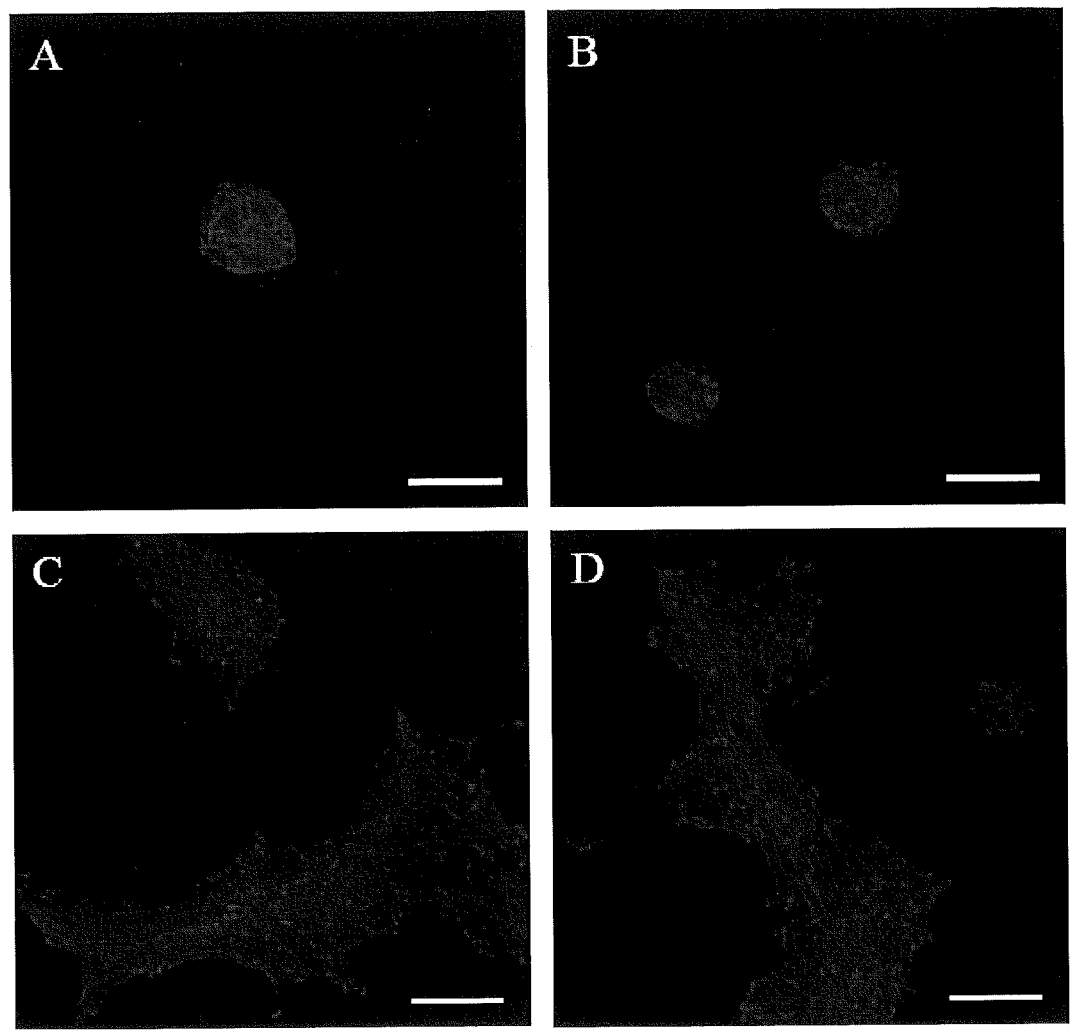

Human NPCs were cultured on the surface of hydrogels with maintain media for 7 days. Without any bioactive peptide, hNPCs could not attach on the surface of blank PEG hydrogels (FIG. 22B). The cells formed spheres by themselves at the day 3. Similar to those on plain hydrogels, cells on hydrogels conjugated with lam-IKVAV (100 µM) also aggregated together (FIG. 22A). In contrast, on the hydrogels conjugated with our short peptide of both 10 and 100 µM, cells attached at the day 1. These attached cells proliferated on the surface as the function of time (FIGS. 22C and 22D). Shown in FIG. 23, at the day 7, only on the hydrogel conjugated with our short peptide (10 and 100 µM), hNPCs displayed spreading cytoskeletons. There was no difference about the morphology of hNPCs between these two groups.

Human Neurospheres Cultured Inside Hydrogels Conjugated with Our Short Peptide

Uniformly sized neurosphere is a good in vitro model to study cell migration in different biomaterial structures and formulations. Human neurospheres with uniform size about 400 µm were shown in FIG. 24. Human NPCs inside of our fabricated spheroids maintained their stemness as demonstrated by nestin positive staining. The size of neurospheres could be manipulated through adjusting the concentrations of cell suspensions.

Human neurospheres with uniform size were mixed with hydrogel precursor solutions including 2% (w/w) thiolated 4-arm PEG and 2% (w/w) PEGTA conjugated with lam-IKVAV of 100 µM and our short peptide of different concentrations of 0, 10, 50, and 100 µM. After hydrogel formation, cells were cultured in media without FGF-2 and EGF for 3 weeks. As presented in FIG. 25, the cells survived the in situ crosslinking process and remained viable during the time of observation (21 days). The viability of hNPCs inside hydrogels was very high (>95%) regardless of the type and concentration of peptide.

Figure 27:
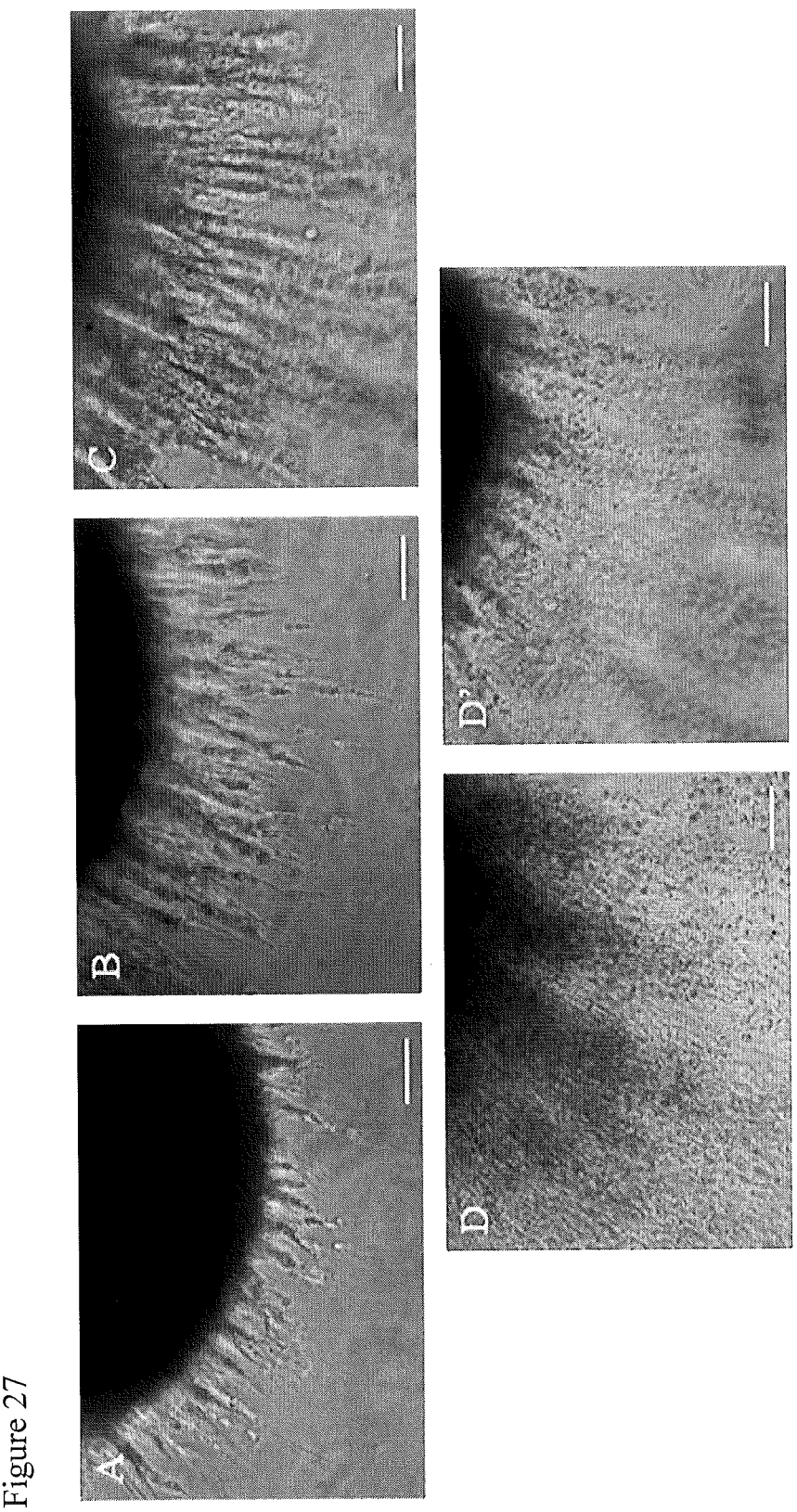

However, the conjugated peptides resulted in a different response on cell migration. We quantified the cell migration by taking measurements of the distance between the edge of spheres and the cell bodies at their outer perimeters. FIG. 26 presents quantification of cell migration from neurospheres cultured inside hydrogels conjugated with lam-IKVAV of 100 µM and our novel IKVAV peptide of different concentrations of 0, 10, 50, and 100 µM at the day 3, 7, and 21. Human NPCs encapsulated in the hydrogel without peptide failed to migrate at the day 3. Just very few hNPCs migrated from neurosphere at both 7 and 21 days. When compared to the blank hydrogel group, hNPCs, in all of peptide conjugated hydrogels showed a greater ability to migrate. By contrast, hNPCs, encapsulated in hydrogels with our short peptide of 10 µM, expressed the greatest ability to migrate and 2-fold longer distance of hNSCs migration at all the day of 3, 7, and 21 (FIG. 26, p<0.05). As shown in FIG. 27, individual cells could be seen to migrate away from the edge of the cell mass. Migration of cells was statistically significant as a function of time (FIG. 26, p<0.05).

Discussion

Figure 28:
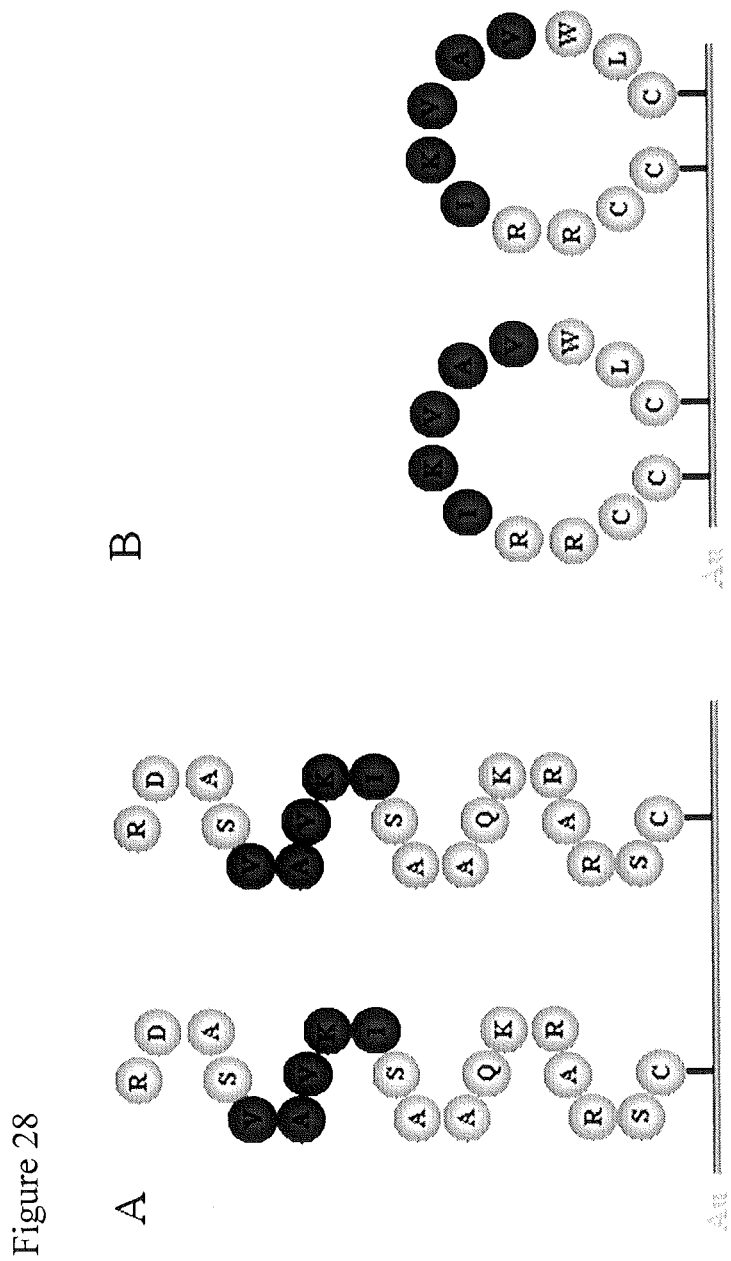
Figure 29:
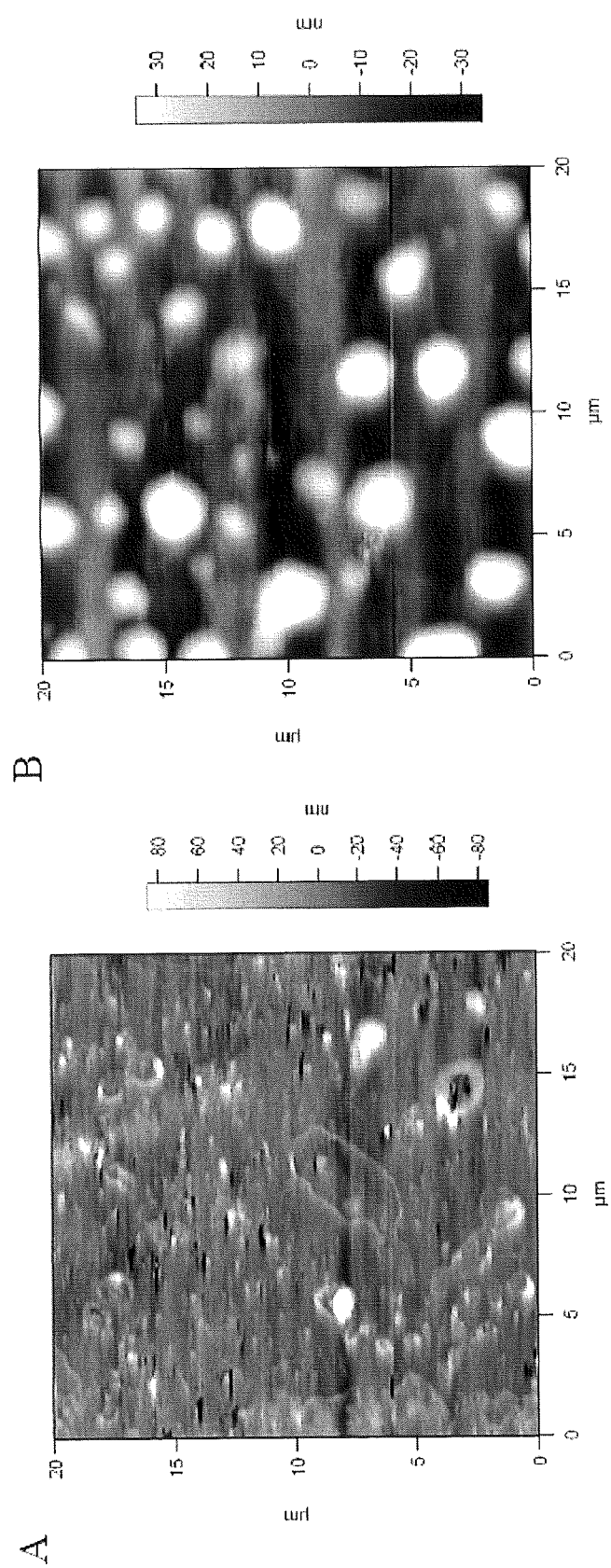

In this study, one new short peptide sequence, CCR-RIKVAVWLC (SEQ ID NO:1), including the cell adhesion motif sequence, IKVAV (SEQ ID NO:16), has been successfully developed by a solid phase synthesis protocol. In the sequence design, two cysteines are located in the N-terminus and another at the C-terminus. Due to the specific interaction between the sulfur of cysteine and the substrate, such as a gold coated glass surface, peptides can be immobilized onto the substrates[10-13]. Since there are another two cysteines available in the sequences, our short peptides, when conjugated to the substrate, possess the capability to assume a looped conformation, so the it can present the IKVAV sequence (SEQ ID NO:16) better to the cells. In contrast, the lam-IKVAV peptide, CSRARKQAASIKVAVSADR (SEQ ID NO:15), which only has one cysteine in its sequence, can not cannot form a cyclic structure on substrates. FIG. 28 shows the scheme of lam-IKVAV peptide and our novel IKVAV peptide conjugated to gold coated cover slips. As shown in FIG. 29, the morphologies of lam-IKVAV peptide and our novel IKVAV peptide conjugated to gold-coated cover slips have been examined by atomic force microscopy. The peptide formed 3D tall dots (bright spots) on the surface coated with our short peptide. In contrast, there are very few tall dots (bright spots) on the surface coated with lam-IKVAV peptides. This clearly indicates that our short peptide forms a 3D loop structure and presents the IKVAV sequence (SEQ ID NO:16) better than the lam-IKVAV peptide which forms linear 2D structures rather than loop 3D structures. Moreover, through a Michael-type addition reaction between thiols of the peptide and double bonds of PEGTA, the novel peptide can also be conjugated with PEG hydrogels with a looped structure similar to that on the 2D culture substrates. The reaction between thiol and acrylate rather than the formation of a disulfide bond between thiols is strongly preferred because kinetically the rate of reaction between thiol and acrylate (about 5 min) is much more rapid than the rate of reaction between thiol groups (11 h)[14].

The effects of lam-IKVAV and our short peptide on cell adhesion were compared in this study. When immobilized to the 2D surface, although the lam-IKVAV may promote hNPC adhesion, it does not elicit a stable attachment. Our short IKVAV peptide, just like the whole laminin molecule, supports hNPC attachment, spreading, and proliferating until total confluence on the whole surfaces is achieved. The greater efficacy and consistency of our short peptide on cell adhesion may have resulted from the better presentation of IKVAV sequence to cell receptors than the linear lam-IKVAV peptide as described above. Similar to our result, Kämmerer and coworkers have demonstrated that cyclic-RGD modified surfaces showed a significantly increased influence on endothelial cell adhesion and proliferation compared to the linear-RGD modified surfaces[15].

When compared to laminin, our peptide has directed NPC differentiation to neurons. The reason lies in the fact that our peptide, compared to the whole molecule laminin, has presented to cells higher density of bioactive IKVAV, which has promoted cell differentiation[16]. Previous studies have shown that the concentration of surface peptide conjugated to gold surface is between $2 \times 10^{-11}$ and $1 \times 10^{-10}$ mol/cm$^2$ [17-19]. So our peptide presents to cells at least $1.2 \times 10^{13}$ IKVAV epitopes/ cm². By contrast, closely packed laminin protein molecules in a two-dimensional lattice on a solid substrate have an estimated 7.5×10¹¹ IKVAV epitopes/cm² [16]. Our short peptide could amplify the epitope density relative to a laminin monolayer at least over 10 times. Moreover, in comparison to laminin, our synthesized peptide is less likely to exhibit steric hindrance and much more stable[5]. Furthermore, our peptide is very short and very easy to synthesize, and also very low cost. With this peptide sequence, the need for human and animal sources of laminin in cell culture will be minimal, or even eliminated.

PEG acts as an inert structural platform due to its hydrophilicity and resistance to protein adsorption[20]. The lam-IKVAV peptide, when conjugated to PEG hydrogels, did not support any hNPC attachment. This result is consistent with a previous study, in which the same peptide failed to induce adhesion or proliferation of rat hippocampus NPCs when grafted to an interpenetrating poly(acrylamide) hydrogel surface[21]. In contrast, our novel peptide improved hNPC attachment, spreading and proliferation on the surface of our conjugated PEG hydrogels. The greater efficacy of our short peptide on cell adhesion may have resulted from the better presentation of the IKVAV sequence (SEQ ID NO:16) to cell receptors than the linear lam-IKVAV peptide in hydrogel configuration. Yu and coworkers also demonstrated that CDPGYIGSR (SEQ ID NO:20), which more closely mimics the native region conformation of the active sites, exhibited greater cellular responses as compared to GYIGSR (SEQ ID NO:21) when conjugated to poly(2-hydroxyethyl methylacrylate) hydrogels In this study, when our short IKVAV peptide was conjugated to hydrogels in a concentration series, the peptide resulted in a response with the maximum enhancement of cell migration at peptide density of 10 μM. Higher concentration of peptides exhibited inhibitory effects on cell migration (FIG. 26). It has been shown that migration of cells within hydrogels involves the dynamic interaction between cell surface receptors and adhesion ligands in the hydrogels, with the strength related to the concentration of cell-surface receptors, the concentration of ligands available, the specific binding affinity of the receptor-ligand pairs, the microscopic porosity of hydrogels, and so on[23, 24]. The corresponding rate of cell migration depends on the simultaneous detachment and attachment to nearby ligands, causing extreme ligand densities (both high and low) to inhibit one of these two processes and subsequently limit cell migration rates. Moreover, our result is also consistent to previous studies which demonstrated that the biphasic response of cell migration depending on peptide density was more prevalent at higher receptor-ligand binding affinity[2, 23, 25].

The application of specific peptides has received much attention for use in hydrogel modification for neural tissue regeneration[26]. For example, one group used Factor XIIIa in order to covalently attach certain exogenous bioactive peptides within fibrin hydrogels during crosslinking. It was found that these peptide sequences, including RGD, IKVAV (SEQ ID NO:16), HAV (His-Ala-Val) and RNIAEIIKDI (SEQ ID NO:19), all enhanced neurite extension of chicken embryo dorsal root ganglions (DRGs) individually, though different behavior types, including, inhibitory, additive, noninteractive, and synergism, were seen when they were incorporated in combination[2, 27].

Another group developed a complex structure by self-assembly of peptide amphiphile molecules. By incorporating the IKVAV sequence, these nanofiber hydrogels were been shown to inhibit glial scar formation, enhance differentiation of neural progenitor cells, and promote axon elongation, which ultimately resulted in behavioral improvements after spinal cord injury in mice once implanted in vivo[16, 28]. The PEG hydrogels of this invention conjugated with our short peptide show great potential for neural tissue regeneration[29, 30]. Firstly, our in situ crosslinkable hydrogels would be strongly preferred because the injectable material could be formed into any desired shape at the site of injury and the crosslinkable polymer mixture would adhere to the tissue during gelation, and the mechanical interlocking arising from irregular interfaces would strengthen the tissue-hydrogel integration. Secondly, the novel IKVAV peptide of this invention promotes 3D cell migration, a desirable trait that is useful in attracting endogenous stem cells to injured/diseased areas, an important aspect of neural tissue regeneration[31, 32].

Conclusions

A short peptide sequence with only 12 amino acids has been developed, CCRRIKVAVWLC (SEQ ID NO:1). This novel peptide, when compared to, for example, the lam-IKVAV peptide, enhances/increases NPC attachment and proliferation, and also promotes NPC differentiation into neurons. When conjugated to PEG hydrogels, this specific peptide supports NPC attachment and proliferation on the surface of hydrogels, and enhanced/increased cell migration with a maximum enhancement at a peptide density of 10 μM. This novel short peptide shows great promise in stem cell culture and neural tissue regeneration applications. This study provides additional tools for addressing stem cell growth and differentiation for use in treating a wide variety of disorders.

Example 16

References for Example 15

1. Tzu J, Marinkovich M P. Bridging structure with function: Structural, regulatory, and developmental role of laminins. Int. J. Biochem. Cell. Biol. 2008; 40:199-214.
2. Schense J C, Bloch J, Aebischer P, et al. Enzymatic incorporation of bioactive peptides into fibrin matrices enhances neurite extension. Nat. Biotechnol. 2000; 18:415-419.
3. Graf J, Ogle R C, Robey F A, et al. A pentapeptide from the laminin B1 chain mediates cell adhesion and binds to 67000 laminin receptor. Biochemistry. 1987; 26:6896-6900.
4. Kleinman H K, Weeks B S, Cannon F B, et al. Identification of a 110-kDa nonintegrin cell surface laminin-binding protein which recognizes an a chain neurite-promoting peptide. Arch. Biochem. Biophys. 1991; 290:320-325.
5. Hersel U, Dahmen C, Kessler H. RGD modified polymers: biomaterials for stimulated cell adhesion and beyond. Biomaterials. 2003; 24:4385-4415,
6. Yu H, Feng Z, Zhang A, et al. Synthesis and characterization of three-dimensional crosslinked networks based on self-assembly of α-cyclodextrins with thiolated 4-arm PEG using a three-step oxidation. Soft Matter. 2006; 2:343-349.
7. Li X, Liu X, Zhao W, et al. Manipulating neural-stem-cell mobilization and migration in vitro. Acta Biomater. 2012; 8:2087-2095.
8. Ghosh K, Shu X, Mou R, et al. Rheological characterization of in situ cross-linkable hyaluronan hydrogels. Biomacromolecules. 2005; 6:2857-2865.
9. Shu X, Ghosh K, Liu Y, et al. Attachment and spreading of fibroblasts on an RGD peptide-modified injectable hyaluronan hydrogel. J. Biomed. Mater. Res. A. 2004; 68A:365-375.

10. Bastús N G, Sanchez-Tilló E, Pujals S, et al. Homogeneous conjugation of peptides onto gold nanoparticles enhances macrophage response. ACS Nano. 2009; 3:1335-1344.
11. Bain C D, Troughton E B, Tao Y T, et al. Formation of monolayer films by the spontaneous assembly of organic thiols from solution onto gold. J. Am. Chem. Soc. 1989; 111:321-335.
12. Nuzzo R G, Allara D L. Adsorption of bifunctional organic disulfides on gold surfaces. J. Am. Chem. Soc. 1983; 105:4481-4483.
13. Nuzzo R G, Fusco F A, Allara D L. Spontaneously organized molecular assemblies. 3. Preparation and properties of solution adsorbed monolayers of organic disulfides on gold surfaces. J. Am. Chem. Soc. 1987; 109:2358-2368.
14. Elbert D L, Pratt A B, Lutolf M P, et al. Protein delivery from materials formed by self-selective conjugate addition reactions. J. Controlled Release. 2001; 76:11-25.
15. Kämmerer P W, Heller M, Brieger J, et al. Immobilisation of linear and cyclic RGD-peptides on titanium surfaces and their impact on endothelial cell adhesion and proliferation. Eur Cell Mater. 2011; 21:364-372.
16. Silva G A, Czeisler C, Niece K L, et al. Selective differentiation of neural progenitor cells by high-epitope density nanofibers. Science. 2004; 303:1352-1355.
17. McMillan R, Meeks B, Bensebaa F, et al. Cell adhesion peptide modification of gold-coated polyurethanes for vascular endothelial cell adhesion. J. Biomed. Mater. Res. 2001; 54:272-283.
18. Sun X, Sheardown H, Tengvall P, et al. Peptide modified gold-coated polyurethanes as thrombin scavenging surfaces. J. Biomed. Mater. Res. 2000; 49:66-78.
19. Saneinejad S, Shoichet M S. Patterned glass surfaces direct cell adhesion and process outgrowth of primary neurons of the central nervous system. J. Biomed. Mater. Res. 1998; 42:13-19.
20. Whitesides G. Poly(ethylene glycol) chemistry biotechnical and biomedical applications J. Milton Harris, Ed. Appl. Biochem. Biotechnol. 1993; 41:233-234.
21. Saha K, Irwin E F, Kozhukh J, et al. Biomimetic interfacial interpenetrating polymer networks control neural stem cell behavior. J. Biomed. Mater. Res. A. 2007; 81A:240-249.
22. Yu T T, Shoichet M S. Guided cell adhesion and outgrowth in peptide-modified channels for neural tissue engineering. Biomaterials. 2005; 26:1507-1514.
23. Schense J C, Hubbell J A. Three-dimensional migration of neurites is mediated by adhesion site density and affinity. J. Biol. Chem., 2000; 275:6813-6818.
24. Raeber G P, Lutolf M P, Hubbell J A. Molecularly engineered PEG hydrogels: a novel model system for proteolytically mediated cell migration. Biophys. J. 2005; 89:1374-1388.
25. Palecek S P, Loftus J C, Ginsberg M H, et al. Integrin-ligand binding properties govern cell migration speed through cell-substratum adhesiveness. Nature. 1997; 385: 537-540.
26. Sur S, Pashuck E T, Guler M O, et al. A hybrid nanofiber matrix to control the survival and maturation of brain neurons. Biomaterials. 2012; 33:545-555.
27. Pfaff M, Tangemann K, Müller B, et al. Selective recognition of cyclic RGD peptides of NMR defined conformation by alpha IIb beta 3, alpha V beta 3, and alpha 5 beta 1 integrins. J. Biol. Chem. 1994; 269:20233-20238.
28. Tysseling-Mattiace V M, Sahni V, Niece K L, et al. Self-assembling nanofibers inhibit glial scar formation and promote axon elongation after spinal cord injury. J. Neurosci. 2008; 28:3814-3823.
29. Bjugstad K B, Redmond Jr D E, Lampe K J, et al. Biocompatibility of PEG-based hydrogels in primate brain. Cell Transplantation. 2008; 17:409-415.
30. Bjugstad K B, Lampe K, Kern D S, et al. Biocompatibility of poly(ethylene glycol)-based hydrogels in the brain: An analysis of the glial response across space and time. J. Biomed. Mater. Res. A. 2010; 95A:79-91.
31. Jin K, Mao X, Xie L, et al. Transplantation of human neural precursor cells in Matrigel scaffolding improves outcome from focal cerebral ischemia after delayed postischemic treatment in rats. J. Cereb. Blood Flow Metab. 2009; 30:534-544.
32. Makoto U, Mohamed M R, Mizuya S, et al. Matrigel supports survival and neuronal differentiation of grafted embryonic stem cell-derived neural precursor cells. J. Neurosci. Res. 2010; 88:542-551.

The foregoing is illustrative of the present invention, and is not to be construed as limiting thereof. The invention is defined by the following claims, with equivalents of the claims to be included therein. All publications, patent applications, patents, patent publications, and any other references cited herein are incorporated by reference in their entireties for the teachings relevant to the sentence and/or paragraph in which the reference is presented.

---

What is claimed is:

1. A cell culture platform, comprising: a two dimensional and/or three dimensional surface comprising peptides conjugated to said surface, wherein said peptides comprise the amino acid sequence CCRRIKVAVWLC (SEQ ID NO: 1).

2. The cell culture platform of claim 1, wherein the two dimensional surface is an in vitro cell culturing surface.

3. The cell culture platform of claim 1, wherein the three dimensional surface is a hydrogel.

4. The cell culture platform of claim 1, wherein the peptides are conjugated to said surface at a concentration of 10 µM or less.

5. A method of increasing cell adhesion, stable attachment and/or proliferation of cells on two dimensional and/or three dimensional surfaces, comprising:

contacting the cells with the platform of claim 1; and
culturing the cells, wherein the cultured cells have increased cell adhesion, stable attachment and proliferation as compared to a control.

6. The method of claim 5, wherein the cells are stem cells.

7. The method of claim 6, wherein the stem cells are neural stem cells or neural progenitor cells (NPCs).

8. The method of claim 7, wherein the neural stem cells or neural progenitor cells are human.

9. A method of promoting differentiation of neural stem cells or neural progenitor cells into neurons, comprising: contacting neural stem cells or neural progenitor cells with the platform of claim 1; and culturing the cells on said platform, thereby promoting the differentiation of the cells into neurons.

10. The method of claim 9, wherein the neural stem cells or neural progenitor cells are human.

* * * * *

UNITED STATES PATENT AND TRADEMARK OFFICE
CERTIFICATE OF CORRECTION

PATENT NO. : 8,609,409 B2  
APPLICATION NO. : 13/598343  
DATED : December 17, 2013  
INVENTOR(S) : Li et al.

Page 1 of 1

It is certified that error appears in the above-identified patent and that said Letters Patent is hereby corrected as shown below:

In the Specification:

Column 39, Line 48: Please correct "[7] a Tsuji,"
to read -- [7] O. Tsuji, --

Column 44, Line 59: Please correct "about 30% GFAP astrocyte"
to read -- about 30% GFAP$^+$ astrocyte --

Column 46, Line 22: Please correct "sequence, can not cannot form a"
to read -- sequence, cannot form a --

Column 47, Lines 29-30: Please correct "methylacrylate) hydrogels"
to read -- methylacrylate) hydrogels$^{22}$. --

Column 48, Line 52: Please correct "materials. 2003; 24:4385-4415,"
to read -- materials. 2003; 24:4385-4415. --

Signed and Sealed this
Eighth Day of July, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,609,409 B2
APPLICATION NO. : 13/598343
DATED : December 17, 2013
INVENTOR(S) : Li et al.

It is certified that error appears in the above-identified patent and that said Letters Patent is hereby corrected as shown below:

In the Specification

Column 1, Line 15, STATEMENT OF GOVERNMENT SUPPORT: Please replace the entire paragraph to read as follows:

-- This invention was made with government support under Grant Nos. R01 NS050243 and P20 RR021949 awarded by the National Institutes of Health, Grant Number CBET 0748129 awarded by the National Science Foundation and Grant Number W81XWH-10-1-0954 awarded by the Department of Defense. The government has certain rights in the invention. --

Signed and Sealed this
Sixth Day of October, 2015

Michelle K. Lee
*Director of the United States Patent and Trademark Office*